(12) United States Patent
Bell et al.

(10) Patent No.: US 9,505,823 B2
(45) Date of Patent: Nov. 29, 2016

(54) ALBUMIN-INSULIN FUSION PROTEINS

(75) Inventors: Adam C. Bell, Germantown, MA (US);
Craig A. Rosen, Laytonsville, MA (US); Indrajit Sanyal, Bethesda, MA (US); Qinghai Zhao, Gaithersburg, MA (US)

(73) Assignee: TEV A Biopharmaceuticals USA, Inc., Rockville, MD (US)

( * ) Notice: Subject to any disclaimer, the term of this patent is extended or adjusted under 35 U.S.C. 154(b) by 1781 days.

(21) Appl. No.: 11/835,114

(22) Filed: Aug. 7, 2007

(65) Prior Publication Data

US 2008/0057004 A1 Mar. 6, 2008

Related U.S. Application Data

(60) Provisional application No. 60/835,976, filed on Aug. 7, 2006, provisional application No. 60/850,545, filed on Oct. 10, 2006.

(51) Int. Cl.
*A61K 38/28* (2006.01)
*C07K 14/62* (2006.01)
*C12N 15/17* (2006.01)
*A61P 5/50* (2006.01)
*A61P 3/10* (2006.01)
*C12N 15/62* (2006.01)
*C07K 14/765* (2006.01)

(52) U.S. Cl.
CPC ............... *C07K 14/62* (2013.01); *A61K 38/28* (2013.01); *C07K 14/765* (2013.01); *C12N 15/62* (2013.01); *C07K 2319/35* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,002,531 A | 1/1977 | Royer | |
| 4,179,337 A | 12/1979 | Davis et al. | |
| 4,485,045 A | 11/1984 | Regen | |
| 4,544,545 A | 10/1985 | Ryan et al. | |
| 4,619,794 A | 10/1986 | Hauser | |
| 4,736,866 A | 4/1988 | Leder et al. | |
| 4,857,467 A | 8/1989 | Sreekrishna et al. | |
| 4,873,191 A | 10/1989 | Wagner et al. | |
| 5,073,627 A | 12/1991 | Curtis et al. | |
| 5,122,464 A | 6/1992 | Wilson et al. | |
| 5,283,184 A | 2/1994 | Jorgensen et al. | |
| 5,349,052 A | 9/1994 | Delgado et al. | |
| 5,482,852 A | 1/1996 | Yoder et al. | |
| 5,489,743 A | 2/1996 | Robinson et al. | |
| 5,519,115 A * | 5/1996 | Mapelli et al. | 530/324 |
| 5,576,195 A | 11/1996 | Robinson et al. | |
| 5,602,307 A | 2/1997 | Beaudet et al. | |
| 5,612,460 A | 3/1997 | Zalipsky | |
| 5,641,670 A | 6/1997 | Treco et al. | |
| 5,643,575 A | 7/1997 | Martinez et al. | |
| 5,720,936 A | 2/1998 | Wadsworth et al. | |
| 5,723,719 A | 3/1998 | Ratty et al. | |
| 5,728,915 A | 3/1998 | Chang et al. | |
| 5,731,489 A | 3/1998 | Ganten et al. | |
| 5,731,490 A | 3/1998 | Mak et al. | |
| 5,783,423 A | 7/1998 | Wood et al. | |
| 5,846,818 A | 12/1998 | Robinson et al. | |
| 5,866,546 A | 2/1999 | Gross et al. | |
| 5,965,386 A | 10/1999 | Kerry-Williams et al. | |
| 8,729,018 B2 * | 5/2014 | Chilkoti | 514/11.7 |

FOREIGN PATENT DOCUMENTS

| | | |
|---|---|---|
| DE | 3218121 | 11/1983 |
| EP | 88046 | 9/1973 |
| EP | 36676 | 9/1981 |
| EP | 52322 | 5/1982 |
| EP | 58481 | 8/1982 |
| EP | 102324 | 3/1984 |
| EP | 133988 | 3/1985 |
| EP | 142641 | 5/1985 |
| EP | 143949 | 6/1985 |
| EP | 201 239 | 11/1986 |
| EP | 251 744 | 1/1988 |
| EP | 258 067 | 3/1988 |
| EP | 322 094 | 6/1989 |
| EP | 330 451 | 8/1989 |
| EP | 361 991 | 4/1990 |
| EP | 387 319 | 9/1990 |
| EP | 401 384 | 12/1990 |
| EP | 693 554 | 1/1996 |
| JP | 62-096086 | 5/1987 |
| WO | WO 86/05807 | 10/1986 |
| WO | WO 87/04462 | 7/1987 |
| WO | WO 89/01036 | 2/1989 |
| WO | WO 89/10404 | 11/1989 |
| WO | WO 90/01063 | 2/1990 |

(Continued)

OTHER PUBLICATIONS

Kristensen et al., Biochem. J., 1995, vol. 305:981-986.*
Lee et al., Nature, 2000, vol. 408:483-488.*
Duttaroy et al., Diabetes, Jan. 2005, vol. 54:251-258.*
Liu et al., J. Biol. Chem., 2003, vol. 278:14798-14805.*
Kristensen et al., Biochem. J. 1995, vol. 305:981-986.*
Bebbington et al., Bio/Technology 10, pp. 169-175 (1992).
Biblia et al., Biotechnol. Prog., 11, p. 1-13 (1995).
Bowie et al., Deciphering the Message in Protein Sequences: Tolerance to Amino Acid Substitutions, Science, 247, pp. 1306-1310 (1990).
Brutlag et al., (Comp. App. Biosci. 6, pp. 237-245 (1990).
Caliceti et al., Bioconjug. Chem., 10, pp. 638-646 (1999).
Cleland et al., Crit. Ref. Therapeutic Drug Carrier Systems, 10, pp. 307-377 (1993).

(Continued)

*Primary Examiner* — Xiaozhen Xie
(74) *Attorney, Agent, or Firm* — Foley & Lardner LLP

(57) ABSTRACT

Disclosed are fusion proteins that include albumin fused to a polypeptide that has insulin activity. The fusion proteins may include albumin fused to insulin or an insulin analog. In particular, the fusions proteins may include albumin fused to a single chain insulin analog. The fusion proteins may exhibit extended insulin activity in vivo or in vitro relative to insulin that is not fused to albumin. The fusion proteins may be formulated as aerosol compositions.

**33 Claims, 21 Dr

(56) References Cited

FOREIGN PATENT DOCUMENTS

| WO | WO 91/06657 | | 5/1991 |
|---|---|---|---|
| WO | WO 94/12650 | | 6/1994 |
| WO | WO 95/23857 | | 9/1995 |
| WO | WO 96/06058 | | 2/1996 |
| WO | WO 96/29411 | | 9/1996 |
| WO | WO 96/34891 | | 11/1996 |
| WO | WO 97/24445 | | 7/1997 |
| WO | WO 97/33899 | | 9/1997 |
| WO | WO 97/34911 | | 9/1997 |
| WO | WO 98/32466 | | 7/1998 |
| WO | WO 99/00504 | | 1/1999 |
| WO | WO 99/23105 | | 5/1999 |
| WO | WO 00/44772 | | 8/2000 |
| WO | WO 03/059934 | | 7/2003 |
| WO | WO 03/060071 | A2 | 7/2003 |
| WO | WO 03/059934 | * | 7/2013 |

OTHER PUBLICATIONS

Cunningham et al., Science, 244, pp. 1081-1085 (1989).
Delgado et al., Crit. Rev. Thera. Drug Carrier Sys., 9, pp. 249-304 (1992).
DeNardo et al., Clin. Cancer Res., 4(10), pp. 2483-2490 (1998).
Dobeli et al., J. Biotechnology 7, pp. 199-216 (1988).
Francis et al., Intern. J. of Hematol., 68, 1-18 (1998).
Koller et al., Proc. Natl. Acad. Sci. USA, 86, pp. 8932-8935 (1989).
Malik et al., Exp. Hematol., 20, pp. 1028-1035 (1992).
Morpurgo et al., Appl. Biochem. Biotechnol., 56, pp. 59-72 (1996).
Peterson et al., Bioconjug. Chem., 10(4), pp. 553-557 (1999).
Pinckard et al., Clin. Exp. Immunol., 2, pp. 331-340 (1967).
Robbins et al., Diabetes, 36, pp. 838-845 (1987).
Ron et al., J. Biol. Chem., 268, pp. 2984-2988 (1993).
Vorobjev et al., Nucleosides Nucleotides, 18, pp. 2745-2750 (1999).
Wilson et al., Cell 37, p. 767-778 (1984).
Zijlstra et al., Nature, 342, pp. 435-438 (1989).
Zimmerman et al., Nucl. Med. Biol., 26(8), pp. 943-950 (1999).
International Search Report for PCT/US2007/075361 completed Oct. 9, 2008, 2 pgs.
Written Opinion of the International Searching Authority for PCT/US2007/075361 completed Oct. 9, 2008, 9 pgs.
International Preliminary Report on Patentability for PCT/US2007/075361 issued Feb. 10, 2009, 5 pgs.
Lee et al., "Remission in Models of Type 1 Diabetes by Gene Therapy Using a Single-Chain Insulin Analogue," *Nature*, vol. 408, pp. 483-488 (2000).
Duttaroy et al., "Development of a Long-Acting Insulin Analog Using Albumin Fusion Technology," *Diabetes*, vol. 54, pp. 251-258 (2005).
Kristensen et al., "A Single-Chain Insulin-Like Growth Factor I/Insulin Hybrid Binds with High Affinity to the Insulin Receptor," *Biochem. J.*, pp. 305, pp. 981-986 (1995).
Thibaudeau et al., "Synthesis and Evaluation of Insulin-Human Serum Albumin Conjugates," *Bioconjugate Chem.*, pp. 1000-1008 (2005).
Alt et al., J. Biol. Chem. 253, pp. 1357-1370 (1978).
Amoah, J. Animal Science 75(2) pp. 578-585 (1997).
Becker et al., Methods Enzymol. 194, pp. 182-187 (1990).
Berent et al., Biotech., 3, pp. 208-220 (1985).
Boshart et al., Cell, 41, pp. 521-530 (1985).
Brenin et al., Surg. Oncol. 6(2), pp. 99-110 (1997).
Campbell et al., Nature, 380, pp. 64-66 (1996).
Carver et al., Biotechnology (NY) 11, pp. 1263-1270 (1993).
Clark et al., BioTechnology 7, pp. 487-492 (1989).
Clutter et al., Genetics 143 (4), pp. 1753-1760, (1996).
Cockell et al., Mol. Cell. Biol. 9, pp. 2464-2476 (1989).
Cullin et al., Molecular and Cellular Biology, pp. 438-447 (1985).
DiTullio, BioTechnology 10, pp. 74-77, (1992).
Ellis et al., Mol. Cell. Biol. 5, pp. 1111-1121 (1985).
Eppstein et al., Proc. Natl. Acad. Sci (USA) 82, pp. 3688-3692 (1985).
Fromont-Racine et al., Nucleic Acids Res., 21(7), pp. 1683-1684 (1993).
Gayle et al., J. Biol. Chem., 268, pp. 22105-22111 (1993).
Gleeson et al., J. Gen. Microbiol., 132, pp. 3459-3465 (1986).
Gonda, Critical Reviews in Therapeutic Drug Carrier Systems, 6, pp. 273-313 (1990).
Goodson, Medical Applications of Controlled Release, supra, vol. 2, pp. 115-138 (1984).
Gordon, Thransgenic Animals, Intl. Rev. Cytol. 115, pp. 171-229 (1989).
Gorton et al., BioTechnology 5, pp. 1183-1187 (1987).
Gu et al., Science, 265, pp. 103-106 (1994).
Hamlin et al., Biochem., et Biophys. Acta., 1097, pp. 107-143 (1990).
Haspel et al., J. Membr. Biol., 169(1), pp. 45-53 (1999).
Henikoff et al., Proc. Natl. Acad. Sci. USA 89, pp. 10915-10919 (1992).
Hoffman et al., Genetics 124, pp. 807-816 (1990).
Houdebine, Reprod. Nutr. Dev. 35(6), pp. 609-617 (1995).
Howard et al., J. Neurosurg., 71, p. 105 (1989).
Hui et al., Diabetes, 50(4), pp. 785-796 (2001).
Hunkapiller et al., Nature, 310, pp. 105-111 (1984).
Hwang et al., Proc. Natl. Acad. Sci. (USA) 77, pp. 4030-4034 (1980).
Jessop et al., Characteristics of two rat pancreatic exocrine cell lines derived from transplantable tumors, in Vitro 16, p. 212 (1980).
Kerry-Williams et al., Yeast 14, pp. 161-169 (1998).
Kim et al., Mol. Reprod. Dev. 46(4), pp. 515-526 (1997).
Koutz et al., Yeast, 5, pp. 167-177 (1989).
Langer et al., J. Biomed. Mater. Res. 15, pp. 167-277 (1981).
Langer, Chem. Tech. 12, pp. 98-105 (1982).
Langer, Science, 249, pp. 1527-1533 (1990).
Langer et al., J. Macromol. Sci. Rev. Macromol. Chem. 23, p. 61-126 (1983).
Lasko et al., Proc. Natl. Acad. Sci. USA 89, pp. 6232-6236 (1992).
Lavitrano et al., Cell, 57 pp. 717-723 (1989).
Levy et al., Science, 228, pp. 190-192 (1985).
Lo, Mol. Cell. Biol. 3, pp. 1803-1814 (1983).
Maundrell, J. Biol. Chem., 265, pp. 10857-10864 (1990).
McCarthy, The Lancet 349(9049), p. 405 (1997).
Mullins et al., Hypertension 22(4), pp. 630-633 (1993).
Mumberg et al., Nucleic Acids Research, vol. 22, No. 25, pp. 5767-5768 (1994).
Murphy et al., Biochem J., 227, pp. 277-279 (1991).
Page et al., Biotechnology 9, pp. 64-68 (1991).
Paterson et al., Appl. Microbiol. Biotechnol., 40, pp. 691-698 (1994).
Petters, Reprod. Fertil. Dev. 6(5), pp. 643-645 (1994).
Poznansky et al., FEBS Lett., 239, p. 18 (1988).
Raebum et al., Pharmacol. Toxicol. Methods 27, pp. 143-159 (1992).
Rattan et al., Ann. N.Y. Acad. Sci., 663, pp. 48-62 (1992).
Roux et al., The cell-specific transcription factor PTF1 contains two different subunits that interact with the DNA, Genes Dev. 3, pp. 1613-1624 (1989).
Saiki et al., Science, 239, pp. 487-491 (1988).
Schnieke et al., Science 278 (5346), pp. 2130-2133 (1997).
Sefton, CRC Crit. Ref. Biomed. Eng., 14, pp. 201-240 (1987).
Sidman et al., Biopolymers 22, pp. 547-556 (1983).
Sleep et al., Biotechnology 8, p. 42-46 (1990).
Soulier et al., FEBS Letts. 297, pp. 13-18 (1992).
Southern, J. Mol. Biol. 98, pp. 503-517 (1975).
Stephen and Cockett, Nucl. Acids. Res. 17, p. 7110 (1989).
Thompson et al., Cell 56, pp. 313-321 (1989).
Tsakiridis et al., Endocrinology, 136(10), pp. 4315-4322 (1995).
Tschopp et al., Nucl. Acids. Res., 15, pp. 3859-3876 (1987).
Ulmer et al., Science, 259, p. 17451749 (1993).
Urso et al., J. Biol. Chem., 274(43), pp. 30864-30873 (1999).
Van der Putten et al., Proc. Natl. Acad. Sci., USA, 82, pp. 6148-6152 (1985).
Wang et al., J. Mol. Endocrinol, 19(3), pp. 241-248 (1997).
Wilmut et al., Nature, 385, pp. 810-813 (1997).
Wright et al., Biotechnology (NY) 9, pp. 830-834 (1991).

(56) References Cited

OTHER PUBLICATIONS

Altschul et al., Issues in Searching Molecular Sequence Databases, *Nature Genetics* 6, pp. 119-129 (1994).
Altschul, "A Protein Alignment Scoring System Sensitive at All Evolutionary Distances," *J. Mol. Evol.* 36, pp. 290-300 (1993).
Ausubel et al., Current protocol in Molecular Biology, Green Publishing Associates, Inc., and John Wiley & Sons, Inc., NY, pp. 6.3.1-6.3.6, and 2.10.3 (1989).
Johnson, "Posttranslational Protein Modifications: Perspective and Prospectives,", *Ed., Academic Press*, NY, pp. 1-12 (1983).
Buchwald et al., "Long-term, Continuous Intravenous Heparin Administration by an Implantable Infusion Pump in Ambulatory Patients with Recurrent Venous Thrombosis," *Surgery* 88, p. 507 (1980).
During et al., "Controlled Release of Dopamine from a Polymeric Brain Implant: In Vivo Characterization," *Ann. Neurol.*, 25, p. 351 (1989).
Gentz et al., "Bioassay for Trans-Activation Using Purified Human Immunodeficiency Virus tat-encoded protein: Trans-activation requires mRNA Synthesis," *Proc. Natl. Acad. Sci. USA* 86, pp. 821-824 (1989).
Phizicky et al., Protein-Protein Interations: Methods for Detection and Analysis, *Microbiol. Rev.*, 59, pp. 94-123 (1995).
Saudek et al., "A Preliminary Trial of the Programmable Implantable Medication System for Insulin Delivery," *N. Engl. J. Med.*, 321, p. 574 (1989).
Seifter et al., "Analysis for Protein Modifications and Nonprotein Cofactors," *Meth. Enzymol.* 182, pp. 626-646 (1990).
Takahashi et al., "Human Fas Ligand: Gene Structure, Chromosomal Location and Species Specificity," *Int. Immunol.*, 6, pp. 1567-1574 (1994).
Treat et al., Liposomes in the Therapy of Infections Disease and Cancer, pp. 353-365 (1989).
Office Communication issued in related European Patent Application No. 07813842.7, dated Dec. 15, 2014.

\* cited by examiner

FIGURE 1A

```
  1 GAT GCA CAC AAG AGT GAG GTT GCT CAT CGG TTT AAA GAT TTG GGA GAA GAA AAT TTC AAA  60
  1 D   A   H   K   S   E   V   A   H   R   F   K   D   L   G   E   E   N   F   K    20

61 GCC TTG GTG TTG ATT GCC TTT GCT CAG TAT CTT CAG CAG TGT CCA TTT GAA GAT CAT GTA 120
 21 A   L   V   L   I   A   F   A   Q   Y   L   Q   Q   C   P   F   E   D   H   V    40

121 AAA TTA GTG AAT GAA GTA ACT GAA TTT GCA AAA ACA TGT GTT GCT GAT GAG TCA GCT GAA 180
 41 K   L   V   N   E   V   T   E   F   A   K   T   C   V   A   D   E   S   A   E    60

181 AAT TGT GAC AAA TCA CTT CAT ACC CTT TTT GGA GAC AAA TTA TGC ACA GTT GCA ACT CTT 240
 61 N   C   D   K   S   L   H   T   L   F   G   D   K   L   C   T   V   A   T   L    80

241 CGT GAA ACC TAT GGT GAA ATG GCT GAC TGC TGT GCA AAA CAA GAA CCT GAG AGA AAT GAA 300
 81 R   E   T   Y   G   E   M   A   D   C   C   A   K   Q   E   P   E   R   N   E   100

301 TGC TTC TTG CAA CAC AAA GAT GAC AAC CCA AAC CTC CCC CGA TTG GTG AGA CCA GAG GTT 360
101 C   F   L   Q   H   K   D   D   N   P   N   L   P   R   L   V   R   P   E   V   120

361 GAT GTG ATG TGC ACT GCT TTT CAT GAC AAT GAA GAG ACA TTT TTG AAA AAA TAC TTA TAT 420
121 D   V   M   C   T   A   F   H   D   N   E   E   T   F   L   K   K   Y   L   Y   140

421 GAA ATT GCC AGA AGA CAT CCT TAC TTT TAT GCC CCG GAA CTC CTT TTC TTT GCT AAA AGG 480
141 E   I   A   R   R   H   P   Y   F   Y   A   P   E   L   L   F   F   A   K   R   160
```

FIGURE 1B

```
481 TAT AAA GCT GCT TTT ACA GAA TGT TGC CAA GCT GCT GAT AAA GCT GCC TGC CTG TTG CCA 540
161  Y   K   A   A   F   T   E   C   C   Q   A   A   D   K   A   A   C   L   L   P  180

541 AAG CTC GAT GAA CTT CGG GAT GAA GGG AAG GCT TCG TCT GCC AAA CAG AGA CTC AAA TGT 600
181  K   L   D   E   L   R   D   E   G   K   A   S   S   A   K   Q   R   L   K   C  200

601 GCC AGT CTC CAA AAA TTT GGA GAA AGA GCT TTC AAA GCA TGG GCA GTG GCT CGC CTG AGC 660
201  A   S   L   Q   K   F   G   E   R   A   F   K   A   W   A   V   A   R   L   S  220

661 CAG AGA TTT CCC AAA GCT GAG TTT GCA GAA GTT TCC AAG TTA GTG ACA GAT CTT ACC AAA 720
221  Q   R   F   P   K   A   E   F   A   E   V   S   K   L   V   T   D   L   T   K  240

721 GTC CAC ACG GAA TGC TGC CAT GGA GAT CTG CTT GAA TGT GCT GAT GAC AGG GCG GAC CTT 780
241  V   H   T   E   C   C   H   G   D   L   L   E   C   A   D   D   R   A   D   L  260

781 GCC AAG TAT ATC TGT GAA AAT CAG GAT TCG ATC TCC AGT AAA CTG AAG GAA TGC TGT GAA 840
261  A   K   Y   I   C   E   N   Q   D   S   I   S   S   K   L   K   E   C   C   E  280

841 AAA CCT CTG TTG GAA AAA TCC CAC TGC ATT GCC GAA GTG GAA AAT GAT GAG ATG CCT GCT 900
281  K   P   L   L   E   K   S   H   C   I   A   E   V   E   N   D   E   M   P   A  300

901 GAC TTG CCT TCA TTA GCT GCT GAT TTT GTT GAA AGT AAG GAT GTT TGC AAA AAC TAT GCT 960
301  D   L   P   S   L   A   A   D   F   V   E   S   K   D   V   C   K   N   Y   A  320
```

FIGURE 1C

```
 961 GAG GCA AAG GAT GTC TTC CTG GGC ATG TTT TTG TAT GAA TAT GCA AGA AGG CAT CCT GAT 1020
 321 E   A   K   D   V   F   L   G   M   F   L   Y   E   Y   A   R   R   H   P   D   340

1021 TAC TCT GTC GTG CTG CTG CTG AGA CTT GCC AAG ACA TAT GAA ACC ACT CTA GAG AAG TGC 1080
 341 Y   S   V   V   L   L   L   R   L   A   K   T   Y   E   T   T   L   E   K   C   360

1081 TGT GCC GCT GCA GAT CCT CAT GAA TGC TAT GCC AAA GTG TTC GAT GAA TTT AAA CCT CTT 1140
 361 C   A   A   A   D   P   H   E   C   Y   A   K   V   F   D   E   F   K   P   L   380

1141 GTG GAA GAG CCT CAG AAT TTA ATC AAA CAA AAC TGT GAG CTT TTT GAG CAG CTT GGA GAG 1200
 381 V   E   E   P   Q   N   L   I   K   Q   N   C   E   L   F   E   Q   L   G   E   400

1201 TAC AAA TTC CAG AAT GCG CTA TTA GTT CGT TAC ACC AAG AAA GTA CCC CAA GTG TCA ACT 1260
 401 Y   K   F   Q   N   A   L   L   V   R   Y   T   K   K   V   P   Q   V   S   T   420

1261 CCA ACT CTT GTA GAG GTC TCA AGA AAC CTA GGA AAA GTG GGC AGC AAA TGT TGT AAA CAT 1320
 421 P   T   L   V   E   V   S   R   N   L   G   K   V   G   S   K   C   C   K   H   440

1321 CCT GAA GCA AAA AGA ATG CCC TGT GCA GAA GAC TAT CTA TCC GTG GTC CTG AAC CAG TTA 1380
 441 P   E   A   K   R   M   P   C   A   E   D   Y   L   S   V   V   L   N   Q   L   460

1381 TGT GTG TTG CAT GAG AAA ACG CCA GTA AGT GAC AGA GTC ACA AAA TGC TGC ACA GAG TCC 1440
 461 C   V   L   H   E   K   T   P   V   S   D   R   V   T   K   C   C   T   E   S   480
```

FIGURE 1D

```
1441 TTG GTG AAC AGG CGA CCA TGC TTT TCA GCT CTG GAA GTC GAT GAA ACA TAC GTT CCC AAA 1500
481  L   V   N   R   R   P   C   F   S   A   L   E   V   D   E   T   Y   V   P   K   500

1501 GAG TTT AAT GCT GAA ACA TTC ACC TTC CAT GCA GAT ATA TGC ACA CTT TCT GAG AAG GAG 1560
501  E   F   N   A   E   T   F   T   F   H   A   D   I   C   T   L   S   E   K   E   520

1561 AGA CAA ATC AAG AAA CAA ACT GCA CTT GTT GAG CTT GTG AAA CAC AAG CCC AAG GCA ACA 1620
521  R   Q   I   K   K   Q   T   A   L   V   E   L   V   K   H   K   P   K   A   T   540

1621 AAA GAG CAA CTG AAA GCT GTT ATG GAT GAT TTC GCA GCT TTT GTA GAG AAG TGC TGC AAG 1680
541  K   E   Q   L   K   A   V   M   D   D   F   A   A   F   V   E   K   C   C   K   560

1681 GCT GAC GAT AAG GAG ACC TGC TTT GCC GAG GAG GGT AAA AAA CTT GTT GCT GCA AGT CAA 1740
561  A   D   D   K   E   T   C   F   A   E   E   G   K   K   L   V   A   A   S   Q   580

1741 GCT GCC TTA GGC TTA TAA CAT CTA CAT TTA AAA GCA TCT CAG 1782
581  A   A   L   G   L   *                                   585
```

FIGURE 15
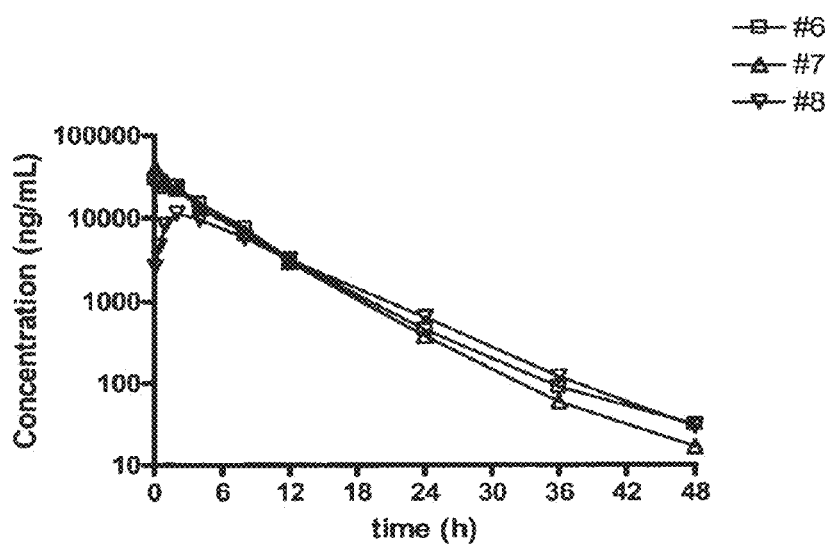
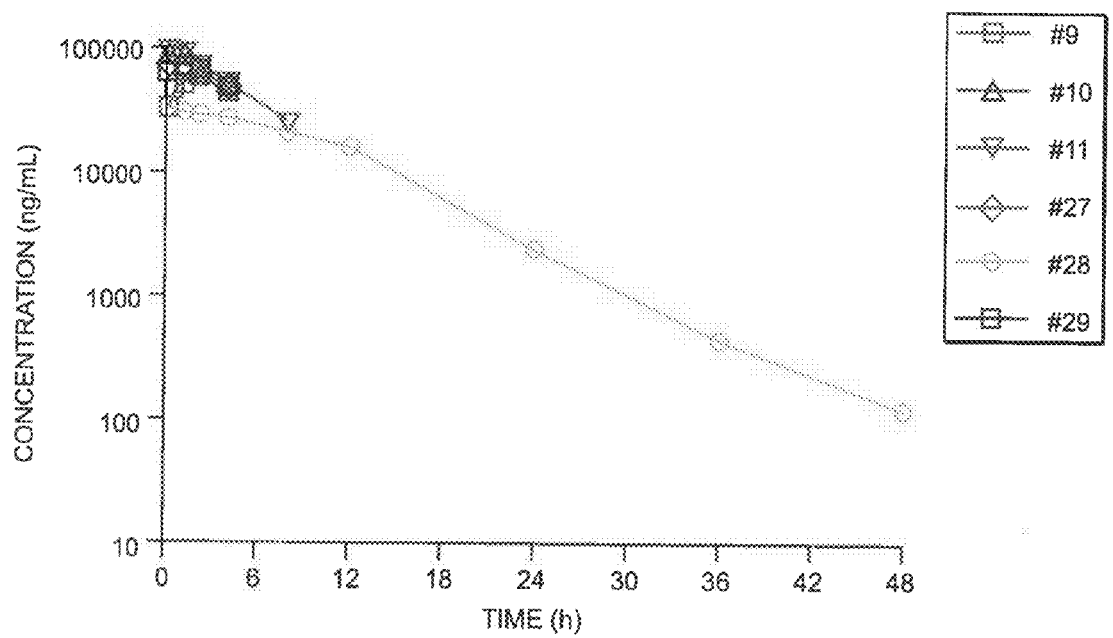
FIGURE 16

SEQUENCE LISTING

<160> NUMBER OF SEQ ID NOS: 77

<210> SEQ ID NO 1
<211> LENGTH: 35
<212> TYPE: PRT
<213> ORGANISM: Homo sapiens

<400> SEQUENCE: 1

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 2
<211> LENGTH: 12
<212> TYPE: PRT
<213> ORGANISM: Homo sapiens

<400> SEQUENCE: 2

Gly Tyr Gly Ser Ser Ser Arg Arg Ala Pro Gln Thr
1               5                   10

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Lys Trp Val Ser Phe Ile Ser Leu Leu Phe Leu Phe Ser Ser Ala
1               5                   10                  15

Tyr Ser Arg Ser Leu Glu Lys Arg
            20

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Lys Trp Val Ser Phe Ile Ser Leu Leu Phe Leu Phe Ser Ser Ala
1               5                   10                  15

Tyr Ser Arg Ser Leu Asp Lys Arg
            20

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Asn Ile Phe Tyr Ile Phe Leu Phe Leu Leu Ser Phe Val Gln Gly
1               5                   10                  15

Ser Leu Asp Lys Arg

-continued

```
                20

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Lys Trp Val Ser Phe Ile Ser Leu Leu Phe Leu Phe Ser Ser Ala
1               5                   10                  15

Tyr Ser Arg Gly Val Phe Arg Arg
            20

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Lys Trp Val Thr Phe Ile Ser Leu Leu Phe Leu Phe Ala Gly Val
1               5                   10                  15

Leu Gly

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Lys Trp Val Thr Phe Ile Ser Leu Leu Phe Leu Phe Ser Gly Val
1               5                   10                  15

Leu Gly

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Lys Trp Val Thr Phe Ile Ser Leu Leu Phe Leu Phe Gly Gly Val
1               5                   10                  15

Leu Gly

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Lys Trp Val Thr Phe Ile Ser Leu Leu Phe Leu Phe Ala Gly Val
```

-continued

```
1               5                   10                  15
Ser Gly

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Lys Trp Val Thr Phe Ile Ser Leu Leu Phe Leu Phe Gly Gly Val
1               5                   10                  15

Ser Gly

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Lys Trp Val Thr Phe Ile Ser Leu Leu Phe Leu Phe Ser Gly Val
1               5                   10                  15

Ser Gly

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Met Lys Trp Val Thr Phe Leu Ser Leu Leu Phe Leu Phe Gly Gly Val
1               5                   10                  15

Ser Gly

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Lys Trp Val Thr Phe Ile Ser Leu Leu Phe Leu Phe Gly Gly Val
1               5                   10                  15

Leu Gly Asp Leu His Lys Ser
            20

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Met Pro Thr Trp Ala Trp Trp Leu Phe Leu Val Leu Leu Ala Leu
1               5                   10                  15

Trp Ala Pro Ala Arg Gly
            20

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Asn Ile Phe Tyr Ile Phe Leu Phe Leu Leu Ser Phe Val Gln Gly
1               5                   10                  15

Leu Glu His Thr His Arg Arg Gly Ser Leu Asp Lys Arg
            20                  25

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Lys Leu Ala Tyr Ser Leu Leu Leu Pro Leu Ala Gly Val Ser Ala
1               5                   10                  15

Ser Val Ile Asn Tyr Lys Arg
            20

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Pro Asn Leu Pro Arg Leu Val Arg
1               5

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Asp Asp Asn Pro Asn Leu Pro Arg Leu Val Arg
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

-continued

```
Asn Asp Glu Met Pro Ala Asp
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Pro Gln Thr
1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ala Gly Ser Ser Ser Arg Arg Ala Pro Gln Thr
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Pro Gly Ala Gly
1               5

<210> SEQ ID NO 24
<211> LENGTH: 110
<212> TYPE: PRT
<213> ORGANISM: Homo sapiens

<400> SEQUENCE: 24

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 25
<211> LENGTH: 30
<212> TYPE: PRT
```

```
<213> ORGANISM: Homo sapiens

<400> SEQUENCE: 25

Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Thr
            20                  25                  30

<210> SEQ ID NO 26
<211> LENGTH: 21
<212> TYPE: PRT
<213> ORGANISM: Homo sapiens

<400> SEQUENCE: 26

Gly Ile Val Glu Gln Cys Cys Thr Ser Ile Cys Ser Leu Tyr Gln Leu
1               5                   10                  15
Glu Asn Tyr Cys Asn
            20

<210> SEQ ID NO 27
<211> LENGTH: 35
<212> TYPE: PRT
<213> ORGANISM: Homo sapiens

<400> SEQUENCE: 27

Arg Arg Glu Ala Glu Asp Leu Gln Val Gly Gln Val Glu Leu Gly Gly
1               5                   10                  15
Gly Pro Gly Ala Gly Ser Leu Gln Pro Leu Ala Leu Glu Gly Ser Leu
            20                  25                  30
Gln Lys Arg
        35

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Leu Asp Lys Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Pro Gly Lys Arg
1               5

<210> SEQ ID NO 30
<211> LENGTH: 394
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
```

-continued

```
gcggccgccg gatgcaaggg ttcgaatccc ttagctctca ttattttttg cttttctct      60 tgaggtcaca tgatcgcaaa atggcaaatg gcacgtgaag ctgtcgatat tggggaactg    120
tggtggttgg caaatgacta attaagttag tcaaggcgcc atcctcatga aaactgtgta    180
acataataac cgaagtgtcg aaaaggtggc accttgtcca attgaacacg ctcgatgaaa    240
aaaataagat atatataagg ttaagtaaag cgtctgttag aaaggaagtt tttcctttt    300 cttgctctct tgtcttttca tctactattt ccttcgtgta atacagggtc gtcagataca    360
tagatacaat tctattaccc ccatccatac aatg                                394
```

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Lys Val Ser Val Ala Ala Leu Ser Cys Leu Met Leu Val Thr Ala
1               5                   10                  15

Leu Gly Ser Gln Ala
            20

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Leu Gln Asn Ser Ala Val Leu Leu Leu Leu Val Ile Ser Ala Ser
1               5                   10                  15

Ala

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Lys Trp Val Thr Phe Ile Ser Leu Leu Phe Leu Phe Ser Ser Ala
1               5                   10                  15

Tyr Ser

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Lys Trp Val Ser Phe Ile Ser Leu Leu Phe Leu Phe Ser Ser Ala
1               5                   10                  15

Tyr Ser

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Leu Leu Gln Ala Phe Leu Phe Leu Leu Ala Gly Phe Ala Ala Lys
1               5                   10                  15

Ile Ser Ala

<210> SEQ ID NO 37
<211> LENGTH: 86
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Arg Phe Pro Ser Ile Phe Thr Ala Val Leu Ala Phe Ala Ala Ser
1               5                   10                  15

Ser Ala Leu Ala Ala Pro Val Asn Thr Thr Thr Glu Asp Glu Thr Ala
                20                  25                  30

Gln Ile Pro Ala Glu Ala Val Ile Gly Tyr Ser Asp Leu Glu Gly Asp
            35                  40                  45

Phe Asp Val Ala Val Leu Pro Phe Ser Asn Ser Thr Asn Asn Gly Leu
    50                  55                  60

Leu Phe Ile Asn Thr Thr Ile Ala Ser Ile Ala Ala Lys Glu Glu Gly
65                  70                  75                  80

Val Ser Leu Glu Lys Arg
                85

<210> SEQ ID NO 38
<211> LENGTH: 86
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Arg Phe Pro Ser Ile Phe Thr Ala Val Leu Ala Phe Ala Ala Ser
1               5                   10                  15

Ser Ala Leu Ala Ala Pro Val Asn Thr Thr Thr Glu Asp Glu Thr Ala
                20                  25                  30

```
Gln Ile Pro Ala Glu Ala Val Ile Gly Tyr Ser Asp Leu Glu Gly Asp
         35                  40                  45

Phe Asp Val Ala Val Leu Pro Phe Ser Asn Ser Thr Asn Asn Gly Leu
 50                  55                  60

Leu Phe Ile Asn Thr Thr Ile Ala Ser Ile Ala Ala Lys Glu Glu Gly
 65                  70                  75                  80

Val Ser Leu Asp Lys Arg
                 85

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Met Gly Trp Ser Cys Ile Ile Leu Phe Leu Val Ala Thr Ala Thr Gly
 1               5                  10                  15

Val His Ser

<210> SEQ ID NO 40
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met Glu Arg Ala Ala Pro Ser Arg Arg Val Pro Leu Pro Leu Leu Leu
 1               5                  10                  15

Leu Gly Gly Leu Ala Leu Leu Ala Ala Gly Val Asp Ala
             20                  25

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Met Lys Thr Leu Leu Leu Phe Val Gly Leu Leu Leu Thr Trp Glu
 1               5                  10                  15

Ser Gly Gln Val Leu Gly
             20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Met Leu Pro Leu Cys Leu Val Ala Ala Leu Leu Leu Ala Ala Gly Pro
 1               5                  10                  15

Gly Pro Ser Leu Gly
             20
```

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Phe Lys Ser Val Val Tyr Ser Ile Leu Ala Ala Ser Leu Ala Asn
1               5                   10                  15

Ala

<210> SEQ ID NO 44
<211> LENGTH: 65
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Lys Leu Lys Thr Val Arg Ser Ala Val Leu Ser Ser Leu Phe Ala
1               5                   10                  15

Ser Gln Val Leu Gly Gln Pro Ile Asp Asp Thr Glu Ser Gln Thr Thr
            20                  25                  30

Ser Val Asn Leu Met Ala Asp Asp Thr Glu Ser Ala Glu Ala Thr Gln
        35                  40                  45

Thr Asn Ser Gly Gly Leu Asp Val Val Gly Leu Ile Ser Met Ala Lys
    50                  55                  60

Arg
65

<210> SEQ ID NO 45
<211> LENGTH: 70
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Met Lys Leu Lys Thr Val Arg Ser Ala Val Leu Ser Ser Leu Phe Ala
1               5                   10                  15

Ser Gln Val Leu Gly Gln Pro Ile Asp Asp Thr Glu Ser Gln Thr Thr
            20                  25                  30

Ser Val Asn Leu Met Ala Asp Asp Thr Glu Ser Ala Phe Ala Thr Gln
        35                  40                  45

Thr Asn Ser Gly Gly Leu Asp Val Val Gly Leu Ile Ser Met Ala Glu
    50                  55                  60

Glu Gly Glu Pro Lys Arg
65                  70

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Met Leu Gln Asn Ser Ala Val Leu Leu Ile Leu Leu Val Ile Ser Ala
1               5                   10                  15

Ser Ala

<210> SEQ ID NO 47
<211> LENGTH: 86
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Met Arg Phe Pro Ser Ile Phe Thr Ala Val Leu Ala Phe Ala Ala Ser
1               5                   10                  15

Ser Ala Leu Ala Ala Pro Val Asn Thr Thr Glu Asp Glu Thr Ala
            20                  25                  30

Gln Ile Pro Ala Glu Ala Val Ile Gly Tyr Ser Asp Leu Glu Gly Asp
        35                  40                  45

Phe Asp Val Ala Val Leu Pro Phe Ser Asn Ser Thr Asn Asn Gly Leu
    50                  55                  60

Leu Phe Ile Asn Thr Thr Ile Ala Ser Ile Ala Ala Lys Glu Glu Gly
65                  70                  75                  80

Val Ser Leu Glu Lys Arg
                85

<210> SEQ ID NO 48
<211> LENGTH: 86
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Arg Phe Pro Ser Ile Phe Thr Ala Val Leu Ala Phe Ala Ala Ser
1               5                   10                  15

Ser Ala Leu Ala Ala Pro Val Asn Thr Thr Glu Asp Glu Thr Ala
            20                  25                  30

Gln Ile Pro Ala Glu Ala Val Ile Gly Tyr Ser Asp Leu Glu Gly Asp
        35                  40                  45

Phe Asp Val Ala Val Leu Pro Phe Ser Asn Ser Thr Asn Asn Gly Leu
    50                  55                  60

Leu Phe Ile Asn Thr Thr Ile Ala Ser Ile Ala Ala Lys Glu Glu Gly
65                  70                  75                  80

Val Ser Leu Asp Lys Arg
                85

<210> SEQ ID NO 49
<211> LENGTH: 65
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Lys Leu Lys Thr Val Arg Ser Ala Val Leu Ser Ser Leu Phe Ala
1               5                   10                  15

Ser Gln Val Leu Gly Gln Pro Ile Asp Asp Thr Glu Ser Gln Thr Thr
```

```
                20                  25                  30
Ser Val Asn Leu Met Ala Asp Asp Thr Glu Ser Ala Phe Ala Thr Gln
            35                  40                  45

Thr Asn Ser Gly Gly Leu Asp Val Val Gly Leu Ile Ser Met Ala Lys
        50                  55                  60

Arg
65

<210> SEQ ID NO 50
<211> LENGTH: 70
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Lys Leu Lys Thr Val Arg Ser Ala Val Leu Ser Ser Leu Phe Ala
1               5                  10                  15

Ser Gln Val Leu Gly Gln Pro Ile Asp Asp Thr Glu Ser Gln Thr Thr
            20                  25                  30

Ser Val Asn Leu Met Ala Asp Asp Thr Glu Ser Ala Phe Ala Thr Gln
        35                  40                  45

Thr Asn Ser Gly Gly Leu Asp Val Val Gly Leu Ile Ser Met Ala Glu
    50                  55                  60

Glu Gly Glu Pro Lys Arg
65                  70

<210> SEQ ID NO 51
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gcctcgagaa aagagatgca cacaagagtg aggttgctca tcgatttaaa gatttggg      58

<210> SEQ ID NO 52
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aatcgatgag caacctcact cttgtgtgca tctcttttct cgaggctcct ggaataagc     59

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tacaaactta agagtccaat tagc                                           24

<210> SEQ ID NO 54
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cacttctcta gagtggtttc atatgtctt                                            29

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Asp Lys Arg
1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Glu Lys Arg
1

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aagctgcctt aggcttataa taaggcgcgc cggccggccg tttaaactaa gcttaattct         60

<210> SEQ ID NO 58
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
agaattaagc ttagtttaaa cggccggccg gcgcgcctta ttataagcct aaggcagctt         60

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(32)
<223> OTHER INFORMATION: a, c, g, t, unknown or other; area is identical
      to the first 15 nucleotides encoding the therapeutic protein of
      interest
```

<400> SEQUENCE: 59
aagctgcctt aggcttannn nnnnnnnnnn nn                                      32

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Leu Gly Leu
1

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(45)
<223> OTHER INFORMATION: a, c, g, t, unknown or other; area is identical
      to the reverse complement of the last 15 nucleotides encoding
      the therapeutic protein of interest

<400> SEQUENCE: 61
gcgcgcgttt aaacggccgg ccggcgcgcc nnnnnnnnnn nnnnn                        45

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(33)
<223> OTHER INFORMATION: a, c, g, t, unknown or other; area is identical
      to the first 15 nucleotides encoding the therapeutic protein of
      interest

<400> SEQUENCE: 62
aggagcgtcg acaaaagann nnnnnnnnnn nnn                                     33

<210> SEQ ID NO 63
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(52)
<223> OTHER INFORMATION: a, c, g, t, unknown or other; area is identical
      to the reverse complement of the last 15 nucleotides encoding
      the therapeutic protein of interest

<400> SEQUENCE: 63
ctttaaatcg atgagcaacc tcactcttgt gtgcatcnnn nnnnnnnnn nn                  52

<210> SEQ ID NO 64
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 64

Asp Ala His Lys Ser Glu Val Ala His
1               5

<210> SEQ ID NO 65
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ccgccaccat g                                                             11

<210> SEQ ID NO 66
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(46)
<223> OTHER INFORMATION: a, c, g, t, unknown or other; area designates
      DNA identical to the first 18 nucleotides encoding the therapeutic
      protein of interest

<400> SEQUENCE: 66
ccgccgctcg aggggtgtgt ttcgtcgann nnnnnnnnnn nnnnnn                        46

<210> SEQ ID NO 67
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(55)
<223> OTHER INFORMATION: a, c, g, t, unknown or other; area designates
      the reverse complement of DNA encoding the last 18 nucleotides
      encoding the therapeutic protein of interest

<400> SEQUENCE: 67
agtcccatcg atgagcaacc tcactcttgt gtgcatcnnn nnnnnnnnn nnnnn              55

<210> SEQ ID NO 68
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtcaagctgc cttaggctta ttcgttaacc aacacttgtg tggttctcac ttggttgaag        60
ctttgtactt ggtttgtggt gaa                                                83

<210> SEQ ID NO 69
<211> LENGTH: 69

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
atcgcatatg gcgcgcccta ttagttacag tagttttcca attggtacaa agaacaaata      60
gaagtacaa                                                              69

<210> SEQ ID NO 70
<211> LENGTH: 84
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tccaggagcg tcgacaaaag attcgttaac caacacttgt gtggttctca cttggttgaa      60
gctttgtact tggtttgtgg tgaa                                             84

<210> SEQ ID NO 71
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
agactttaaa tcgatgagca acctcactct tgtgtgcatc gttacagtag ttttccaatt      60
ggtacaaaga acaaatagaa gtacaa                                           86

<210> SEQ ID NO 72
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggggtacctc attggcctgg gcggcgcagc caagctgtca gcccatgtgg cgtggccgcc      60
cctcgagcgg                                                             70

<210> SEQ ID NO 73
<211> LENGTH: 1782
<212> TYPE: DNA
<213> ORGANISM: Homo sapiens
<220> FEATURE:
<221> NAME/KEY: CDS
<222> LOCATION: (1)..(1755)

<400> SEQUENCE: 73 gat gca cac aag agt gag gtt gct cat cgg ttt aaa gat ttg gga gaa       48
Asp Ala His Lys Ser Glu Val Ala His Arg Phe Lys Asp Leu Gly Glu
1               5                   10                  15 gaa aat ttc aaa gcc ttg gtg ttg att gcc ttt gct cag tat ctt cag       96
Glu Asn Phe Lys Ala Leu Val Leu Ile Ala Phe Ala Gln Tyr Leu Gln
            20                  25                  30 cag tgt cca ttt gaa gat cat gta aaa tta gtg aat gaa gta act gaa      144
Gln Cys Pro Phe Glu Asp His Val Lys Leu Val Asn Glu Val Thr Glu
        35                  40                  45
```

```
ttt gca aaa aca tgt gtt gct gat gag tca gct gaa aat tgt gac aaa    192
Phe Ala Lys Thr Cys Val Ala Asp Glu Ser Ala Glu Asn Cys Asp Lys
     50                  55                  60 tca ctt cat acc ctt ttt gga gac aaa tta tgc aca gtt gca act ctt    240
Ser Leu His Thr Leu Phe Gly Asp Lys Leu Cys Thr Val Ala Thr Leu
65                  70                  75                  80 cgt gaa acc tat ggt gaa atg gct gac tgc tgt gca aaa caa gaa cct    288
Arg Glu Thr Tyr Gly Glu Met Ala Asp Cys Cys Ala Lys Gln Glu Pro
                85                  90                  95 gag aga aat gaa tgc ttc ttg caa cac aaa gat gac aac cca aac ctc    336
Glu Arg Asn Glu Cys Phe Leu Gln His Lys Asp Asp Asn Pro Asn Leu
            100                 105                 110 ccc cga ttg gtg aga cca gag gtt gat gtg atg tgc act gct ttt cat    384
Pro Arg Leu Val Arg Pro Glu Val Asp Val Met Cys Thr Ala Phe His
        115                 120                 125 gac aat gaa gag aca ttt ttg aaa aaa tac tta tat gaa att gcc aga    432
Asp Asn Glu Glu Thr Phe Leu Lys Lys Tyr Leu Tyr Glu Ile Ala Arg
130                 135                 140 aga cat cct tac ttt tat gcc ccg gaa ctc ctt ttc ttt gct aaa agg    480
Arg His Pro Tyr Phe Tyr Ala Pro Glu Leu Leu Phe Phe Ala Lys Arg
145                 150                 155                 160 tat aaa gct gct ttt aca gaa tgt tgc caa gct gct gat aaa gct gcc    528
Tyr Lys Ala Ala Phe Thr Glu Cys Cys Gln Ala Ala Asp Lys Ala Ala
                165                 170                 175 tgc ctg ttg cca aag ctc gat gaa ctt cgg gat gaa ggg aag gct tcg    576
Cys Leu Leu Pro Lys Leu Asp Glu Leu Arg Asp Glu Gly Lys Ala Ser
            180                 185                 190 tct gcc aaa cag aga ctc aaa tgt gcc act ctc caa aaa ttt gga gaa    624
Ser Ala Lys Gln Arg Leu Lys Cys Ala Thr Leu Gln Lys Phe Gly Glu
        195                 200                 205 aga gct ttc aaa gca tgg gca gtg gct cgc ctg agc cag aga ttt ccc    672
Arg Ala Phe Lys Ala Trp Ala Val Ala Arg Leu Ser Gln Arg Phe Pro
210                 215                 220 aaa gct gag ttt gca gaa gtt tcc aag tta gtg aca gat ctt acc aaa    720
Lys Ala Glu Phe Ala Glu Val Ser Lys Leu Val Thr Asp Leu Thr Lys
225                 230                 235                 240 gtc cac acg gaa tgc tgc cat gga gat ctg ctt gaa tgt gct gat gac    768
Val His Thr Glu Cys Cys His Gly Asp Leu Leu Glu Cys Ala Asp Asp
                245                 250                 255 agg gcg gac ctt gcc aag tat atc tgt gaa aat cag gat tcg atc tcc    816
Arg Ala Asp Leu Ala Lys Tyr Ile Cys Glu Asn Gln Asp Ser Ile Ser
            260                 265                 270 agt aaa ctg aag gaa tgc tgt gaa aaa cct ctg ttg gaa aaa tcc cac    864
Ser Lys Leu Lys Glu Cys Cys Glu Lys Pro Leu Leu Glu Lys Ser His
        275                 280                 285 tgc att gcc gaa gtg gaa aat gat gag atg cct gct gac ttg cct tca    912
Cys Ile Ala Glu Val Glu Asn Asp Glu Met Pro Ala Asp Leu Pro Ser
290                 295                 300 tta gct gct gat ttt gtt gaa agt aag gat gtt tgc aaa aac tat gct    960
Leu Ala Ala Asp Phe Val Glu Ser Lys Asp Val Cys Lys Asn Tyr Ala
305                 310                 315                 320 gag gca aag gat gtc ttc ctg ggc atg ttt ttg tat gaa tat gca aga    1008
Glu Ala Lys Asp Val Phe Leu Gly Met Phe Leu Tyr Glu Tyr Ala Arg
                325                 330                 335 agg cat cct gat tac tct gtc gtg ctg ctg ctg aga ctt gcc aag aca    1056
Arg His Pro Asp Tyr Ser Val Val Leu Leu Leu Arg Leu Ala Lys Thr
            340                 345                 350 tat gaa acc act cta gag aag tgc tgt gcc gct gca gat cct cat gaa    1104
Tyr Glu Thr Thr Leu Glu Lys Cys Cys Ala Ala Ala Asp Pro His Glu
```

```
            355                 360                 365
tgc tat gcc aaa gtg ttc gat gaa ttt aaa cct ctt gtg gaa gag cct    1152
Cys Tyr Ala Lys Val Phe Asp Glu Phe Lys Pro Leu Val Glu Glu Pro
370                 375                 380 cag aat tta atc aaa caa aac tgt gag ctt ttt gag cag ctt gga gag    1200
Gln Asn Leu Ile Lys Gln Asn Cys Glu Leu Phe Glu Gln Leu Gly Glu
385                 390                 395                 400 tac aaa ttc cag aat gcg cta tta gtt cgt tac acc aag aaa gta ccc    1248
Tyr Lys Phe Gln Asn Ala Leu Leu Val Arg Tyr Thr Lys Lys Val Pro
            405                 410                 415 caa gtg tca act cca act ctt gta gag gtc tca aga aac cta gga aaa    1296
Gln Val Ser Thr Pro Thr Leu Val Glu Val Ser Arg Asn Leu Gly Lys
        420                 425                 430 gtg ggc agc aaa tgt tgt aaa cat cct gaa gca aaa aga atg ccc tgt    1344
Val Gly Ser Lys Cys Cys Lys His Pro Glu Ala Lys Arg Met Pro Cys
    435                 440                 445 gca gaa gac tat cta tcc gtg gtc ctg aac cag tta tgt gtg ttg cat    1392
Ala Glu Asp Tyr Leu Ser Val Val Leu Asn Gln Leu Cys Val Leu His
450                 455                 460 gag aaa acg cca gta agt gac aga gtc aca aaa tgc tgc aca gag tcc    1440
Glu Lys Thr Pro Val Ser Asp Arg Val Thr Lys Cys Cys Thr Glu Ser
465                 470                 475                 480 ttg gtg aac agg cga cca tgc ttt tca gct ctg gaa gtc gat gaa aca    1488
Leu Val Asn Arg Arg Pro Cys Phe Ser Ala Leu Glu Val Asp Glu Thr
            485                 490                 495 tac gtt ccc aaa gag ttt aat gct gaa aca ttc acc ttc cat gca gat    1536
Tyr Val Pro Lys Glu Phe Asn Ala Glu Thr Phe Thr Phe His Ala Asp
        500                 505                 510 ata tgc aca ctt tct gag aag gag aga caa atc aag aaa caa act gca    1584
Ile Cys Thr Leu Ser Glu Lys Glu Arg Gln Ile Lys Lys Gln Thr Ala
    515                 520                 525 ctt gtt gag ctt gtg aaa cac aag ccc aag gca aca aaa gag caa ctg    1632
Leu Val Glu Leu Val Lys His Lys Pro Lys Ala Thr Lys Glu Gln Leu
530                 535                 540 aaa gct gtt atg gat gat ttc gca gct ttt gta gag aag tgc tgc aag    1680
Lys Ala Val Met Asp Asp Phe Ala Ala Phe Val Glu Lys Cys Cys Lys
545                 550                 555                 560 gct gac gat aag gag acc tgc ttt gcc gag gag ggt aaa aaa ctt gtt    1728
Ala Asp Asp Lys Glu Thr Cys Phe Ala Glu Glu Gly Lys Lys Leu Val
            565                 570                 575 gct gca agt caa gct gcc tta ggc tta taacatctac atttaaaagc atctcag  1782
Ala Ala Ser Gln Ala Ala Leu Gly Leu
        580                 585

<210> SEQ ID NO 74
<211> LENGTH: 585
<212> TYPE: PRT
<213> ORGANISM: Homo sapiens

<400> SEQUENCE: 74

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
```

-continued

```
                65                  70                  75                  80
Arg Glu Thr Tyr Gly Glu Met Ala Asp Cys Cys Ala Lys Gln Glu Pro
                    85                  90                  95
Glu Arg Asn Glu Cys Phe Leu Gln His Lys Asp Asp Asn Pro Asn Leu
                    100                 105                 110
Pro Arg Leu Val Arg Pro Glu Val Asp Val Met Cys Thr Ala Phe His
                    115                 120                 125
Asp Asn Glu Glu Thr Phe Leu Lys Lys Tyr Leu Tyr Glu Ile Ala Arg
                    130                 135                 140
Arg His Pro Tyr Phe Tyr Ala Pro Glu Leu Leu Phe Phe Ala Lys Arg
145                     150                 155                 160
Tyr Lys Ala Ala Phe Thr Glu Cys Cys Gln Ala Ala Asp Lys Ala Ala
                        165                 170                 175
Cys Leu Leu Pro Lys Leu Asp Glu Leu Arg Asp Glu Gly Lys Ala Ser
                    180                 185                 190
Ser Ala Lys Gln Arg Leu Lys Cys Ala Thr Leu Gln Lys Phe Gly Glu
                    195                 200                 205
Arg Ala Phe Lys Ala Trp Ala Val Ala Arg Leu Ser Gln Arg Phe Pro
                    210                 215                 220
Lys Ala Glu Phe Ala Glu Val Ser Lys Leu Val Thr Asp Leu Thr Lys
225                     230                 235                 240
Val His Thr Glu Cys Cys His Gly Asp Leu Leu Glu Cys Ala Asp Asp
                        245                 250                 255
Arg Ala Asp Leu Ala Lys Tyr Ile Cys Glu Asn Gln Asp Ser Ile Ser
                    260                 265                 270
Ser Lys Leu Lys Glu Cys Cys Glu Lys Pro Leu Leu Glu Lys Ser His
                    275                 280                 285
Cys Ile Ala Glu Val Glu Asn Asp Glu Met Pro Ala Asp Leu Pro Ser
                    290                 295                 300
Leu Ala Ala Asp Phe Val Glu Ser Lys Asp Val Cys Lys Asn Tyr Ala
305                     310                 315                 320
Glu Ala Lys Asp Val Phe Leu Gly Met Phe Leu Tyr Glu Tyr Ala Arg
                        325                 330                 335
Arg His Pro Asp Tyr Ser Val Val Leu Leu Leu Arg Leu Ala Lys Thr
                    340                 345                 350
Tyr Glu Thr Thr Leu Glu Lys Cys Cys Ala Ala Ala Asp Pro His Glu
                    355                 360                 365
Cys Tyr Ala Lys Val Phe Asp Glu Phe Lys Pro Leu Val Glu Glu Pro
                    370                 375                 380
Gln Asn Leu Ile Lys Gln Asn Cys Glu Leu Phe Glu Gln Leu Gly Glu
385                     390                 395                 400
Tyr Lys Phe Gln Asn Ala Leu Leu Val Arg Tyr Thr Lys Lys Val Pro
                        405                 410                 415
Gln Val Ser Thr Pro Thr Leu Val Glu Val Ser Arg Asn Leu Gly Lys
                    420                 425                 430
Val Gly Ser Lys Cys Cys Lys His Pro Glu Ala Lys Arg Met Pro Cys
                    435                 440                 445
Ala Glu Asp Tyr Leu Ser Val Val Leu Asn Gln Leu Cys Val Leu His
                    450                 455                 460
Glu Lys Thr Pro Val Ser Asp Arg Val Thr Lys Cys Cys Thr Glu Ser
465                     470                 475                 480
Leu Val Asn Arg Arg Pro Cys Phe Ser Ala Leu Glu Val Asp Glu Thr
                        485                 490                 495
```

```
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Leu Asp Lys Arg
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Phe Val Asn Gln His
1               5

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid other than tyrosine
<220> FEATURE:
<221> NAME/KEY: MOD_RES
<222> LOCATION: (4)..(13)
<223> OTHER INFORMATION: Region may encompass 0-10 variable amino acids

<400> SEQUENCE: 77

Gly Xaa Gly Xaa Xaa Xaa Xaa Xaa Xaa Xaa Xaa Xaa Xaa Pro Gln Thr
1               5                   10                  15
```

ALBUMIN-INSULIN FUSION PROTEINS

CROSS-REFERENCE TO RELATED APPLICATIONS

This application claims benefit of U.S. Provisional Patent Application No. 60/850,545, filed on Oct. 10, 2006, and U.S. Provisional Patent Application No. 60/835,976, filed on Aug. 7, 2006, the disclosures of which are incorporated herein by reference in their entirety.

BACKGROUND

The invention relates generally to therapeutic proteins which include insulin, an insulin analog, an insulin fragment or variant thereof having insulin activity, fused to albumin or fragments or variants of albumin. The invention encompasses polynucleotides encoding therapeutic albumin-insulin fusion proteins, therapeutic albumin-insulin fusion proteins, compositions, pharmaceutical compositions, formulations and kits. Host cells transformed with the polynucleotides encoding therapeutic albumin-insulin fusion proteins are also encompassed by the invention, as are methods of making the albumin-insulin fusion proteins of the invention using these polynucleotides, and/or host cells.

Albumin is responsible for a significant proportion of the osmotic pressure of serum and also functions as a carrier of endogenous and exogenous ligands. Human serum albumin (HSA, or HA), is a protein of 585 amino acids in its mature form (as shown in FIG. 1A-D). At present, HA for clinical use is produced by extraction from human blood. The production of recombinant HA (rHA) in microorganisms has been disclosed in EP 330 451 and EP 361 991.

Therapeutic proteins in their native state or when recombinantly produced, such as insulin, are typically labile molecules exhibiting short shelf-lives, particularly when formulated in aqueous solutions. The instability in these molecules when formulated for administration dictates that many of the molecules must be lyophilized and refrigerated at all times during storage, thereby rendering the molecules difficult to transport and/or store. Storage problems are particularly acute when pharmaceutical formulations must be stored and dispensed outside of the hospital environment.

Recombinantly produced therapeutic proteins such as insulin also may exhibit a short half-life in vivo, for example after being administered to a patient. Therapeutic proteins such as insulin which exhibit a longer-lived activity in vivo are desirable because they permit longer time periods between dosing in a patient.

Few practical solutions to the storage problems of labile protein molecules have been proposed. Accordingly, there is a need for stabilized, long lasting formulations of proteinaceous therapeutic molecules such as insulin that are easily dispensed, preferably with a simple formulation requiring minimal post-storage manipulation. Furthermore, there is a need for therapeutic proteins such as insulin which exhibit longer-lived activity after being administered to a patient.

SUMMARY OF THE INVENTION

The present invention encompasses albumin-insulin fusion proteins comprising a therapeutic protein having insulin activity. The present invention also encompasses polynucleotides comprising, or alternatively consisting of, nucleic acid molecules encoding a therapeutic protein having insulin activity fused to albumin or a fragment (portion) or variant of albumin. Albumin may be fused to the N-terminus, the C-terminus, or both termini of the therapeutic protein having insulin activity. The present invention also encompasses polynucleotides, comprising, or alternatively consisting of, nucleic acid molecules encoding proteins comprising a therapeutic protein having insulin activity fused to albumin or a fragment (portion) or variant of albumin, that is sufficient to prolong the shelf life of the therapeutic protein, and/or stabilize the therapeutic protein and/or its activity in solution (or in a pharmaceutical composition) in vitro and/or in vivo. Host cells transformed with polynucleotides that encode albumin-insulin fusion protein are also encompassed by the invention, and methods of making the albumin-insulin fusion proteins of the invention and using these polynucleotides of the invention, and/or host cells.

The albumin-insulin fusion proteins described herein generally demonstrate insulin activity. For example, the albumin-insulin fusion proteins bind to the insulin receptor and stimulate glucose uptake in cells that bear the insulin receptor. Generally, the albumin-insulin fusion proteins comprise the B-chain of insulin fused to the A-chain of insulin by a linking sequence. For example, an albumin-insulin may comprise albumin or a variant thereof fused to the N-terminus, C-terminus, or both termini of an insulin analog having a formula —B$_{(1-30)}$—X—A$_{(1-21)}$-, where X is a polypeptide linking sequence. In some embodiments, the linking sequence is 6-30 amino acids in length. Generally, the linking sequence permits or facilitates proper folding of the B-chain and A-chain to form a molecule having insulin activity.

The linking sequence of an insulin analog may be a natural or artificial sequence. Typically, the linking sequence is a polypeptide that includes 4-50 amino acids, and preferably 6-30 amino acids. Natural sequences may be modified by amino acid substitutions, additions, or deletions to create artificial sequences. Preferably linking sequences may include amino acids sequences of natural human protein that are present in human blood and thus are unlikely to elicit an immune response. Examples of natural sequences may include the native insulin C-peptide linking sequence (RREAEDLQVGQVELGGGPGAGSLQPLALEGSLQKR) (SEQ ID NO:1), the IGF-I C-peptide linking sequence (GYGSSSRRAPQT) (SEQ ID NO:2), and fragments of albumin (FIG. 1A-D). In some embodiments, the linking sequence does not include the full-length C-peptide linking sequence of insulin. In other embodiments, the linking sequence includes at least a portion of the C-peptide linking sequence of IGF-I. Optionally, the albumin-insulin fusion protein may include the C-peptide linking sequence of IGF-I which has been modified to include one or more amino acid substitutions, additions, or deletions such that the albumin-insulin fusion protein does not bind to the IGF-I receptor or binds with a lower affinity than IGF-I. In some embodiments, the albumin-insulin fusion protein binds to the IGF-I receptor with a relative affinity of no more than about 80%, about 60%, about 40%, about 20%, about 10%, or about 5%, relative to the affinity of IGF-I for the IGF-I receptor. In some embodiments, the albumin-insulin fusion protein includes the C-peptide linking sequence of IGF-I which has been modified to replace the tyrosine a position 2 with an amino acid other than tyrosine (e.g., alanine, glycine, or serine). Preferably, the albumin-insulin fusion protein does not exhibit mitogenic activity or exhibits mitogenic activity less than about 50% relative to IGF-I (or preferably less than about 30% relative to IGF-I or more preferably less than about 10% relative to IGF-I). In some embodiments, mitogenic activity of albumin-insulin fusion proteins may be assessed in vitro in appropriate cell culture lines (e.g., the L6 cell line).

The linking sequence may be selected to include or omit certain amino acids. In some embodiments, the linking sequence does not include a sequence of two basic amino acid residues in succession selected from the group consisting of KK, KR, RK, and RR. The linking sequence may be selected not to include a lysine residue or an arginine residue. The linking sequence may be selected not to include a tyrosine residue.

The albumin-insulin fusion proteins may include albumin fused to the N-terminus, the C-terminus, or both the N-terminus and C-terminus of an insulin polypeptide or analog. For example, the albumin-insulin fusion proteins may include albumin fused to the N-terminus, the C-terminus, or both the N-terminus and C-terminus of an insulin analog having a formula —B$_{(1-30)}$—X-A$_{(1-21)}$-, where X is a linking sequence for the B-chain and A-chain of insulin.

The albumin-insulin fusion proteins further may comprise an N-terminal leader or signal sequence. Examples of N-terminal leader or signal sequences include albumin leader sequence, insulin leader sequence, MPIF-1 signal sequence, stanniocalcin signal sequence, invertase signal sequence, yeast mating factor alpha signal sequence, *K. lactis* killer toxin leader sequence, immunoglobulin Ig signal sequence, Fibulin B precursor signal sequence, clusterin precursor signal sequence, insulin-like growth factor-binding protein 4 signal sequence, acid phosphatase (PHO5) leader, pre-sequence of MFoz-1, pre-sequence of 0 glucanase (BGL2), *S. diastaticus* glucoamylase II secretion leader sequence; *S. carlsbergensis* alpha-galactosidase (MEL1) secretion leader sequence; *Candida* glucoamylase leader sequence; gp67 signal sequence for use in a baculovirus expression system; and *S. cerevisiae* invertase (SUC2) leader. Further examples of N-terminal leader or signal sequences include a hybrid signal sequence MKWVSFISLLFLFSSAYSRSLEKR) (SEQ ID NO:3); an HSA/MFalpha-1 hybrid signal sequence (MKWVSFISLLFLFSSAYSRSLDKR) (SEQ ID NO:4); a *K. lactis* killer/MFalpha-1 fusion leader sequence (MNIFYI-FLFLLSFVQGSLDKR) (SEQ ID NO:5); a variant of the pre-pro-region of HSA (MKWVSFISLLFLFSSAYSRGV-FRR) (SEQ ID NO:6); a variant of the pre-pro-region of HSA (MKWVTFISLLFLFAGVLG) (SEQ ID NO:7); a variant of the pre-pro-region of HSA (MKWVTFISLLFLF-SGVLG) (SEQ ID NO:8); a variant of the pre-pro-region of HSA (MKWVTFISLLFLFGGVLG) (SEQ ID NO:9); a modified HSA leader (MKWVTFISLLFLFAGVSG) (SEQ ID NO:10); a modified HSA leader (MKWVTFISLLFLF-GGVSG) (SEQ ID NO:11); a modified HSA (A14) leader (MKWVTFISLLFLFAGVSG) (SEQ ID NO:10); a modified HSA (S14) leader (MKWVTFISLLFLFSGVSG) (SEQ ID NO:12), a modified HSA (G14) leader (MKWVTFLSLL-FLFGGVSG) (SEQ ID NO:13); a modified HSA (G14) leader (MKWVTFISLLFLFGGVLGDLHKS) (SEQ ID NO:14); a consensus signal sequence (MPTWAWWLFLV-LLLALWAPARG) (SEQ ID NO:15); *K. lactis* killer toxin prepro sequence (MNIFYIFLFLLSFVQGLEHTHRRG-SLDKR) (SEQ ID NO:16); inulinase sequence (MKLAY-SLLLPLAGVSASVINYKR) (SEQ ID NO:17).

In some embodiments, the albumin-insulin fusion proteins include an insulin analog having a formula —B$_{(1-30)}$—X-A$_{(1-21)}$-, where X is a polypeptide that comprises a fragment of albumin (e.g., a fragment of about 6-about 30 amino acids). For example, the fragment of albumin may be selected from NPNLPRLVR (CoGenesys Linking Sequence No. 1) (SEQ ID NO:18), KDDNPNLPRLVR (CoGenesys Linking Sequence No. 2) (SEQ ID NO:19) and NDEMPAD (CoGenesys Linking Sequence No. 3) (SEQ ID NO:20).

In other embodiments, the albumin-insulin fusion proteins comprise albumin or a variant thereof fused to the N-terminus or C-terminus of an insulin analog having a formula —B$_{(1-30)}$—X-A$_{(1-21)}$-, where X is a polypeptide that does not include a sequence of two basic amino acid residues in succession selected from the group consisting of KK, KR, RK, and RR. In some embodiments, X is a polypeptide that does not include a lysine residue or an arginine residue. Typically, X is a polypeptide that is about 6-about 30 amino acids in length. Preferably, the fusion protein does not bind to the IGF-I receptor or binds with a lower affinity than IGF-I. In some embodiments, the albumin-insulin fusion protein binds to the IGF-I receptor with a relative affinity of no more than about 80%, about 60%, about 40%, about 20%, about 10%, or about 5%, relative to the affinity of IGF-I for the IGF-I receptor.

In further embodiments, the albumin-insulin fusion proteins comprise albumin or a variant thereof fused to the N-terminus or C-terminus of an insulin analog having a formula —B$_{(1-30)}$—X-A$_{(1-21)}$-, where X is a polypeptide comprising a fragment of IGF-I C-peptide (e.g., a fragment of 6-30 amino acids). Typically, the fusion protein the albumin-insulin fusion protein does not bind to the IGF-I receptor or binds with a lower affinity than IGF-I. In some embodiments, the albumin-insulin fusion protein binds to the IGF-I receptor with a relative affinity of no more than about 80%, 60%, 40%, 20%, 10%, or 5%, relative to the affinity of IGF-I for the IGF-I receptor. In some embodiments, X is a polypeptide that does not include selected amino acids such as a tyrosine residue (e.g., the polypeptide may not include a tyrosine residue at amino acid position 2), or basic amino acid residues (e.g., the polypeptide may not include lysine or arginine in succession).

In additional embodiments, the albumin-insulin fusion protein comprises albumin or a variant thereof fused to the N-terminus or C-terminus of an insulin analog having a formula, —B$_{(1-30)}$—X-A$_{(1-21)}$-, where X is a polypeptide having the sequence -G-Z$^1$-G-Z$^2_n$-; Z$^1$ is not tyrosine; Z$^2$ is an amino acid where n=0-10; and the fusion protein does not bind to the IGF-I receptor or binds with a lower affinity than IGF-I. In some embodiments, the albumin-insulin fusion proteins binds to the IGF-I receptor with a relative affinity of no more than about 80%, about 60%, about 40%, about 20%, about 10%, or about 5%, relative to the affinity of IGF-I for the IGF-I receptor. In some embodiments, X is a polypeptide having the sequence -G-Z$^1$-G-Z$^2_n$-P-Q-T- and includes about 6-about 30 amino acids. Examples of X may include GGGPQT (CoGenesys Linking Sequence No. 5) (SEQ ID NO:21), and GAGSSSRRAPQT (CoGenesys Linking Sequence No. 6) (SEQ ID NO:22).

In further embodiments, the albumin-insulin fusion proteins comprise albumin or a variant thereof fused to the N-terminus or C-terminus of an insulin analog having a formula, —B$_{(1-30)}$—X-A$_{(1-21)}$-, where X is a polypeptide that does not comprise full-length insulin C-peptide (e.g., a fragment of C-peptide that includes about 6-about 30 amino acids). The selected portion of insulin C-peptide may not include certain amino acids (e.g., the portion may not include two basic amino acid residues in succession). Examples of X include a polypeptide having an amino acid sequence GGGPGAG (CoGenesys Linking Sequence No. 7) (SEQ ID NO:23). Preferably, the albumin-insulin fusion protein does not bind to IGF-I receptor or binds with a lower affinity than IGF-I. In some embodiments, the albumin-insulin fusion protein binds to the IGF-I receptor with a relative affinity of no more than about 80%, about 60%, about 40%, about 20%, about 10%, or about 5%, relative to the affinity of IGF-I for the IGF-I receptor.

The invention also encompasses pharmaceutical formulations comprising an albumin-insulin fusion protein of the invention and a pharmaceutically acceptable diluent or carrier. Such formulations may be in a kit or container. Such kit or container may be packaged with instructions pertaining to the extended shelf life of the therapeutic protein. Such formulations may be used in methods of treating, preventing, ameliorating or diagnosing a disease or disease symptom in a patient, preferably a mammal, most preferably a human, comprising the step of administering the pharmaceutical formulation to the patient. In some embodiments, the patients has or is at risk for developing a disease associated with insulin deficiency (e.g., insulin-dependent diabetes mellitus).

The albumin-insulin fusion proteins described herein may exhibit extended insulin activity relative to an insulin polypeptide that is not fused to albumin. For example, the albumin-insulin fusion proteins may exhibit extended insulin activity in vitro or in vivo.

Also disclosed are pharmaceutical compositions that include the albumin-insulin fusion proteins and at least one pharmaceutical excipient. The pharmaceutical compositions may be administered to any patient in need thereof including human patients and non-human patients (e.g., dogs, cats, horses). The pharmaceutical compositions may be administered to treat or prevent any metabolic disease or syndrome in which treatment with insulin is beneficial. In some embodiments, the pharmaceutical composition are administered to a patient in need thereof to treat insulin-dependent diabetes mellitus, non-insulin-dependent diabetes, or polycystic ovarian syndrome.

Pharmaceutical formulations of the albumin-insulin fusion proteins may include aerosol formulations. Suitable aerosol formulations may include aqueous, propellant-based or nonpropellant-based formulations for pulmonary delivery, nasal delivery, or both, in which essentially every inhaled particle contains the albumin-insulin fusion protein. Suitable aerosol formulations of the albumin-insulin fusion protein may include dry powder aerosol formulations (e.g., dry powder, propellant-based aerosol formulations). The albumin-insulin fusion protein may be present in the aerosol formulation at any suitable concentration or concentration range. For aqueous aerosol formulations, the albumin-insulin fusion protein may be present, for example, at a concentration range of about 0.05 mg/mL, about 0.1 mg/mL, about 2 mg/mL, about 40 mg/mL, or about 100 mg/mL, to about 600 mg/mL. about 0.05 mg/g, about 0.1 mg/g, about 2 mg/g, about 40 mg/g, or about 100 mg/g, to about 990 mg/g (or any increment of 1 mg/g in between 0.1 mg/mL up to 600 mg/mL). Aerosol formulations of the albumin-insulin fusion proteins may provide effective delivery of the albumin-insulin fusion protein to appropriate areas of the lung cavities, nasal cavities, or both. In some embodiments, aerosol formulations may deliver an effective concentration of the albumin-insulin fusion protein to the lung in less than about 120 seconds, and preferably less than about 60 seconds, more preferably less than about 30 seconds, most preferably less than about 15 seconds.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-D shows the amino acid sequence of the mature form of human albumin and a polynucleotide encoding it.

FIG. 15 shows serum albulin concentration time curves following a single IV dose of 1 mg/kg.

FIG. 16 shows serum albulin concentration time curves following a single IV dose of 3 mg/kg.

DETAILED DESCRIPTION OF THE PREFERRED EMBODIMENTS

Figure 2:
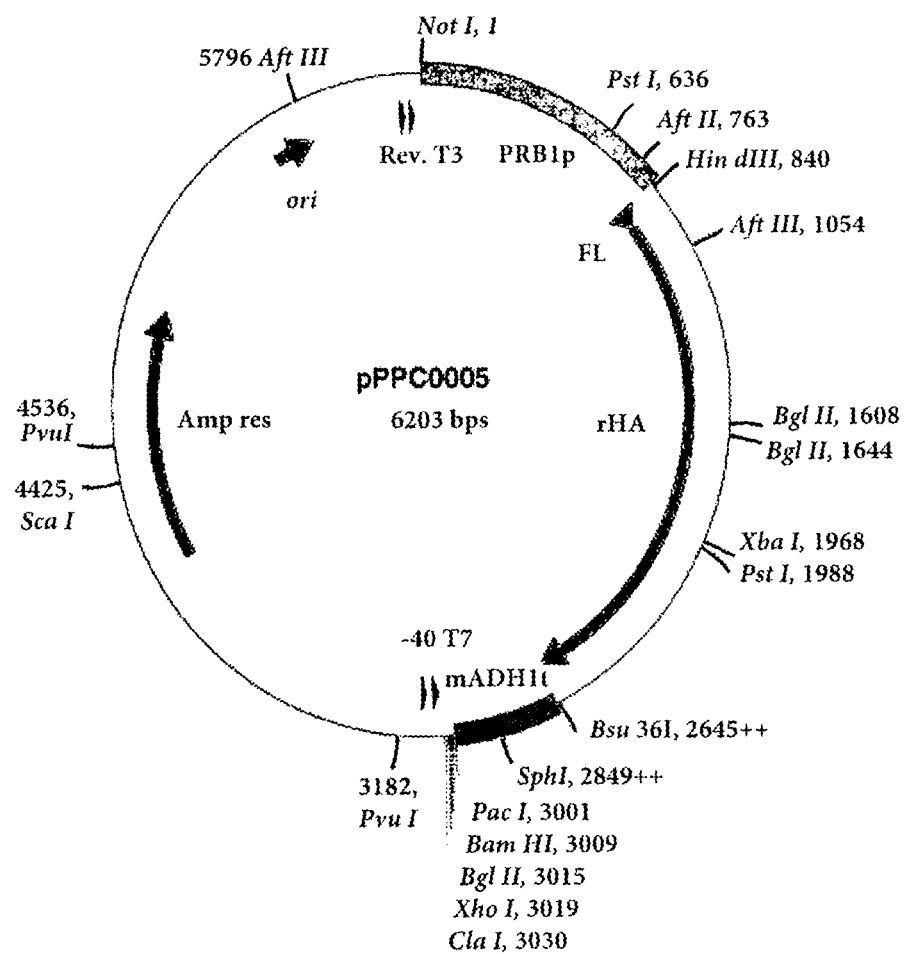
FIG. 2 shows the restriction map of the pPPC0005 cloning vector ATCC deposit PTA-3278.

Fusion of bioactive proteins and peptides to human serum albumin has proven valuable in creating new protein products with medical use. While the extension of half-life imbued on the bioactive component may seem obvious (since albumin has a long half-life) in practice, even this concept has proven far from predictable. The half-life of albumin fusion proteins is always shorter than albumin, and the plasma half-life of albumin fusion proteins varies widely depending on the protein composition and even the host system used to manufacture. For example, when manufactured in yeast, erythropoietin-HSA has a short half-life (not appreciably longer than EPO itself), whereas when manufactured in mammalian cells EPO-HSA has a longer half-life.

The half-life of some albumin fusion proteins is long enough to support once-weekly or less frequent administration in man (for example fusions with interferon-alpha, growth hormone, and GLP-1) whereas with other proteins, (for example insulin, the half-life is shorter and thus more frequent dosing is required). Some fusion proteins have half-lives so long that they may not be safe, others have half-lives too short to have medical use. Moreover, the influence of composition and orientation has proven an unpredictable feature of albumin fusion proteins. Some work well on the N-terminus of HSA, others on the C-terminus. Some proteins simply do not function at all when fused with albumin at the N-terminus, C-terminus, or both termini (examples in Table A, below).

TABLE A

Examples of proteins that were not active when manufactured as albumin fusions

| Protein | Activity Comments | N-terminus | C-terminus |
|---|---|---|---|
| PYY | cAMP assay works well for peptide, no activity for fusion protein | Not active | Not active |
| T20 (Fuzeon) | In vitro HIV infection assays, peptide works well, fusions no activity | Not active | Not active |
| beta-defensin | Antimicrobial peptide, not active as fusion protein | Not active | Not active |
| Hirulog | (thrombin inhibitor based on hirudin) peptide is active, fusion protein is not | Not active | Not active |
| CGRP | cAMP-based assay, peptide works well, fusion protein not active | Not active | Not active |
| NOGO receptor | Soluble receptor is active as FC and independent domain, not active as HSA fusion | Not active | Not active |
| Dynorphin (and other opioid peptides) | Weak activity in vitro, no activity in vivo | Not active | Not active |
| GLP-1 | cAMP assay | Active | Not active |

The most surprising attribute of the technology has proven the breadth of medical usefulness that extends beyond the simple idea of making a protein last longer in the blood and therefore be more convenient for the patient. For example, albumin fusion can improve the therapeutic index (the window between beneficial action and adverse effects) in unpredictable ways. Albulin is an example of this. Daily administration results in a very flat exposure profile that can be titrated in each patient to the target therapeutic level. By avoiding the large peak-to-trough variations in insulin exposure that limit the real-world efficacy of current insulin therapies, the unique pharmacokinetic profile of Albulin should allow patients to achieve target insulin levels (and therefore target blood glucose levels) without risking dangerous hypoglycemic episodes that are associated with unwanted spikes in insulin levels.

Lastly, albumin fusion changes the tissue distribution profile of proteins. Subcutaneous delivery of insulin results in higher insulin levels in the periphery (muscle and fat) than at the liver. The result is greater risk of hypoglycemia and weight gain. Albumin exists in a steady-state concentration profile in the body such that this is reversed, the liver is exposed to higher levels than the periphery. Albumin fusion may confer on insulin a greater hepatic exposure profile, thus lending further improvement on the desired action of insulin in diabetes with improved efficacy, reduced risk of severe hypoglycemia and reduced weight gain.

Definitions

The following definitions are provided to facilitate understanding of certain terms used throughout this specification.

As used herein, "polynucleotide" refers to a nucleic acid molecule having a nucleotide sequence encoding a protein. For example, a polynucleotide may encode fusion protein comprising, or alternatively consisting of, at least one molecule of albumin (or a fragment or variant thereof) joined in frame to at least one therapeutic protein having insulin activity.

As used herein, "albumin fusion construct" refers to a nucleic acid molecule comprising, or alternatively consisting of, a polynucleotide encoding at least one molecule of albumin (or a fragment or variant thereof) joined in frame to at least one polynucleotide encoding at least one molecule of a therapeutic protein having insulin activity; a nucleic acid molecule comprising, or alternatively consisting of, a polynucleotide encoding at least one molecule of albumin (or a fragment or variant thereof) joined in frame to at least one polynucleotide encoding at least one molecule of a therapeutic protein having insulin activity (or fragment or variant thereof) generated as described in the Examples; or a nucleic acid molecule comprising, or alternatively consisting of, a polynucleotide encoding at least one molecule of albumin (or a fragment or variant thereof) joined in frame to at least one polynucleotide encoding at least one molecule of a therapeutic protein having insulin activity (or fragment or variant thereof), further comprising, for example, one or more of the following elements: (1) a functional self-replicating vector (including but not limited to, a shuttle vector, an expression vector, an integration vector, and/or a replication system), (2) a region for initiation of transcription (e.g., a promoter region, such as for example, a regulatable or inducible promoter, a constitutive promoter), (3) a region for termination of transcription, (4) a leader sequence, and (5) a selectable marker. The polynucleotide encoding the therapeutic protein having insulin activity and albumin protein, once part of the albumin fusion construct, may each be referred to as a "portion," "region" or "moiety" of the albumin fusion construct.

The present invention relates generally to polynucleotides encoding albumin fusion proteins; albumin fusion proteins; and methods of treating, preventing, or ameliorating diseases or disorders using albumin fusion proteins or polynucleotides encoding albumin fusion proteins. As used herein, "albumin fusion protein" refers to a protein formed by the fusion of at least one molecule of albumin (or a fragment or variant thereof) to at least one molecule of a therapeutic protein having insulin activity (or fragment or variant thereof). An albumin fusion protein of the invention comprises at least a fragment or variant of a therapeutic protein having insulin activity and at least a fragment or variant of human serum albumin, which are associated with one another by genetic fusion (i.e., the albumin fusion protein is generated by translation of a nucleic acid in which a polynucleotide encoding all or a portion of a therapeutic protein having insulin activity is joined in-frame with a polynucleotide encoding all or a portion of albumin). The therapeutic protein having insulin activity and albumin protein, once part of the albumin fusion protein, may each be referred to as a "portion," "region" or "moiety" of the albumin fusion protein (e.g., a "therapeutic protein having insulin activity portion" or an "albumin protein portion"). In a highly preferred embodiment, an albumin fusion protein of the invention comprises at least one molecule of a therapeutic protein having insulin activity or fragment or variant of thereof (including, but not limited to a mature form of the therapeutic protein having insulin activity) and at least one molecule of albumin or fragment or variant thereof (including but not limited to a mature form of albumin).

In a further preferred embodiment, an albumin fusion protein of the invention is processed by a host cell and secreted into the surrounding culture medium. Processing of the nascent albumin fusion protein that occurs in the secretory pathways of the host used for expression may include, but is not limited to signal peptide cleavage; formation of disulfide bonds; proper folding; addition and processing of carbohydrates (such as for example, N- and O-linked glycosylation); specific proteolytic cleavages; and assembly into multimeric proteins. An albumin fusion protein of the invention is preferably in the processed form. In a most preferred embodiment, the "processed form of an albumin fusion protein" refers to an albumin fusion protein product which has undergone N-terminal signal peptide cleavage, herein also referred to as a "mature albumin fusion protein."

In further embodiments, the invention provides an albumin fusion protein comprising, or alternatively consisting of, a therapeutic protein having insulin activity, and a biologically active and/or therapeutically active fragment of serum albumin. In further embodiments, the invention provides an albumin fusion protein comprising, or alternatively consisting of, a therapeutic protein having insulin activity and a biologically active and/or therapeutically active variant of serum albumin. In preferred embodiments, the therapeutic protein having insulin activity portion of the albumin fusion protein is the mature portion of the therapeutic protein having insulin activity. In a further preferred embodiment, the therapeutic protein having insulin activity portion of the albumin fusion protein is the extracellular soluble domain of the therapeutic protein having insulin activity. In an alternative embodiment, the therapeutic protein having insulin activity portion of the albumin fusion protein is the active form of the therapeutic protein having insulin activity. The invention further encompasses polynucleotides encoding these albumin fusion proteins.

In further embodiments, the invention provides an albumin fusion protein comprising, or alternatively consisting of, a biologically active and/or therapeutically active fragment or variant of a therapeutic protein having insulin activity and a biologically active and/or therapeutically active fragment or variant of serum albumin. In preferred embodiments, the invention provides an albumin fusion protein comprising, or alternatively consisting of, the mature portion of a therapeutic protein having insulin activity and the mature portion of serum albumin. The invention further encompasses polynucleotides encoding these albumin fusion proteins.

Therapeutic Proteins

As stated above, a polynucleotide of the invention encodes a protein comprising or alternatively consisting of, at least a fragment or variant of a therapeutic protein and at least a fragment or variant of human serum albumin, which are associated with one another, preferably by genetic fusion. The preferred therapeutic protein is insulin or an insulin analog. Insulin (110 amino acids) has the amino acid sequence: MALWMRLLPL LALLALWGPD PAAAFVNQHL CGSHLVEALY LVCGERGFFY TPKTRREAED LQVGQVELGG GPGAGSLQPL ALEGSLQKRG IVEQCCTSIC SLYQLENYCN (SEQ ID NO:24). The B-chain (1-30 or FVNQHL CGSHLVEALY LVCGERGFFY TPKT) (SEQ ID NO:25) is present at amino acids 25-54. The A-chain (1-21 or G IVEQCCTSIC SLYQLENYCN) (SEQ ID NO:26) is present at amino acids 90-110. The C-peptide (RREAED LQVGQVELGG GPGAGSLQPL ALEGSLQKR) (SEQ ID NO:27) which links the B-chain and A-chain is present at amino acids 55-89. Therapeutic proteins as disclosed herein may include the B-chain and A-chain of insulin linked by the C-peptide of insulin or another natural or artificial sequence. Natural sequence used to link the B-chain and A-chain may be modified to include amino acid substitutions, additions, or deletions. Therapeutic proteins as disclosed herein may include single-chain insulin molecules.

An additional embodiment includes a polynucleotide encoding a protein comprising or alternatively consisting of at least a fragment or variant of a therapeutic protein having insulin activity and at least a fragment or variant of human serum albumin, which are linked with one another by chemical conjugation.

As used herein, "therapeutic protein having insulin activity" refers to an insulin polypeptide, or fragment or variant thereof, or an insulin analog, which may include "single-chain insulin." As used herein, "single-chain insulin" is a protein having the activity of insulin in which the B-chain and A-chain of insulin are linked in a contiguous polypeptide chain by a linking or connecting peptide which may include insulin C-peptide or a C-peptide analog as disclosed herein. For example, a "a single-chain insulin" may include the B-chain of insulin (amino acids 1-30) linked to the A-chain of insulin (amino acids 1-21) with a linking sequence. The linking sequence may include the full-length C-peptide linker of insulin or a fragment of variant thereof (e.g., a variant having one or more amino acid substitutions, additions or deletions). The linking sequence may include a natural or artificial sequence other than the C-peptide linker of insulin (e.g., IGF-I C-peptide, albumin or fragments thereof). Other natural sequences may include modifications (e.g., one or more amino acid substitutions, additions or deletions).

A "therapeutic protein having insulin activity" may include a human or non-human insulin polypeptide (e.g., dog, cat, or horse insulin), or fragment or variant thereof, or an insulin analog (e.g., a dog, cat, or horse insulin analog), which may include "single-chain insulin."

As used herein, the terms peptides, proteins, and polypeptides are used interchangeably. It is specifically contemplated that the term "therapeutic protein having insulin activity" encompasses fragments, variants, and analogs of insulin. Thus a protein of the invention may contain at least a fragment, variant, or an analog of insulin.

By a polypeptide displaying a "therapeutic activity" or a protein that is "therapeutically active" is meant a polypeptide that possesses one or more known biological and/or therapeutic activities associated with a therapeutic protein such as one or more of the albumin-insulin fusion proteins described herein or otherwise known in the art. As a non-limiting example, a "therapeutic albumin-insulin fusion protein" is a protein that is useful to treat, prevent or ameliorate a disease, condition or disorder associated with insulin deficiency. As a non-limiting example, a "therapeutic albumin-insulin fusion protein" may be one that binds specifically to the insulin receptor and stimulates glucose uptake by a cell that bears the receptor (e.g., an adipocyte).

As used herein, "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture. As an example, when insulin or an insulin analog is the therapeutic protein, the effects of insulin on glucose uptake or stimulation of promoter activity as described in the Examples may be used as the endpoint for which therapeutic activity is measured. Such in vitro or cell culture assays are commonly available for insulin.

In some embodiments, the albumin-insulin fusion proteins do not bind to the IGF-I receptor or bind with a lower affinity than IGF-I. For example, the albumin-insulin fusion protein may bind to the IGF-I receptor with a relative affinity of no more than about 80%, 60%, 40%, 20%, 10%, or 5%, relative to the affinity of IGF-I for the IGF-I receptor. Relative affinity of an albumin-insulin fusion protein for the IGF-I receptor as compared to the affinity of IGF-I for the IGF-I receptor may be determined as known in the art. For example, the effective concentration of an albumin-insulin fusion protein at which 50% of maximum is observed for a physiological event (e.g., maximum cell proliferation observed for L6 cells in the presence of the albumin-insulin fusion protein) or "EC50" may be compared to the EC50 for IGF-I.

Vectors for expressing proteins are known in the art, and are available commercially or described elsewhere. For example, as described in the Examples, an "expression cassette" comprising, or alternatively consisting of, one or more of (1) a polynucleotide encoding a given albumin fusion protein, (2) a leader sequence, (3) a promoter region, and (4) a transcriptional terminator, may be assembled in a convenient cloning vector and subsequently be moved into an alternative vector, such as, for example, an expression vector including, for example, a yeast expression vector or a mammalian expression vector. In one embodiment, for expression in S. cerevisiae, an expression cassette comprising, or alternatively consisting of, a nucleic acid molecule encoding an albumin fusion protein is cloned into pSAC35. In another embodiment, for expression in CHO cells, an expression cassette comprising, or alternatively consisting of, a nucleic acid molecule encoding an albumin fusion protein is cloned into pC4. In a further embodiment, a polynucleotide comprising or alternatively consisting of a nucleic acid molecule encoding the therapeutic protein portion of an albumin fusion protein is cloned into pC4:HSA. In a still further embodiment, for expression in NS0 cells, an expression cassette comprising, or alternatively consisting of, a nucleic acid molecule encoding an albumin fusion protein is cloned into pEE12. Other useful cloning and/or expression vectors will be known to the skilled artisan and are within the scope of the invention.

Certain albumin-insulin fusion constructs disclosed in this application have been deposited with the ATCC™: pSAC35: HSA.INSULIN(GYG) (also named pSAC35.HSA.INSULIN(GYG).F1-N62), ATCC No. PTA-3916, deposited Dec. 7, 2001; pSAC35:INSULIN(GYG).HSA (also named pSAC35.INSULIN(GYG).F1-N62.HSA), ATCC No. PTA-3917, deposited Dec. 7, 2001; pSAC35:HSA.INSULIN (GGG) (also named pSAC35.HSA.INSULIN(GGG).F1-N58), ATCC No. PTA-3918, deposited Dec. 7, 2001.

In a further embodiment of the invention, an "expression cassette" comprising, or alternatively consisting of one or more of (1) a polynucleotide encoding a given albumin fusion protein, (2) a leader sequence, (3) a promoter region, and (4) a transcriptional terminator can be moved or "subcloned" from one vector into another. Fragments to be subcloned may be generated by methods well known in the art, such as, for example, PCR amplification and/or restriction enzyme digestion.

In preferred embodiments, the albumin-insulin fusion proteins of the invention are capable of a therapeutic activity and/or biologic activity corresponding to the insulin activity of the insulin portion of the albumin fusion protein.

Non-Human Albumin Fusion Proteins of Insulin.

In one embodiment, the albumin fusion proteins of the invention may comprise one or more serum albumin proteins of a human or non-human animal species, fused in tandem and in-frame either at the N-terminus or the C-terminus to one or more insulin proteins of the same non-human animal species. Non-human Serum Albumin and insulin proteins are well known in the art and available in public databases. In a specific embodiment, the albumin fusion protein of the invention comprises one or more Bos taurus Serum Albumin proteins, fused in tandem and in-frame either at the N-terminus or the C-terminus to one or more insulin proteins.

Fusion proteins comprising fragments or variants of non-human Serum Albumin, such as, for example, the mature form of Serum Albumin, are also encompassed by the invention. Fusion proteins comprising fragments or variants of insulin proteins, such as, for example, a single-chain equivalent of the mature form of insulin, are also encompassed by the invention. Preferably the a single-chain equivalent of the mature form of insulin retains insulin activity, i.e., (binds to the insulin receptor and effects uptake of glucose into cell that bears the receptor on its surface).

Polynucleotides of the invention comprise, or alternatively consist of, one or more nucleic acid molecules encoding a human or non-human albumin fusion protein described above.

The above-described non-human albumin fusion proteins are encompassed by the invention, as are host cells and vectors containing these polynucleotides. In one embodiment, a non-human albumin fusion protein encoded by a polynucleotide as described above has an extended shelf life. In an additional embodiment, a non-human albumin fusion protein encoded by a polynucleotide described above has a longer serum half-life and/or more stabilized activity in solution (or in a pharmaceutical composition) in vitro and/or in vivo than the corresponding unfused therapeutic molecule.

Non-human serum albumin may include:
Bos taurus ABBOS, CAA76847, P02769, CAA41735, 229552, AAF28806, AAF28805, AAF28804, AAA51411
Sus scrofa P08835, CAA30970, AAA30988
Equus caballus ABHOS, AAG40944, P35747, CAA52194
Ovis aries ABSHS, P14639, CAA34903
Salmo salar ABONS2, ABONS2, CAA36643, CAA43187
Gallus gallus ABCHS, P19121, CAA43098
Felis catus P49064, S57632, CAA59279, JC4660
Canis P49822, S29749, CAB64867, familiaris CAA76841, AAB30434

Polypeptide and Polynucleotide Fragments and Variants
Fragments

The present invention is further directed to fragments of the therapeutic proteins (e.g., insulin or insulin analogs), albumin proteins, and/or albumin fusion proteins of the invention. The present invention is also directed to polynucleotides encoding fragments of the therapeutic proteins (e.g., insulin or insulin analogs), albumin proteins, and/or albumin fusion proteins of the invention.

Even if deletion of one or more amino acids from the N-terminus of a protein results in modification or loss of one or more biological functions of the therapeutic protein (e.g., insulin or an insulin analog), albumin protein, and/or albumin fusion protein of the invention, other therapeutic activities and/or functional activities (e.g., biological activities, ability to multimerize, ability to bind a receptor) may still be retained.

Accordingly, fragments of a therapeutic protein (e.g., insulin or insulin analogs) corresponding to a therapeutic protein portion of an albumin fusion protein of the invention, include the full length protein as well as polypeptides having one or more residues deleted from the amino terminus of the amino acid sequence of the reference polypeptide.

In addition, fragments of serum albumin polypeptides corresponding to an albumin protein portion of an albumin fusion protein of the invention, include the full length protein as well as polypeptides having one or more residues deleted from the amino terminus of the amino acid sequence of the reference polypeptide.

Moreover, fragments of albumin fusion proteins of the invention, include the full length albumin fusion protein as well as polypeptides having one or more residues deleted from the amino terminus of the albumin fusion protein.

Also as mentioned above, even if deletion of one or more amino acids from the N-terminus or C-terminus of a reference polypeptide (e.g., a therapeutic protein; serum albumin protein; or albumin fusion protein of the invention) results in modification or loss of one or more biological functions of the protein, other functional activities (e.g., biological activities, ability to multimerize, ability to bind a ligand) and/or therapeutic activities may still be retained. Whether a particular polypeptide lacking the N-terminal and/or C-terminal residues of a reference polypeptide retains therapeutic activity can readily be determined by routine methods described herein and/or otherwise known in the art.

The present invention further provides polypeptides having one or more residues deleted from the carboxy terminus of the amino acid sequence of a therapeutic protein (e.g., insulin or an insulin analog) corresponding to a therapeutic protein portion of an albumin fusion protein of the invention. In addition, the present invention provides polypeptides having one or more residues deleted from the carboxy terminus of the amino acid sequence of an albumin protein corresponding to an albumin protein portion of an albumin fusion protein of the invention.

In addition, any of the above described N- or C-terminal deletions can be combined to produce a N- and C-terminal deleted reference polypeptide. The invention also provides polypeptides having one or more amino acids deleted from both the amino and the carboxyl termini. Polynucleotides encoding these polypeptides are also encompassed by the invention.

The present application is also directed to proteins containing polypeptides at least 80%, 85%, 90%, 95%, 96%, 97%, 98% or 99% identical to a reference polypeptide sequence (e.g., an insulin polypeptide or insulin analog, or a therapeutic protein portion of an albumin-insulin fusion protein of the invention, or an albumin protein portion of an albumin-insulin fusion protein of the invention) set forth herein, or fragments thereof. In preferred embodiments, the application is directed to proteins comprising polypeptides at least 80%, 85%, 90%, 95%, 96%, 97%, 98% or 99% identical to reference polypeptides having the amino acid sequence of N- and C-terminal deletions as described above. Polynucleotides encoding these polypeptides are also encompassed by the invention.

Preferred polypeptide fragments of the invention are fragments comprising, or alternatively consisting of, an amino acid sequence that displays a therapeutic activity and/or functional activity (e.g. biological activity) of the polypeptide sequence of the therapeutic protein or serum albumin protein of which the amino acid sequence is a fragment. For example, a preferred fragment of insulin has insulin receptor binding activity and optionally may not have an undesirable activity, e.g., IGF-I receptor binding activity.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Variants

"Variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide.

As used herein, "variant," refers to a therapeutic protein portion of an albumin fusion protein of the invention, albumin portion of an albumin fusion protein of the invention, or albumin fusion protein of the invention differing in sequence from a therapeutic protein, albumin protein, and/or albumin fusion protein, respectively, but retaining at least one functional and/or therapeutic property thereof as described elsewhere herein or otherwise known in the art. Generally, variants are overall very similar, and, in many regions, identical to the amino acid sequence of the therapeutic protein corresponding to a therapeutic protein portion of an albumin fusion protein, albumin protein corresponding to an albumin protein portion of an albumin fusion protein, and/or albumin fusion protein. Nucleic acids encoding these variants are also encompassed by the invention. For example, a preferred variant of insulin has insulin receptor binding activity and optionally may not have an undesirable activity, e.g., IGF-I receptor binding activity.

The present invention is also directed to proteins which comprise, or alternatively consist of, an amino acid sequence which is at least about 80%, about 85%, about 90%, about 95%, about 96%, about 97%, about 98%, about 99% or about 100%, identical to, for example, the amino acid sequence of a therapeutic protein corresponding to a therapeutic protein portion of an albumin fusion protein of the invention; or the amino acid sequence of a therapeutic protein portion of an albumin fusion protein encoded by a polynucleotide or albumin fusion construct, or fragments or variants thereof), albumin proteins corresponding to an albumin protein portion of an albumin fusion protein of the invention (e.g., the amino acid sequence of an albumin protein portion of an albumin fusion protein encoded by a polynucleotide or albumin fusion construct; the amino acid sequence shown in FIGS. 1A-D; or fragments or variants thereof), and/or albumin fusion proteins. Fragments of these polypeptides are also provided (e.g., those fragments described herein). Further polypeptides encompassed by the invention are polypeptides encoded by polynucleotides which hybridize to the complement of a nucleic acid molecule encoding an albumin fusion protein of the invention under stringent hybridization conditions (e.g., hybridization to filter bound DNA in 6× Sodium chloride/Sodium citrate (SSC) at about 45 degrees Celsius, followed by one or more washes in 0.2×SSC, 0.1% SDS at about 50-65 degrees Celsius), under highly stringent conditions (e.g., hybridization to filter bound DNA in 6× sodium chloride/Sodium citrate (SSC) at about 45 degrees Celsius, followed by one or more washes in 0.1×SSC, 0.2% SDS at about 68 degrees Celsius), or under other stringent hybridization conditions which are known to those of skill in the art (see, for example, Ausubel, F. M. et al., eds., 1989 Current protocol in Molecular Biology, Green publishing associates, Inc., and John Wiley & Sons Inc., New York, at pages 6.3.1-6.3.6 and 2.10.3). Polynucleotides encoding these polypeptides are also encompassed by the invention.

By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, about 85%, about 90%, about 95%, about 96%, about 97%, about 98% or about 99% identical to, for instance, the amino acid sequence of an albumin fusion protein of the invention or a fragment thereof (such as a therapeutic protein portion of the albumin fusion protein or an albumin portion of the albumin fusion protein), can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are either both nucleotide sequences or both amino acid sequences. The result of said global sequence alignment is expressed as percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variant will usually have at least 75% (preferably at least about 80%, 90%, 95% or 99%) sequence identity with a length of normal HA or therapeutic protein which is the same length as the variant. Homology or identity at the nucleotide or amino acid sequence level is determined by BLAST (Basic Local Alignment Search Tool) analysis using the algorithm employed by the programs blastp, blastn, blastx, tblastn and tblastx (Karlin et al., Proc. Natl. Acad. Sci. USA 87: 2264-2268 (1990) and Altschul, J. Mol. Evol. 36: 290-300 (1993), fully incorporated by reference) which are tailored for sequence similarity searching.

The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al., (Nature Genetics 6: 119-129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., Proc. Natl. Acad. Sci. USA 89: 10915-10919 (1992), fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively. Four blastn parameters may be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

The polynucleotide variants of the invention may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, polypeptide variants in which less than 50, less than 40, less than 30, less than 20, less than 10, or 5-50, 5-25, 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host, such as, yeast or E. coli).

In a preferred embodiment, a polynucleotide of the invention which encodes the albumin portion of an albumin fusion protein is optimized for expression in yeast or mammalian cells. In a further preferred embodiment, a polynucleotide of the invention which encodes the therapeutic protein portion of an albumin fusion protein is optimized for expression in yeast or mammalian cells. In a still further preferred embodiment, a polynucleotide encoding an albumin fusion protein of the invention is optimized for expression in yeast or mammalian cells.

In an alternative embodiment, a codon optimized polynucleotide which encodes a therapeutic protein portion of an albumin fusion protein does not hybridize to the wild type polynucleotide encoding the therapeutic protein under stringent hybridization conditions as described herein. In a further embodiment, a codon optimized polynucleotide which encodes an albumin portion of an albumin fusion protein does not hybridize to the wild type polynucleotide encoding the albumin protein under stringent hybridization conditions as described herein. In another embodiment, a codon optimized polynucleotide which encodes an albumin fusion protein does not hybridize to the wild type polynucleotide encoding the therapeutic protein portion or the albumin protein portion under stringent hybridization conditions as described herein.

In an additional embodiment, a polynucleotide which encodes a therapeutic protein portion of an albumin fusion protein does not comprise, or alternatively consist of, the naturally occurring sequence of that therapeutic protein. In a further embodiment, a polynucleotide which encodes an albumin protein portion of an albumin fusion protein does not comprise, or alternatively consist of, the naturally occurring sequence of albumin protein. In an alternative embodiment, a polynucleotide which encodes an albumin fusion protein does not comprise, or alternatively consist of, the naturally occurring sequence of a therapeutic protein portion or the albumin protein portion.

Naturally occurring variants are called "allelic variants," and refer to one of several alternate forms of a gene occupying a given locus on a chromosome of an organism. (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the polypeptide of the present invention without substantial loss of biological function. As an example, Ron et al. (J. Biol. Chem. 268: 2984-2988 (1993)) reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988).)

Moreover, ample evidence demonstrates that variants often retain a biological activity similar to that of the naturally occurring protein. For example, Gayle and coworkers (J. Biol. Chem. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "most of the molecule could be altered with little effect on either binding or biological activity." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. Whether a particular polypeptide lacking N- or C-terminal residues of a protein retains such immunogenic activities can readily be determined by routine methods described herein and otherwise known in the art.

Thus, the invention further includes polypeptide variants which have a functional activity (e.g., biological activity and/or therapeutic activity). In one embodiment, the invention provides variants of albumin fusion proteins that have a functional activity (e.g., biological activity and/or therapeutic activity) that corresponds to one or more biological and/or therapeutic activities of the therapeutic protein corresponding to the therapeutic protein portion of the albumin fusion protein. In another embodiment, the invention provides variants of albumin fusion proteins that have a functional activity (e.g., biological activity and/or therapeutic activity) that corresponds to one or more biological and/or therapeutic activities of the therapeutic protein corresponding to the therapeutic protein portion of the albumin fusion protein. Such variants include deletions, insertions, inversions, repeats, and substitutions selected according to general rules known in the art so as have little effect on activity. Polynucleotides encoding such variants are also encompassed by the invention.

In preferred embodiments, the variants of the invention have conservative substitutions. By "conservative substitutions" is intended swaps within groups such as replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Guidance concerning how to make phenotypically silent amino acid substitutions is provided, for example, in Bowie et al., "Deciphering the Message in Protein Sequences Tolerance to Amino Acid Substitutions," Science 247:1306-

1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. See Cunningham and Wells, Science 244:1081-1085 (1989). The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly. Besides conservative amino acid substitution, variants of the present invention include (i) polypeptides containing substitutions of one or more of the non-conserved amino acid residues, where the substituted amino acid residues may or may not be one encoded by the genetic code, or (ii) polypeptides containing substitutions of one or more of the amino acid residues having a substituent group, or (iii) polypeptides which have been fused with or chemically conjugated to another compound, such as a compound to increase the stability and/or solubility of the polypeptide (for example, polyethylene glycol), (iv) polypeptide containing additional amino acids, such as, for example, an IgG Fc fusion region peptide. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. See Pinckard et al., *Clin. Exp. Immunol.* 2:331-340 (1967); Robbins et al., *Diabetes* 36: 838-845 (1987); Cleland et al., *Crit. Rev. Therapeutic Drug Carrier Systems* 10:307-377 (1993).

In specific embodiments, the polypeptides of the invention comprise, or alternatively, consist of, fragments or variants of the amino acid sequence of an albumin fusion protein, the amino acid sequence of a therapeutic protein and/or human serum albumin, wherein the fragments or variants have about 1-about 5, about 5-about 10, about 5-about 25, about 5-about 50, about 10-about 50 or about 50-about 150, amino acid residue additions, substitutions, and/or deletions when compared to the reference amino acid sequence. In preferred embodiments, the amino acid substitutions are conservative. Nucleic acids encoding these polypeptides are also encompassed by the invention.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N.Y. Acad. Sci. 663:48-62 (1992)).

Functional Activity

"A polypeptide having functional activity" refers to a polypeptide capable of displaying one or more known functional activities associated with the full-length, pro-protein, and/or mature form of a therapeutic protein. Such functional activities include, but are not limited to, biological activity, antigenicity [ability to bind (or compete with a polypeptide for binding) to an anti-polypeptide antibody], immunogenicity (ability to generate antibody which binds to a specific polypeptide of the invention), ability to form multimers with polypeptides of the invention, and ability to bind to a receptor or ligand for a polypeptide.

"A polypeptide having biological activity" refers to a polypeptide exhibiting activity similar to, but not necessarily identical to, an activity of a therapeutic protein of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention).

In preferred embodiments, an albumin fusion protein of the invention has at least one biological and/or therapeutic activity associated with the therapeutic protein portion (or fragment or variant thereof) when it is not fused to albumin.

The albumin fusion proteins of the invention can be assayed for functional activity (e.g., biological activity) using or routinely modifying assays known in the art, as well as assays described herein. Additionally, one of skill in the art may routinely assay fragments of a therapeutic protein corresponding to a therapeutic protein portion of an albumin fusion protein. Further, one of skill in the art may routinely assay fragments of an albumin protein corresponding to an albumin protein portion of an albumin fusion protein, for activity using assays known in the art and/or as described in the Examples section below.

In a preferred embodiment, where a binding partner (e.g., a receptor or a ligand) of a therapeutic protein is identified, binding to that binding partner by an albumin fusion protein which comprises that therapeutic protein as the therapeutic protein portion of the fusion can be assayed, e.g., by means well-known in the art, such as, for example, reducing and non-reducing gel chromatography, protein affinity chromatography, and affinity blotting. See generally, Phizicky et al., Microbiol. Rev. 59:94-123 (1995). In another embodiment, the ability of physiological correlates of an albumin fusion protein to bind to a substrate(s) of the therapeutic polypeptide corresponding to the therapeutic protein portion of the fusion can be routinely assayed using techniques known in the art.

In an alternative embodiment, where the ability of an albumin fusion protein to multimerize is being evaluated, association with other components of the multimer can be assayed, e.g., by means well-known in the art, such as, for example, reducing and non-reducing gel chromatography, protein affinity chromatography, and affinity blotting. See generally, Phizicky et al., supra.

The binding affinity of an albumin fusion protein to a receptor for the therapeutic protein and the off-rate of an albumin fusion protein-receptor interaction can be determined by competitive binding assays. One example of a competitive binding assay is a radioimmunoassay comprising the incubation of labeled albumin fusion protein (e.g., $^3$H or $^{125}$I) with a receptor for the therapeutic protein in the presence of increasing amounts of unlabeled fusion protein, and the detection of the bound fusion protein to the receptor. The affinity of the albumin fusion protein for a specific receptor and the binding off-rates can be determined from the data by Scatchard plot analysis. Competition with a second protein that binds the same receptor as the albumin fusion protein, can also be determined using radioimmunoassays. In this case, the protein, antigen or epitope is incubated with an albumin fusion protein conjugated to a labeled compound (e.g., $^3$H or $^{125}$I) in the presence of increasing amounts of an unlabeled second protein that binds the same protein, antigen, or epitope as the albumin fusion protein of the invention.

In a preferred embodiment, BIAcore kinetic analysis is used to determine the binding on and off rates of albumin fusion proteins of the invention to a protein, antigen or epitope. BIAcore kinetic analysis comprises analyzing the binding and dissociation of albumin fusion proteins, or specific polypeptides, antigens or epitopes from chips with immobilized specific polypeptides, antigens or epitopes or albumin fusion proteins, respectively, on their surface.

Albumin

As described above, an albumin fusion protein of the invention comprises at least a fragment or variant of a therapeutic protein and at least a fragment or variant of human serum albumin, which are associated with one another, preferably by genetic fusion.

An additional embodiment comprises at least a fragment or variant of a therapeutic protein and at least a fragment or variant of human serum albumin, which are linked to one another by chemical conjugation.

The terms, human serum albumin (HSA) and human albumin (HA) are used interchangeably herein. The terms, "albumin" and "serum albumin" are broader, and encompass human serum albumin (and fragments and variants thereof) as well as albumin from other species (and fragments and variants thereof).

As used herein, "albumin" refers collectively to albumin protein or amino acid sequence, or an albumin fragment or variant, having one or more functional activities (e.g., biological activities) of albumin. In particular, "albumin" refers to human albumin or fragments thereof (see for example, EP 201 239, EP 322 094, WO 97/24445, WO 95/23857) especially the mature form of human albumin as shown in FIG. 1A-D, or albumin from other vertebrates or fragments thereof, or analogs or variants of these molecules or fragments thereof.

In preferred embodiments, the human serum albumin protein used in the albumin fusion proteins of the invention contains one or both of the following sets of point mutations with reference to the sequence of albumin (FIG. 1A-D): Leu-407 to Ala, Leu-408 to Val, Val-409 to Ala, and Arg-410 to Ala; or Arg-410 to A, Lys-413 to Gln, and Lys-414 to Gln (see, e.g., International Publication No. WO 95/23857, hereby incorporated in its entirety by reference herein). In even more preferred embodiments, albumin fusion proteins of the invention that contain one or both of above-described sets of point mutations have improved stability/resistance to yeast Yap3p proteolytic cleavage, allowing increased production of recombinant albumin fusion proteins expressed in yeast host cells.

As used herein, a portion of albumin sufficient to prolong the therapeutic activity or shelf-life of the therapeutic protein refers to a portion of albumin sufficient in length or structure to stabilize or prolong the therapeutic activity of the protein so that the shelf life of the therapeutic protein portion of the albumin fusion protein is prolonged or extended compared to the shelf-life in the non-fusion state. The albumin portion of the albumin fusion proteins may comprise the full length of the HA sequence as described above, or may include one or more fragments thereof that are capable of stabilizing or prolonging the therapeutic activity. Such fragments may be of 10 or more amino acids in length or may include about 15, 20, 25, 30, 50, or more contiguous amino acids from the HA sequence or may include part or all of specific domains of HA. For instance, one or more fragments of HA spanning the first two immunoglobulin-like domains may be used. In a preferred embodiment, the HA fragment is the mature form of HA.

The albumin portion of the albumin fusion proteins of the invention may be a variant of normal HA. The therapeutic protein portion of the albumin fusion proteins of the invention may also be variants of the therapeutic proteins as described herein. The term "variants" includes insertions, deletions and substitutions, either conservative or non conservative, where such changes do not substantially alter one or more of the oncotic, useful ligand-binding and non-immunogenic properties of albumin, or the active site, or active domain which confers the therapeutic activities of the therapeutic proteins.

In particular, the albumin fusion proteins of the invention may include naturally occurring polymorphic variants of human albumin and fragments of human albumin, for example those fragments disclosed in EP 322 094 (namely HA (Pn), where n is 369 to 419). The albumin may be derived from any vertebrate, especially any mammal, for example human, cow, sheep, or pig. Non-mammalian albumins include, but are not limited to, hen and salmon. The albumin portion of the albumin fusion protein may be from a different animal than the therapeutic protein portion.

Generally speaking, an HA fragment or variant will be at least 100 amino acids long, preferably at least 150 amino acids long. The HA variant may consist of or alternatively comprise at least one whole domain of HA, for example domains 1 (amino acids 1-194 of albumin (FIG. 1A-D)), domain 2 (amino acids 195-387 of albumin (FIG. 1A-D)), domain 3 (amino acids 388-585 of albumin (FIG. 1A-D)), domains 1 and 2 (1-387 of albumin (FIG. 1A-D)), domains 2 and 3 (195-585 of albumin (FIG. 1A-D)) or domains 1 and 3 (amino acids 1-194 of albumin (FIG. 1A-D) and amino acids 388-585 of albumin (FIG. 1A-D)). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

Preferably, the albumin portion of an albumin fusion protein of the invention comprises at least one subdomain or domain of HA or conservative modifications thereof. If the fusion is based on subdomains, some or all of the adjacent linker is preferably used to link to the therapeutic protein moiety.

Therapeutic/Prophylactic Administration and Composition

The invention provides methods of treatment, inhibition and prophylaxis by administration to a subject of an effective amount of a compound or pharmaceutical composition of the invention. In a preferred embodiment, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Various delivery systems are known and can be used to administer a compound of the invention. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein of the invention, care must be taken to use materials to which the protein does not absorb.

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency-of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Albumin Fusion Proteins

The present invention relates generally to albumin fusion proteins and methods of treating, preventing, or ameliorating diseases or disorders. As used herein, "albumin fusion protein" refers to a protein formed by the fusion of at least one molecule of albumin (or a fragment or variant thereof) to at least one molecule of a therapeutic protein (or fragment or variant thereof). An albumin fusion protein of the invention comprises at least a fragment or variant of a therapeutic protein and at least a fragment or variant of human serum albumin, which are associated with one another, preferably by genetic fusion (i.e., the albumin fusion protein is generated by translation of a nucleic acid in which a polynucleotide encoding all or a portion of a therapeutic protein is joined in-frame with a polynucleotide encoding all or a portion of albumin) or to one another. The therapeutic protein and albumin protein, once part of the albumin fusion protein, may each be referred to as a "portion," "region" or "moiety" of the albumin fusion protein.

In a preferred embodiment, the invention provides an albumin fusion protein encoded by a polynucleotide or albumin fusion construct. Polynucleotides encoding these albumin fusion proteins are also encompassed by the invention.

Preferred albumin fusion proteins of the invention, include, but are not limited to, albumin fusion proteins encoded by a nucleic acid molecule comprising, or alternatively consisting of, a polynucleotide encoding at least one molecule of albumin (or a fragment or variant thereof) joined in frame to at least one polynucleotide encoding at least one molecule of a therapeutic protein (or fragment or variant thereof); a nucleic acid molecule comprising, or alternatively consisting of, a polynucleotide encoding at least one molecule of albumin (or a fragment or variant thereof) joined in frame to at least one polynucleotide encoding at least one molecule of a therapeutic protein (or fragment or variant thereof) generated as described in the Examples; or a nucleic acid molecule comprising, or alternatively consisting of, a polynucleotide encoding at least one molecule of albumin (or a fragment or variant thereof) joined in frame to at least one polynucleotide encoding at least one molecule of a therapeutic protein (or fragment or variant thereof), further comprising, for example, one or more of the following elements: (1) a functional self-replicating vector (including but not limited to, a shuttle vector, an expression vector, an integration vector, and/or a replication system), (2) a region for initiation of transcription (e.g., a promoter region, such as for example, a regulatable or inducible promoter, a constitutive promoter), (3) a region for termination of transcription, (4) a leader sequence, and (5) a selectable marker.

In one embodiment, the invention provides an albumin fusion protein comprising, or alternatively consisting of, a therapeutic protein (e.g., insulin or an insulin analog) and a serum albumin protein. In other embodiments, the invention provides an albumin fusion protein comprising, or alternatively consisting of, a biologically active and/or therapeutically active fragment of a therapeutic protein and a serum albumin protein. In other embodiments, the invention provides an albumin fusion protein comprising, or alternatively consisting of, a biologically active and/or therapeutically active variant of a therapeutic protein and a serum albumin protein. In preferred embodiments, the serum albumin protein component of the albumin fusion protein is the mature portion of serum albumin.

In further embodiments, the invention provides an albumin fusion protein comprising, or alternatively consisting of, a therapeutic protein, and a biologically active and/or therapeutically active fragment of serum albumin. In further embodiments, the invention provides an albumin fusion protein comprising, or alternatively consisting of, a therapeutic protein and a biologically active and/or therapeutically active variant of serum albumin. In preferred embodiments, the therapeutic protein portion of the albumin fusion protein is the mature portion of the therapeutic protein.

In further embodiments, the invention provides an albumin fusion protein comprising, or alternatively consisting of, a biologically active and/or therapeutically active fragment or variant of a therapeutic protein and a biologically active and/or therapeutically active fragment or variant of serum albumin. In preferred embodiments, the invention provides an albumin fusion protein comprising, or alternatively consisting of, the mature portion of a therapeutic protein and the mature portion of serum albumin.

Preferably, the albumin fusion protein comprises HA as the N-terminal portion, and a therapeutic protein as the C-terminal portion. Alternatively, an albumin fusion protein comprising HA as the C-terminal portion, and a therapeutic protein as the N-terminal portion may also be used.

In other embodiments, the albumin fusion protein has a therapeutic protein fused to both the N-terminus and the C-terminus of albumin. In a preferred embodiment, the therapeutic proteins fused at the N- and C-termini are the same therapeutic proteins. In an alternative preferred embodiment, the therapeutic proteins fused at the N- and C-termini are different therapeutic proteins. In another preferred embodiment, the therapeutic proteins fused at the N- and C-termini are different therapeutic proteins which may be used to treat or prevent the same or a related disease, disorder, or condition. In another preferred embodiment, the therapeutic proteins fused at the N- and C-termini are different therapeutic proteins which may be used to treat, ameliorate, or prevent diseases or disorders which are known in the art to commonly occur in patients simultaneously, concurrently, or consecutively, or which commonly occur in patients in association with one another.

Albumin fusion proteins of the invention encompass proteins containing one, two, three, four, or more molecules of a given therapeutic protein X or variant thereof fused to the N- or C-terminus of an albumin fusion protein of the invention, and/or to the N- and/or C-terminus of albumin or variant thereof. Molecules of a given therapeutic protein X or variants thereof may be in any number of orientations, including, but not limited to, a 'head to head' orientation (e.g., wherein the N-terminus of one molecule of a therapeutic protein X is fused to the N-terminus of another molecule of the therapeutic protein X), or a 'head to tail' orientation (e.g., wherein the C-terminus of one molecule of a therapeutic protein X is fused to the N-terminus of another molecule of therapeutic protein X). In one embodiment, one, two, three, four, five, or more tandemly oriented therapeutic molecules having insulin activity are fused to the N- or C-terminus of albumin or variant thereof.

Albumin fusion proteins of the invention further encompass proteins containing one, two, three, four, or more molecules of a given therapeutic protein having insulin activity or variant thereof fused to the N- or C-terminus of an albumin fusion protein of the invention, and/or to the N- and/or C-terminus of albumin or variant thereof, wherein the molecules are joined through peptide linkers. Examples include those peptide linkers described in U.S. Pat. No. 5,073,627 (hereby incorporated by reference). Albumin fusion proteins comprising multiple therapeutic proteins having insulin activity separated by peptide linkers may be produced using conventional recombinant DNA technology. Linkers are particularly important when fusing a small peptide to the large HSA molecule. The peptide itself can be a linker by fusing tandem copies of the peptide or other known linkers can be used. Constructs that incorporate linkers are described in the Examples. In one embodiment, one, two, three, four, five, or more tandemly oriented therapeutic molecules having insulin activity are fused to the N- or C-terminus of albumin or variant thereof.

Further, albumin fusion proteins of the invention may also be produced by fusing a therapeutic protein X or variants thereof to the N-terminal and/or C-terminal of albumin or variants thereof in such a way as to allow the formation of intramolecular and/or intermolecular multimeric forms. In one embodiment of the invention, albumin fusion proteins may be in monomeric or multimeric forms (i.e., dimers, trimers, tetramers and higher multimers). In a further embodiment of the invention, the therapeutic protein portion of an albumin fusion protein may be in monomeric form- or multimeric form (i.e., dimers, trimers, tetramers and higher multimers). In a specific embodiment, the therapeutic protein portion of an albumin fusion protein is in multimeric form (i.e., dimers, trimers, tetramers and higher multimers), and the albumin protein portion is in monomeric form.

In addition to albumin fusion protein in which the albumin portion is fused N-terminal and/or C-terminal of the therapeutic protein portion, albumin fusion proteins of the invention may also be produced by inserting the therapeutic protein or peptide of interest into an internal region of HA. For instance, within the protein sequence of the HA molecule a number of loops or turns exist between the end and beginning of alpha-helices, which are stabilized by disulphide bonds. The loops, as determined from the crystal structure of HA (PDB identifiers 1AO6, 1BJ5, 1BKE, 1BM0, 1E7E to 1E71 and 1UOR) for the most part extend away from the body of the molecule. These loops are useful for the insertion, or internal fusion, of therapeutically active peptides, particularly those requiring a secondary structure to be functional, or therapeutic proteins, to essentially generate an albumin molecule with specific biological activity.

Loops in human albumin structure into which peptides or polypeptides may be inserted to generate albumin fusion proteins of the invention include: Val54-Asn61, Thr76-Asp89, Ala92-Glu100, Gln170-Ala176, His 247-Glu252, Glu266-Glu277, Glu 280-His288, Ala362-Glu368, Lys439-Pro447, Val462-Lys475, Thr478-Pro486, and Lys560-Thr566. In more preferred embodiments, peptides or polypeptides are inserted into the Val54-Asn61, Gln170-Ala176, and/or Lys560-Thr566 loops of mature human albumin ((FIG. 1A-D).

Peptides to be inserted may be derived from either phage display or synthetic peptide libraries screened for specific biological activity or from the active portions of a molecule with the desired function. Additionally, random peptide libraries may be generated within particular loops or by insertions of randomized peptides into particular loops of the HA molecule and in which all possible combinations of amino acids are represented.

Such library(s) could be generated on HA or domain fragments of HA by one of the following methods: randomized mutation of amino acids within one or more peptide loops of HA or HA domain fragments. Either one, more or all the residues within a loop could be mutated in this manner; replacement of, or insertion into one or more loops of HA or HA domain fragments (i.e., internal fusion) of a randomized peptide(s) of length Xn (where X is an amino acid and n is the number of residues; N-, C- or N- and C-terminal peptide/protein fusions in addition to (a) and/or (b).

The HA or HA domain fragment may also be made multifunctional by grafting the peptides derived from different screens of different loops against different targets into the same HA or HA domain fragment.

In preferred embodiments, peptides inserted into a loop of human serum albumin are peptide fragments or peptide variants of the therapeutic proteins. More particularly, the invention encompasses albumin fusion proteins which comprise peptide fragments or peptide variants at least 7 at least 8, at least 9, at least 10, at least 11, at least 12, at least 13, at least 14, at least 15, at least 20, at least 25, at least 30, at least 35, or at least 40 amino acids in length inserted into a loop of human serum albumin. The invention also encompasses albumin fusion proteins which comprise peptide fragments or peptide variants at least 7 at least 8, at least 9, at least 10, at least 11, at least 12, at least 13, at least 14, at least 15, at least 20, at least 25, at least 30, at least 35, or at least 40 amino acids fused to the N-terminus of human serum albumin. The invention also encompasses albumin fusion proteins which comprise peptide fragments or peptide variants at least 7 at least 8, at least 9, at least 10, at least 11, at least 12, at least 13, at least 14, at least 15, at least 20, at least 25, at least 30, at least 35, or at least 40 amino acids fused to the C-terminus of human serum albumin.

Generally, the albumin fusion proteins of the invention may have one HA-derived region and one therapeutic protein-derived region. Multiple regions of each protein, however, may be used to make an albumin fusion protein of the invention. Similarly, more than one therapeutic protein may be used to make an albumin fusion protein of the invention. For instance, a therapeutic protein may be fused to both the N- and C-terminal ends of the HA. In such a configuration, the therapeutic protein portions may be the same or different therapeutic protein molecules. The structure of bifunctional albumin fusion proteins may be represented as: X-HA-Y or Y-HA-X.

Bi- or multi-functional albumin fusion proteins may also be prepared to target the therapeutic protein portion of a fusion to a target organ or cell type via protein or peptide at the opposite terminus of HA.

As an alternative to the fusion of known therapeutic molecules, the peptides could be obtained by screening libraries constructed as fusions to the N-, C- or N- and C-termini of HA, or domain fragment of HA, of typically 6, 8, 12, 20 or 25 or Xn (where X is an amino acid (aa) and n equals the number of residues) randomized amino acids, and in which all possible combinations of amino acids were represented. A particular advantage of this approach is that the peptides may be selected in situ on the HA molecule and the properties of the peptide would therefore be as selected for rather than, potentially, modified as might be the case for a peptide derived by any other method then being attached to HA.

Additionally, the albumin fusion proteins of the invention may include a linker peptide between the fused portions to provide greater physical separation between the moieties and thus maximize the accessibility of the therapeutic protein portion, for instance, for binding to its cognate receptor. The linker peptide may consist of amino acids such that it is flexible or more rigid.

The linker sequence may be cleavable by a protease or chemically to yield the therapeutic molecule related moiety. Preferably, the protease is one which is produced naturally by the host, for example the S. cerevisiae protease kex2 or equivalent proteases.

Therefore, as described above, the albumin fusion proteins of the invention may have the following formula R1-L-R2; R2-L-R1; or R1-L-R2-L-R1, wherein R1 is at least one therapeutic protein, peptide or polypeptide sequence, and not necessarily the same therapeutic protein, L is a linker and R2 is a serum albumin sequence. For example R1 may include insulin, an insulin analog, or a fragment or variant of insulin having insulin activity.

In preferred embodiments, Albumin fusion proteins of the invention comprising a therapeutic protein have extended shelf life compared to the shelf life the same therapeutic protein when not fused to albumin. Shelf-life typically refers to the time period over which the therapeutic activity of a therapeutic protein in solution or in some other storage formulation, is stable without undue loss of therapeutic activity. Many of the therapeutic proteins are highly labile in their unfused state. As described below, the typical shelf-life of these therapeutic proteins is markedly prolonged upon incorporation into the albumin fusion protein of the invention.

Albumin fusion proteins of the invention with "prolonged" or "extended" shelf-life exhibit greater therapeutic activity relative to a standard that has been subjected to the same storage and handling conditions. The standard may be the unfused full-length therapeutic protein. When the therapeutic protein portion of the albumin fusion protein is an analog, a variant, or is otherwise altered or does not include the complete sequence for that protein, the prolongation of therapeutic activity may alternatively be compared to the unfused equivalent of that analog, variant, altered peptide or incomplete sequence. As an example, an albumin fusion protein of the invention may retain greater than about 100% of the therapeutic activity, or greater than about 105%, 110%, 120%, 130%, 150% or 200% of the therapeutic activity of a standard when subjected to the same storage and handling conditions as the standard when compared at a given time point.

Shelf-life may also be assessed in terms of therapeutic activity remaining after storage, normalized to therapeutic activity when storage began. Albumin fusion proteins of the invention with prolonged or extended shelf-life as exhibited by prolonged or extended therapeutic activity may retain greater than about 50% of the therapeutic activity, about 60%, 70%, 80%, or 90% or more of the therapeutic activity of the equivalent unfused therapeutic protein when subjected to the same conditions. For example, as discussed in Example 38, an albumin fusion protein of the invention comprising hGH fused to the full length HA sequence may retain about 80% or more of its original activity in solution for periods of up to 5 weeks or more under various temperature conditions.

Insulin-Albumin Fusion Proteins

A single-chain insulin/albumin fusion protein suitable for clinical evaluation for the treatment of diabetes mellitus has been identified. Selection of the lead required identification of a composition with suitable pharmacologic activity, safety profile (mitogenicity), and production yields feasible for commercial scale manufacture. Selection of the lead was the result of a very large screening effort in which more than 40 different compositions were evaluated. Activity, production yield, and potential toxicity (mitogenic activity) all varied widely among different compositions.

Because yeast do not produce the enzymes needed to process pro-insulin to insulin, only a single-chain insulin fusion protein can be manufactured in this system. Thus, it is unexpected that fusion of insulin to albumin would generate an active protein with activity as, in fact, attachment of wild-type insulin to albumin results in an inactive protein, one which contains a full-length unprocessed insulin. To overcome this problem, eight (8) different non-cleavable C-peptide compositions were evaluated as part of an insulin albumin fusion protein. The yield of these proteins and their metabolic activity as well as there mitogenic activity varied widely (Table C).

TABLE B

Albulin Components Evaluated

| Component | Purpose | Conclusions |
|---|---|---|
| Signal peptide | Effects yield of protein | 2 compositions were evaluated, best signal peptide is dependent on fusion protein composition in non-obvious manner |
| Leader peptide | Effects yield of protein and may influence folding of insulin | 3 compositions were evaluated, best leader peptide is dependent on fusion protein composition in non-obvious manner |
| C-peptide | Antimicrobial peptide, not active as fusion protein | 8 C-peptide compositions were evaluated, composition affected metabolic and mitogenic activity in unpredictable |

TABLE B-continued

Albulin Components Evaluated

| Component | Purpose | Conclusions |
|---|---|---|
| Orientation (HSA-insulin, insulin-HAS) | Influenced yield and activity | manner N-terminal fusion of insulin to HSA was best activity and best yield. No way to predict ahead of time |

The final product selected was (from N-terminus to C-terminus): HSA signal peptide, RSLDKR (SEQ ID NO:28) leader peptide, native B-chain, GGGPGKR C-peptide (SEQ ID NO:29), native A-chain, HSA. This protein was produced with a high yield and combined low mitogenic activity with high metabolic activity in vivo. Mitogenic activity is influenced by the C-peptide composition, low mitogenic activity is desirable since mitogenic activity is considered a safety (cancer) risk.

A particular embodiment of the invention comprises a DNA construct encoding a signal sequence effective for directing secretion in yeast, particularly a yeast-derived signal sequence (especially one which is homologous to the yeast host), and the fused molecule of the first aspect of the invention, there being no yeast-derived pro sequence between the signal and the mature polypeptide.

The *Saccharomyces cerevisiae* invertase signal is a preferred example of a yeast-derived signal sequence.

Conjugates of the kind prepared by Poznansky et al., (FEBS Lett. 239:18 (1988)), in which separately-prepared polypeptides are joined by chemical cross-linking, are not contemplated.

The present invention also includes a cell, preferably a yeast cell transformed to express an albumin fusion protein of the invention. In addition to the transformed host cells themselves, the present invention also contemplates a culture of those cells, preferably a monoclonal (clonally homogeneous) culture, or a culture derived from a monoclonal

TABLE C

Insulin-HSA variants evaluated

| CID | Name | C-peptide Sequence | Leader peptide | N | C | Yield | Mitogenic Activity (in vitro) | Metabolic Activity (in vitro) | In Vivo Activity $AUEC_{0-48\ hrs}$ |
|---|---|---|---|---|---|---|---|---|---|
| 4560 | IN101CHY2 | GYGSSSRRAPQT (SEQ ID NO: 2) | HSA-GKex2 | | ● | Very low | ND | ND | ND |
| 2942 | IN101NHY3 | GYGSSSRRAPQT (SEQ ID NO: 2) | TA57 | ● | | ++++ 0.6 g | HIGH | ND | 1648** |
| 4568 | IN103CHY2 | GAGSSSRRAPQT (SEQ ID NO: 22) | HSA-GKex2 | | ● | Very low | ND | ND | ND |
| 4570 | IN103NHY2 | GAGSSSRRAPQT (SEQ ID NO: 22) | HSA-GKex2 | ● | | + 0.15 g/L | ND | LOW | 985* |
| 4593 | IN102CHY2 | GGGPQT (SEQ ID NO: 21) | HSA-GKex2 | | ● | Very low | ND | ND | ND |
| 4571 | IN107NHY2 | GGGPGAG (SEQ ID NO: 23) | HSA-GKex2 | ● | | ++ 0.2 g/L | ND | LOW | 1243* |
| 4504 | IN106NHY3 | NDEMPAD (SEQ ID NO: 20) | TA57 | ● | | + 0.15 g/L | ND | LOW | 648* |
| 4580 | IN106CHY2 | NDEMPAD (SEQ ID NO: 20) | HSA-GKex2 | | ● | + 0.15 g/L | ND | ND | ND |
| 2276 | IN100CHY0 | GGGPGKR (SEQ ID NO: 29) | HSA | | ● | +++ 0.5 g/L | ND | ND | 312** |
| 4519 | IN100CHY2(B5T) | GGGPGKR (SEQ ID NO: 29) | HSA-RKex2 | | ● | + 0.15 g/L | ND | ND | ND |
| 4502 | IN100CHY3 | GGGPGKR (SEQ ID NO: 29) | TA57 | | ● | + 0.15 g/L | ND | ND | 695** |
| 2278 | IN100NHY1 | GGGPGKR (SEQ ID NO: 29) | HSA-RKex2 | ● | | ++++ 0.6 g/L | LOW | HIGH | 1538* |
| 4518 | IN100NHY2(B5T) | GGGPGKR (SEQ ID NO: 29) | HSA-GKex2 | ● | | ++ 0.2 g/L | ND | ND | ND |
| 4499 | IN100NHY3 | GGGPGKR (SEQ ID NO: 29) | TA57 | ● | | ++++ 0.6 g/L | ND | ND | 411** |
| 4501 | IN100NHY3.1 | GGGPGKR (SEQ ID NO: 29) | TA57/Kex2 | ● | | +++ 0.3 g/L | ND | HIGH | 1427** |
| 4505 | IN104NHY3 | NPNLPRLVR (SEQ ID NO: 18) | TA57 | ● | | Very low | ND | LOW | ND |
| 4506 | IN105NHY3 | KDDNPNLPRLVR (SEQ ID NO: 19) | TA57 | ● | | Very low | ND | LOW | ND |

*10 mg/kg;
**20 mg/kg
ND, not determined;
CID, construct ID,
AUEC (Area under effect curve for glucose, difference in area under curves for vehicle vs. treatment)

Expression of Fusion Proteins

The albumin fusion proteins of the invention may be produced as recombinant molecules by secretion from yeast, a microorganism such as a bacterium, or a human or animal cell line. Preferably, the polypeptide is secreted from the host cells.

culture, in a nutrient medium. If the polypeptide is secreted, the medium will contain the polypeptide, with the cells, or without the cells if they have been filtered or centrifuged away. Many expression systems are known and may be used, including bacteria (for example *E. coli* and *Bacillus subtilis*), yeasts (for example *Saccharomyces cerevisiae, Kluyvero-*

*myces lactis* and *Pichia pastoris*, filamentous fungi (for example *Aspergillus*), plant cells, animal cells and insect cells.

Preferred yeast strains to be used in the production of albumin fusion proteins are D88, DXY1 and BXP10. D88 [leu2-3, leu2-122, can1, pra1, ubc4] is a derivative of parent strain AH22his+ (also known as DB1; see, e.g., Sleep et al. Biotechnology 8:42-46 (1990)). The strain contains a leu2 mutation which allows for auxotropic selection of 2 micron-based plasmids that contain the LEU2 gene. D88 also exhibits a derepression of PRB1 in glucose excess. The PRB1 promoter is normally controlled by two checkpoints that monitor glucose levels and growth stage. The promoter is activated in wild type yeast upon glucose depletion and entry into stationary phase. Strain D88 exhibits the repression by glucose but maintains the induction upon entry into stationary phase. The PRA1 gene encodes a yeast vacuolar protease, YscA endoprotease A, that is localized in the ER. The UBC4 gene is in the ubiquitination pathway and is involved in targeting short lived and abnormal proteins for ubiquitin dependant degradation. Isolation of this ubc4 mutation was found to increase the copy number of an expression plasmid in the cell and cause an increased level of expression of a desired protein expressed from the plasmid (see, e.g., International Publication No. WO 99/00504, hereby incorporated in its entirety by reference herein).

DXY1, a derivative of D88, has the following genotype: [leu2-3, leu2-122, can1, pra1, ubc4, ura3::yap3]. In addition to the mutations isolated in D88, this strain also has a knockout of the YAP3 protease. This protease causes cleavage of mostly di-basic residues (RR, RK, KR, KK) but can also promote cleavage at single basic residues in proteins. Isolation of this yap3 mutation resulted in higher levels of full length HSA production (see, e.g., U.S. Pat. No. 5,965,386 and Kerry-Williams et al., Yeast 14:161-169 (1998), hereby incorporated in their entireties by reference herein).

BXP10 has the following genotype: leu2-3, leu2-122, can1, pra1, ubc4, ura3, yap3::URA3, lys2, hsp150::LYS2, pmt1::URA3. In addition to the mutations isolated in DXY1, this strain also has a knockout of the PMT1 gene and the HSP150 gene. The PMT1 gene is a member of the evolutionarily conserved family of dolichyl-phosphate-D-mannose protein O-mannosyltransferases (Pmts). The transmembrane topology of Pmt1p suggests that it is an integral membrane protein of the endoplasmic reticulum with a role in O-linked glycosylation. This mutation serves to reduce/eliminate O-linked glycosylation of HSA fusions (see, e.g., International Publication No. WO 00/44772, hereby incorporated in its entirety by reference herein). Studies revealed that the Hsp150 protein is inefficiently separated from rHA by ion exchange chromatography. The mutation in the HSP150 gene removes a potential contaminant that has proven difficult to remove by standard purification techniques. See, e.g., U.S. Pat. No. 5,783,423, hereby incorporated in its entirety by reference herein.

The desired protein is produced in conventional ways, for example from a coding sequence inserted in the host chromosome or on a free plasmid. The yeasts are transformed with a coding sequence for the desired protein in any of the usual ways, for example electroporation. Methods for transformation of yeast by electroporation are disclosed in Becker & Guarente (1990) Methods Enzymol. 194, 182.

Successfully transformed cells, i.e., cells that contain a DNA construct of the present invention, can be identified by well known techniques. For example, cells resulting from the introduction of an expression construct can be grown to produce the desired polypeptide. Cells can be harvested and lysed and their DNA content examined for the presence of the DNA using a method such as that described by Southern (1975) J. Mol. Biol. 98, 503 or Berent et al. (1985) Biotech. 3, 208. Alternatively, the presence of the protein in the supernatant can be detected using antibodies.

Useful yeast plasmid vectors include pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, 7RP1, LEU2 and URA3. Plasmids pRS413-416 are Yeast Centromere plasmids (Ycps).

Preferred vectors for making albumin fusion proteins for expression in yeast include pPPC0005, pScCHSA, pSc-NHSA, and pC4:HSA which are described in detail in Example 1. FIG. 2 shows a map of the pPPC0005 plasmid that can be used as the base vector into which polynucleotides encoding therapeutic proteins may be cloned to form HA-fusions. It contains a PRB1 *S. cerevisiae* promoter (PRB1p), a Fusion leader sequence (FL), DNA encoding HA (rHA) and an ADH1 *S. cerevisiae* terminator sequence. The sequence of the fusion leader sequence consists of the first 19 amino acids of the signal peptide of human serum albumin and the last five amino acids of the mating factor alpha 1 promoter (SLDKR, see EP-A-387 319 which is hereby incorporated by reference in its entirety).

The plasmids, pPPC0005, pScCHSA, pScNHSA, and pC4:HSA were deposited on Apr. 11, 2001 at the American Type Culture Collection, 10801 University Boulevard, Manassas, Va. 20110-2209 and given accession numbers ATCC PTA-3278, PTA-3276, PTA-3279, and PTA-3277, respectively. Another vector useful for expressing an albumin fusion protein in yeast the pSAC35 vector which is described in Sleep et al., BioTechnology 8:42 (1990) which is hereby incorporated by reference in its entirety.

Another yeast promoter that can be used to express the albumin fusion protein is the MET25 promoter. See, for example, Dominik Mumburg, Rolf Muller and Martin Funk. Nucleic Acids Research, 1994, Vol. 22, No. 25, pp. 5767-5768. The Met25 promoter is 383 bases long (bases-382 to -1) and the genes expressed by this promoter are also known as Met15, Met17, and YLR303W. A preferred embodiment uses the sequence below including a Not I site for cloning at the 5' end, and an ATG start codon at the 3' end: 5 GCGGCCGCCGGATGCAAGGGTTCGAATCCCTTAG CTCTCATTATTTTTGCTTTTTCTCTTGAGGTCACAT-GATCGCAAAATGGCAAATG GCACGTGAAGCTGTC-GATATTGGGGAACTGTGGTGGTTGGCAAAT-GACTAATTAA GTTAGTCAAGGCGCCATCCTCATGAAAACTGTG-TAACATAATAACCGAAGTGTCG AAAAGGTGGCAC-CTTGTCCAATTGAACACGCTCGAT-GAAAAAAATAAGATATAT ATAAGGTTAAGTAAAGCGTCTGTTA-GAAAGGAAGTTTTTCCTTTTTCTTGCTCTCT TGTC-CATCTACTATTCCITCGTGTAATACAGGGTCGTCA-GATACATAGATA CAATTCTATTACCCCCATCCATACAATG (SEQ ID NO:30).

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or *E. coli* DNA polymerase I, enzymes that remove protruding, gamma-single-stranded termini with their 3' 5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA in accordance with the invention, if, for example, HA variants are to be prepared, is to use the polymerase chain reaction as disclosed by Saiki et al. (1988) Science 239, 487-491. In this method the DNA to be enzymatically amplified is flanked by two specific oligonucleotide primers which themselves become incorporated into the amplified DNA. The specific primers may contain restriction endonuclease recognition sites which can be used for cloning into expression vectors using methods known in the art.

Exemplary genera of yeast contemplated to be useful in the practice of the present invention as hosts for expressing the albumin fusion proteins are *Pichia* (*Hansenula*), *Saccharomyces*, *Kluyveromyces*, *Candida*, *Torulopsis*, *Torulaspora*, *Schizosaccharomyces*, *Citeromyces*, *Pachysolen*, *Debaromyces*, *Metschunikowia*, *Rhodosporidium*, *Leucosporidium*, *Botryoascus*, *Sporidiobolus*, *Endomycopsis*, and the like. Preferred genera are those selected from the group consisting of *Saccharomyces*, *Schizosaccharomyces*, *Kluyveromyces*, *Pichia* and *Torulaspora*. Examples of *Saccharomyces* spp. are *S. cerevisiae*, *S. italicus* and *S. rouxii*.

Examples of *Kluyveromyces* spp. are *K. fragilis*, *K. lactis* and *K. marxianus*. A suitable *Torulaspora* species is *T. delbrueckii*. Examples of *Pichia* (*Hansenula*) spp. are *P. angusta* (formerly *H. polymorpha*), *P. anomala* (formerly *H. anomala*) and *P. pastoris*. Methods for the transformation of *S. cerevisiae* are taught generally in EP 251 744, EP 258 067 and WO 90/01063, all of which are incorporated herein by reference.

Preferred exemplary species of *Saccharomyces* include *S. cerevisiae*, *S. italicus*, *S. diastaticus*, and *Zygosaccharomyces rouxii*. Preferred exemplary species of *Kluyveromyces* include *K. fragilis* and *K. lactis*. Preferred exemplary species of *Hansenula* include *H. polymorpha* (now *Pichia angusta*), *H. anomala* (now *Pichia anomala*), and *Pichia capsulata*. Additional preferred exemplary species of *Pichia* include *P. pastoris*. Preferred exemplary species of *Aspergillus* include *A. niger* and *A. nidulans*. Preferred exemplary species of *Yarrowia* include *Y. lipolytica*. Many preferred yeast species are available from the ATCC. For example, the following preferred yeast species are available from the ATCC and are useful in the expression of albumin fusion proteins: *Saccharomyces cerevisiae* Hansen, teleomorph strain BY4743 yap3 mutant (ATCC Accession No. 4022731); *Saccharomyces cerevisiae* Hansen, teleomorph strain BY4743 hsp150 mutant (ATCC Accession No. 4021266); *Saccharomyces cerevisiae* Hansen, teleomorph strain BY4743 pmt1 mutant (ATCC Accession No. 4023792); *Saccharomyces cerevisiae* Hansen, teleomorph (ATCC Accession Nos. 20626; 44773; 44774; and 62995); *Saccharomyces diastaticus* Andrews et Gilliland ex van der Walt, teleomorph (ATCC Accession No. 62987); *Kluyveromyces lactis* (Dombrowski) van der Walt, teleomorph (ATCC Accession No. 76492); *Pichia angusta* (Teunisson et al.) Kurtzman, teleomorph deposited as *Hansenula polymorpha* de Morais et Maia, teleomorph (ATCC Accession No. 26012); *Aspergillus niger* van Tieghem, anamorph (ATCC Accession No. 9029); *Aspergillus niger* van Tieghem, anamorph (ATCC Accession No. 16404); *Aspergillus nidulans* (Eidam) Winter, anamorph (ATCC Accession No. 48756); and *Yarrowia lipolytica* (Wickerham et al.) van der Walt et von Arx, teleomorph (ATCC Accession No. 201847).

Suitable promoters for *S. cerevisiae* include those associated with the PGKI gene, GAL1 or GAL10 genes, CYCI, PHO5, TRPI, ADHI, ADH2, the genes for glyceraldehyde-3-phosphate dehydrogenase, hexokinase, pyruvate decarboxylase, phosphofructokinase, triose phosphate isomerase, phosphoglucose isomerase, glucokinase, alpha-mating factor pheromone, [a mating factor pheromone], the PRBI promoter, the GUT2 promoter, the GPDI promoter, and hybrid promoters involving hybrids of parts of 5' regulatory regions with parts of 5' regulatory regions of other promoters or with upstream activation sites (e.g. the promoter of EP-A-258 067).

Convenient regulatable promoters for use in *Schizosaccharomyces pombe* are the thiamine-repressible promoter from the nmt gene as described by Maundrell (1990) *J. Biol. Chem.*, 265, 10857-10864, and the glucose repressible jbpl gene promoter as described by Hoffman & Winston (1990) Genetics 124, 807-816.

Methods of transforming *Pichia* for expression of foreign genes are taught in, for example, Cregg et al. (1993), and various Phillips patents (e.g. U.S. Pat. No. 4,857,467, incorporated herein by reference), and *Pichia* expression kits are commercially available from Invitrogen BV, Leek, Netherlands, and Invitrogen Corp., San Diego, Calif. Suitable promoters include AOXI and AOX2. Gleeson et al. (1986), *J. Gen. Microbiol.*, 132, 3459-3465 include information on *Hansenula* vectors and transformation, suitable promoters being MOX1 and FMD1; whilst EP 361 991, Fleer et al. (1991) and other-publications from Rhone-Poulenc Rorer teach how to express foreign proteins in *Kluyveromyces* spp., a suitable promoter being PGKI.

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, i.e., may correspond to the promoter. Alternatively, they may be different in which case the termination signal of the *S. cerevisiae* ADHI gene is preferred.

The desired albumin fusion protein may be initially expressed with a secretion leader sequence, which may be any leader effective in the yeast chosen. Leaders useful in yeast include any of the following:

a) the MPIF-1 signal sequence (e.g., amino acids 1-21 of GenBank Accession number AAB51134) MKVS-VAALSCLMLVTALGSQA (SEQ ID NO:31)

b) the stanniocalcin signal sequence (MLQNSAVLLLL-VISASA) (SEQ ID NO:32)

c) the pre-pro region of the HSA signal sequence (e.g., MKWVTFISLLFLFSSAYSRGVFRR) (SEQ ID NO:33)

d) the pre region of the HSA signal sequence (e.g., MKWVTFISLLFLFSSAYS) (SEQ ID NO:34) or variants thereof, such as, for example, MKWVSFISLLFLFSSAYS (SEQ ID NO: 35), e) the invertase signal sequence (e.g., MLLQAFLFLLAGFAAKISA) (SEQ ID NO:36)

f) the yeast mating factor alpha signal sequence (e.g., MRFPSIFTAVLAFAASSALAAPVNYTTEDETAQIPAEAVIGYSDLEGDFDV AVLPFSNSTNNGLLFINTTIASIAAKEEGVSLEKR (SEQ ID NO:37) or MRFPSIFTAVLAFAASSALAAPVNTITEDETAQIPAEAVIGYSDLEGDFDV AVLPFSNSTNNGLLFINTTIASIAAKEEGVSLDKR) (SEQ ID NO:38)

g) *K. lactis* killer toxin leader sequence h) a hybrid signal sequence (e.g., MKWVSFISLLFLFSSAYSRSLEKR) (SEQ ID NO:3)

h) an HSA/MFalpha-1 hybrid signal sequence (also known as HSA/kex2) (e.g., MKWVSFISLLFLFSSAYSRSLDKR) (SEQ ID NO:4)

i) a *K. lactis* killer/MFalpha-1 fusion leader sequence (e.g., MNIFYIFLFLLSFVQGSLDKR) (SEQ ID NO:5)

j) the Immunoglobulin Ig signal sequence (e.g., MGWSCIILFLVATATGVHS) (SEQ ID NO:39)

k) the Fibulin B precursor signal sequence (e.g., MERAAPSRRVPLPLLLLGGLALLAAGVDA) (SEQ ID NO:40)

l) the clusterin precursor signal sequence (e.g., MMKTLLLFVGLLLTWESGQVLG) (SEQ ID NO:41)

m) the insulin-like growth factor-binding protein 4 signal sequence (e.g., MLPLCLVAALLLAAGPGPSLG) (SEQ ID NO:42)

n) variants of the pre-pro-region of the HSA signal sequence such as, for example, MKWVSFISLLFLFSSAYSRGVFRR (SEQ ID NO:6), MKWVTFISLLFLFAGVLG (SEQ ID NO:7), MKWVTFISLLFLFSGVLG (SEQ ID NO:8), MKWVTFISLLFLFGGVLG (SEQ ID NO:9); Modified HSA leader HSA MKWVTFISLLFLFAGVSG (SEQ ID NO:10); Modified HSA leader HSA MKWVTFISLLFLFGGVSG (SEQ ID NO:11); Modified HSA (A14) leader-MKWVTFISLLFLFAGVSG (SEQ ID NO:10); Modified HSA (S14) leader—MKWVTFISLLFLFSGVSG (SEQ ID NO:12), Modified HSA (G14) leader—MKWVTFLSLLFLFGGVSG (SEQ ID NO:13), or MKWVTFISLLFLFGGVLGDLHKS (SEQ ID NO:14).

o) a consensus signal sequence (MPTWAWWLFLVLLLALWAPARG) (SEQ ID NO:15)

p) acid phosphatase (PHO5) leader (e.g., MFKSVVYSILAASLANA) (SEQ ID NO:43)

q) the pre-sequence of MFoz-1 r) the pre-sequence of 0 glucanase (BGL2)

s) killer toxin leader t) the presequence of killer toxin u) *K. lactis* killer toxin prepro (29 amino acids; 16 amino acids of pre and 13 amino acids of pro) MNIFYIFLFLLSFVQGLEHTHRRGSLDKR (SEQ ID NO:16)

v) *S. diastaticus* glucoamylase II secretion leader sequence w) *S. carlsbergensis* alpha-galactosidase (MEL1) secretion leader sequence x) *Candida* glocoamylase leader sequence y) The hybrid leaders disclosed in EP-A-387 319 (herein incorporated by reference)

z) The hybrid leaders disclosed in EP-A-387 319 (herein incorporated by reference)

aa) the gp67 signal sequence (in conjunction with baculoviral expression systems) (e.g., amino acids 1-19 of GenBank Accession Number AAA72759) or bb) the natural leader of the therapeutic protein X;

cc) *S. cerevisiae* invertase (SUC2) leader, as disclosed in JP 62-096086 (granted as 911036516, herein incorporate by reference); or dd) Inulinase-MKLAYSLLLPLAGVSASVINYKR (SEQ ID NO:17).

ee) A modified TA57 propeptide leader variant #1-8 MKLKTVRSAVLSSLFASQVLGQPIDDTESQTTSV NLMADDTESAEATQTNSGGLDVVGLISMAKR (SEQ ID NO:44)

ff) A modified TA57 propeptide leader variant #2-9 MKLKTVRSAVLSSLFASQVLGQPIDDTESQTTS VNLMADDTESAFATQTNSGGLDVVGLISMAEEG EPKR (SEQ ID NO:45)

Additional Methods of Recombinant and Synthetic Production of Albumin Fusion Proteins The present invention also relates to vectors containing a polynucleotide encoding an albumin fusion protein of the present invention, host cells, and the production of albumin fusion proteins by synthetic and recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides encoding albumin fusion proteins of the invention may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418, glutamine synthase, or neomycin resistance for eukaryotic cell culture, and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, NSO, 293, and Bowes melanoma cells; and plant cells. Appropriate culture mediums and conditions for the above described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PA0815 (all available from Invitrogen, Carlbad, Calif.). Other suitable vectors will be readily apparent to the skilled artisan.

In one embodiment, polynucleotides encoding an albumin fusion protein of the invention may be fused to signal sequences which will direct the localization of a protein of the invention to particular compartments of a prokaryotic or eukaryotic cell and/or direct the secretion of a protein of the invention from a prokaryotic or eukaryotic cell. For example, in *E. coli*, one may wish to direct the expression of the protein to the periplasmic space. Examples of signal sequences or proteins (or fragments thereof) to which the albumin fusion proteins of the invention may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, polynucleotides albumin fusion proteins of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that may be fused to an albumin fusion protein of the invention in order to direct its secretion in mammalian cells include, but are not limited to:
a) the MPIF-1 signal sequence (e.g., amino acids 1-21 of GenBank Accession number AAB51134) MKVSVAALSCLMLVTALGSQA (SEQ ID NO:31)
b) the stanniocalcin signal sequence (MLQNSAVLLILLVISASA) (SEQ ID NO:46)
c) the pre-pro region of the HSA signal sequence (e.g., MKWVTFISLLFLFSSAYSRGVFRR) (SEQ ID NO:33)
d) the pre region of the HSA signal sequence (e.g., MKWVTFISLLFLFSSAYS) (SEQ ID NO:34) or variants thereof, such as, for example, MKWVSFISLLFLFSSAYS (SEQ ID NO:35),
e) the invertase signal sequence (e.g., MLLQAFLFLLAGFAAKISA) (SEQ ID NO:36)
f) the yeast mating factor alpha signal sequence (e.g., MRFPSIFTAVLAFAASSALAAPVNTTTEDETAQIPAEAVIGYSDLEGDFDVAVL PFSNSTNNGLLFINTTIASIAAKEEGVSLEKR (SEQ ID NO:47), or MRFPSIFTAVLAFAASSALAAPVNTTTEDETAQIPAEAVIGYSDLEGDFDVAVL PFSNSTNNGLLFINTTIASIAAKEEGVSLDKR) (SEQ ID NO:48)
g) *K. lactis* killer toxin leader sequence
h) a hybrid signal sequence (e.g., MKWVSFISLLFLFSSAYSRSLEKR) (SEQ ID NO:3)

i) an HSA/MFalpha-1 hybrid signal sequence (also known as HSA/kex2) (e.g., MKWVSFISLLFLFSSAYSRSLDKR) (SEQ ID NO:4)
j) a *K. lactis* killer/MFalpha-1 fusion leader sequence (e.g., MNIFYIFLFLLSFVQGSLDKR) (SEQ ID NO:5)
k) the Immunoglobulin Ig signal sequence (e.g., MGWSCIILFLVATATGVHS) (SEQ ID NO:39)
l) the Fibulin B precursor signal sequence (e.g., MERAAPSRRVPLPLLLLGGLALLAAGVDA) (SEQ ID NO:40)
m) the clusterin precursor signal sequence (e.g., MMKTLLLFVGLLLTWESGQVLG) (SEQ ID NO:41)
n) the insulin-like growth factor-binding protein 4 signal sequence (e.g., MLPLCLVAALLLAAGPGPSLG) (SEQ ID NO:42)
o) variants of the pre-pro-region of the HSA signal sequence such as, for example, 10 MKWVSFISLLFLFSSAYSRGVFRR (SEQ ID NO:6), MKWVTFISLLFLFAGVLG (SEQ ID NO:7), MKWVTFISLLFLFSGVLG (SEQ ID NO:8), MKWVTFISLLFLFGGVLG (SEQ ID NO:9), Modified HSA leader MKWVTFISLLFLFAGVSG (SEQ ID NO:10); Modified HSA leader MKWVTFISLLFLFGGVSG (SEQ ID NO:11); Modified HSA (A14) leader—MKWVTFISLLFLFAGVSG (SEQ ID NO:10); Modified HSA (S14) leader—MKWVTFISLLFLFSGVSG (SEQ ID NO:12), Modified HSA (G14) leader—MKWVTFISLLFLFGGVSG (SEQ ID NO:11), or MKWVTFISLLFLFGGVLGDLHKS (SEQ ID NO:14)
p) a consensus signal sequence (MPTWAWWLFLVLLLALWAPARG) (SEQ ID NO:15)
q) acid phosphatase (PHO5) leader (e.g., MFKSVVYSILAASLANA) (SEQ ID NO:43)
r) the pre-sequence of MFα-1
s) the pre-sequence of 0 glucanase (BGL2)
t) killer toxin leader
u) the presequence of killer toxin
v) *K. lactis* killer toxin prepro (29 amino acids; 16 amino acids of pre and 13 amino acids of pro) MNIFYIFLFLLSFVQGLEHTHRRGSLDKR (SEQ ID NO:16)
w) *S. diastaticus* glocoamylase II secretion leader sequence
x) *S. carlsbergensis* alpha-galactosidase (MEL1) secretion leader sequence
y) *Candida* glocoamylase leader sequence
z) The hybrid leaders disclosed in EP-A-387 319 (herein incorporated by reference)
aa) the gp67 signal sequence (in conjunction with baculoviral expression systems) (e.g., amino acids 1-19 of GenBank Accession Number AAA72759) or
bb) the natural leader of the therapeutic protein X;
cc) *S. cerevisiae* invertase (SUC2) leader, as disclosed in JP 62-096086 (granted as 911036516, herein incorporate by reference); or
dd) Inulinase MKLAYSLLLPLAGVSASVINYKR (SEQ ID NO:17).
ee) A modified TA57 propeptide leader variant #1-12 MKLKTVRSAVLSSLFASQVLGQPIDDTESQTTSV NLMADDTESAFATQTNSGGLDVVGLISMAKR (SEQ ID NO:49)
ff) A modified TA57 propeptide leader variant #2-13 MKLKTVRSAVLSSLFASQVLGQPIDDTESQTTSV NLMADDTESAFATQTNSGGLDVVGLISMAEEGEP KR (SEQ ID NO:50)

Vectors which use glutamine synthase (GS) or DBFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g., Chinese Hamster Ovary (CHO) cells) by providing additional inhibitor to prevent the functioning of the endogenous gene. A glutamine synthase expression system and components thereof are detailed in PCT publications: WO 87/04462; WO 86/05807; WO 89/01036; WO 89/10404; and WO 91/06657, which are hereby incorporated in their entireties by reference herein. Additionally, glutamine synthase expression vectors can be obtained from Lonza Biologics, Inc. (Portsmouth, N.H.). Expression and production of monoclonal antibodies using a GS expression system in murine myeloma cells is described in Bebbington et al., *Bio/technology*, 10:169 (1992) and in *Biblia and Robinson Biotechnol. Prog.*, 11:1 (1995), which are herein incorporated by reference.

The present invention also relates to host cells containing the above-described vector constructs described herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. A host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the nucleic acids and nucleic acid constructs of the invention into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., the coding sequence corresponding to a therapeutic protein may be replaced with an albumin fusion protein corresponding to the therapeutic protein), and/or to include genetic material (e.g., heterologous polynucleotide sequences such as for example, an albumin fusion protein of the invention corresponding to the therapeutic protein may be included). The genetic material operably associated with the endogenous polynucleotide may activate, alter, and/or amplify endogenous polynucleotides.

In addition, techniques known in the art may be used to operably associate heterologous polynucleotides (e.g., polynucleotides encoding an albumin protein, or a fragment or variant thereof) and/or heterologous control regions (e.g., promoter and/or enhancer) with endogenous polynucleotide sequences encoding a therapeutic protein via homologous recombination (see, e.g., U.S. Pat. No. 5,641,670, issued Jun. 24, 1997; International Publication Number WO 96/29411; International Publication Number WO 94/12650; Koller et al., *Proc. Natl. Acad. Sci. USA* 86:8932-8935 (1989); and Zijlstra et al., *Nature* 342:435-438 (1989), the disclosures of each of which are incorporated by reference in their entireties).

Albumin fusion proteins of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, hydrophobic charge interaction chromatography and lectin chromatography. Most preferably, high performance liquid chromatography ("HPLC") is employed for purification.

In preferred embodiments the albumin fusion proteins of the invention are purified using Anion Exchange Chromatography including, but not limited to, chromatography on Q-sepharose, DEAE sepharose, poros HQ, poros DEAE, Toyopearl Q, Toyopearl QAE, Toyopearl DEAE, Resource/Source Q and DEAE, Fractogel Q and DEAE columns.

In specific embodiments the albumin fusion proteins of the invention are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In specific embodiments the albumin fusion proteins of the invention are purified using Hydrophobic Interaction Chromatography including, but not limited to, Phenyl, Butyl, Methyl, Octyl, Hexyl-sepharose, poros Phenyl, Butyl, Methyl, Octyl, Hexyl, Toyopearl Phenyl, Butyl, Methyl, Octyl, Hexyl Resource/Source Phenyl, Butyl, Methyl, Octyl, Hexyl, Fractogel Phenyl, Butyl, Methyl, Octyl, Hexyl columns and their equivalents and comparables.

In specific embodiments the albumin fusion proteins of the invention are purified using Size Exclusion Chromatography including, but not limited to, sepharose S100, S200, S300, superdex resin columns and their equivalents and comparables.

In specific embodiments the albumin fusion proteins of the invention are purified using Affinity Chromatography including, but not limited to, Mimetic Dye affinity, peptide affinity and antibody affinity columns that are selective for either the HSA or the "fusion target" molecules.

In preferred embodiments albumin fusion proteins of the invention are purified using one or more Chromatography methods listed above. In other preferred embodiments, albumin fusion proteins of the invention are purified using one or more of the following Chromatography columns, Q sepharose FF column, SP Sepharose FF column, Q Sepharose High Performance Column, Blue Sepharose FF column, Blue Column, Phenyl Sepharose FF column, DEAE Sepharose FF, or Methyl Column.

Additionally, albumin fusion proteins of the invention may be purified using the process described in PCT International Publication WO 00/44772 which is herein incorporated by reference in its entirety. One of skill in the art could easily modify the process described therein for use in the purification of albumin fusion proteins of the invention.

Albumin fusion proteins of the present invention may be recovered from: products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, albumin fusion proteins of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express albumin fusion proteins of the invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. To metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See Ellis, S. B., et al., *Mol. Cell. Biol.* 5:1111-21 (1985); Koutz, P. J, et al., *Yeast* 5:167-77 (1989); Tschopp, J. F., et al., *Nucl. Acids Res.* 15:3859-76 (1987). Thus, a heterologous coding sequence, such as, for example, a polynucleotide of the present invention, under the transcriptional regulation of all or part of the AOXI regulatory sequence is expressed at exceptionally high levels in *Pichia* yeast grown in the presence of methanol.

In one example, the plasmid vector pPIC9K is used to express DNA encoding an albumin fusion protein of the invention, as set forth herein, in a *Pichea* yeast system essentially as described in "*Pichia* Protocols: Methods in Molecular Biology," D. R. Higgins and J. Cregg, eds. The Humana Press, Totowa, N.J., 1998. This expression vector allows expression and secretion of a polypeptide of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a polynucleotide encoding an albumin fusion protein of the present invention, may be achieved by cloning the heterologous polynucleotide of the invention into an expression vector such as, for example, pGAPZ or pGAPZalpha, and growing the yeast culture in the absence of methanol.

In addition, albumin fusion proteins of the invention can be chemically synthesized using techniques known in the art (e.g., see Creighton, 1983, *Proteins: Structures and Molecular Principles*, W.H. Freeman & Co., N.Y., and Hunkapiller et al., *Nature*, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses albumin fusion proteins of the present invention which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The albumin fusion proteins may also be modified with a detectable label, such as an enzymatic, fluorescent, isotopic or affinity label to allow for detection and isolation of the protein.

Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

In specific embodiments, albumin fusion proteins of the present invention or fragments or variants thereof are attached to macrocyclic chelators that associate with radiometal ions, including but not limited to, $^{177}$Lu, $^{90}$Y, $^{166}$Ho, and $^{153}$Sm, to polypeptides. In a preferred embodiment, the radiometal ion associated with the macrocyclic chelators is $^{111}$In. In another preferred embodiment, the radiometal ion associated with the macrocyclic chelator is $^{90}$Y. In specific embodiments, the macrocyclic chelator is 1,4,7,10-tetraaza-cyclododecane-N,N',N'',N'''-tetraacetic acid (DOTA). In other specific embodiments, DOTA is attached to an antibody of the invention or fragment thereof via linker molecule. Examples of linker molecules useful for conjugating DOTA to a polypeptide are commonly known in the art—see, for example, DeNardo et al., *Clin Cancer Res.*, 4(10): 2483-90 (1998); Peterson et al., *Bioconjug. Chem.*, 10(4): 553-7 (1999); and Zimmerman et al, *Nucl. Med. Biol.*, 26(8):943-50 (1999); which are hereby incorporated by reference in their entirety.

As mentioned, the albumin fusion proteins of the invention may be modified by either natural processes, such as post-translational processing, or by chemical modification techniques which are well known in the art. It will be appreciated that the same type of modification may be present in the same or varying degrees at several sites in a given polypeptide. Polypeptides of the invention may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., *Meth. Enzymol.* 182:626-646 (1990); Rattan et al., *Ann. NY. Acad. Sci.* 663:48-62 (1992)).

Albumin fusion proteins of the invention and antibodies that bind a therapeutic protein or fragments or variants thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Further, an albumin fusion protein of the invention may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, B-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. Techniques for conjugating such therapeutic moiety to proteins (e.g., albumin fusion proteins) are well known in the art.

Albumin fusion proteins may also be attached to solid supports, which are particularly useful for immunoassays or purification of polypeptides that are bound by, that bind to, or associate with albumin fusion proteins of the invention. Such solid supports include, but are not limited to, glass, cellulose, polyacrylamide, nylon, polystyrene, polyvinyl chloride or polypropylene.

Also provided by the invention are chemically modified derivatives of the albumin fusion proteins of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The albumin fusion proteins may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, about 500, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10,000, about 10,500, about 11,000, about 11,500, about 12,000, about 12,500, about 13,000, about 13,500, about 14,000, about 14,500, about 15,000, about 15,500, about 16,000, about 16,500, about 17,000, about 17,500, about 18,000, about 18,500, about 19,000, about 19,500, about 20,000, about 25,000, about 30,000, about 35,000, about 40,000, about 45,000, about 50,000, about 55,000, about 60,000, about 65,000, about 70,000, about 75,000, about 80,000, about 85,000, about 90,000, about 95,000, or about 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.*, 56:59-72 (1996); Vorobjev et al., *Nucleosides Nucleotides*, 18:2745-2750 (1999); and Caliceti et al., *Bioconjug. Chem.*, 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, such as, for example, the method disclosed in EP 0 401 384 (coupling PEG to G-CSF), herein incorporated by reference; see also Malik et al., *Exp. Hematol.*, 20:1028-1035 (1992), reporting pegylation of GM-CSF using tresyl chloride. For example, polyethylene glycol may be covalently bound through amino acid residues via reactive group, such as a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the albumin fusion proteins of the invention may be accomplished by any number of means. For example, polyethylene glycol may be attached to the albumin fusion protein either directly or by an intervening linker. Linkerless systems for attaching polyethylene glycol to proteins are described in Delgado et al., *Crit. Rev. Thera. Drug Carrier Sys.*, 9:249-304 (1992); Francis et al., *Intern. J. of Hematol.*, 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monomethoxy polyethylene glycol (MPEG) using tresylchloride (ClSO2CH2CF3). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoroethane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number of additional polyethylene glycol derivatives and reaction chemistries for attaching polyethylene glycol to proteins are described in International Publication No. WO 98/32466, the entire disclosure of which is incorporated herein by reference. Pegylated protein products produced using the reaction chemistries set out herein are included within the scope of the invention.

The number of polyethylene glycol moieties attached to each albumin fusion protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

The polypeptides of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

The presence and quantity of albumin fusion proteins of the invention may be determined using ELISA, a well known immunoassay known in the art. In one ELISA protocol that would be useful for detecting/quantifying albumin fusion proteins of the invention, comprises the steps of coating an ELISA plate with an anti-human serum albumin antibody, blocking the plate to prevent non-specific binding, washing the ELISA plate, adding a solution containing the albumin fusion protein of the invention (at one or more different concentrations), adding a secondary anti-therapeutic protein specific antibody coupled to a detectable label (as described herein or otherwise known in the art), and detecting the presence of the secondary antibody. In an alternate version of this protocol, the ELISA plate might be coated with the anti-therapeutic protein specific antibody and the labeled secondary reagent might be the anti-human albumin specific antibody.

Uses of the Polynucleotides

Each of the polynucleotides identified herein can be used in numerous ways as reagents. The following description should be considered exemplary and utilizes known techniques.

The polynucleotides of the present invention are useful to produce the albumin fusion proteins of the invention. As described in more detail below, polynucleotides of the invention (encoding albumin fusion proteins) may be used in recombinant DNA methods useful in genetic engineering to make cells, cell lines, or tissues that express the albumin fusion protein encoded by the polynucleotides encoding albumin fusion proteins of the invention.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. Additional non-limiting examples of gene therapy methods encompassed by the present invention are more thoroughly described elsewhere herein (see, e.g., the sections labeled "Gene Therapy," and Examples 63 and 64).

The albumin fusion proteins of the present invention are useful for diagnosis, treatment, prevention and/or prognosis of various disorders in mammals, preferably humans. Such disorders include, but are not limited to, those described herein under the section heading "Biological Activities," below.

Thus, the invention provides a diagnostic method of a disorder, which involves (a) assaying the expression level of a certain polypeptide in cells or body fluid of an individual using an albumin fusion protein of the invention; and (b) comparing the assayed polypeptide expression level with a standard polypeptide expression level, whereby an increase or decrease in the assayed polypeptide expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, albumin fusion proteins of the present invention can be used to treat or prevent diseases or conditions such as, for example, neural disorders, immune system disorders, muscular disorders, reproductive disorders, gastrointestinal disorders, pulmonary disorders, cardiovascular disorders, renal disorders, proliferative disorders, and/or cancerous diseases and conditions. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor supressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Transgenic Organisms

Transgenic organisms that express the albumin fusion proteins of the invention are also included in the invention. Transgenic organisms are genetically modified organisms into which recombinant, exogenous or cloned genetic material has been transferred. Such genetic material is often referred to as a transgene. The nucleic acid sequence of the transgene may include one or more transcriptional regulatory sequences and other nucleic acid sequences such as introns, that may be necessary for optimal expression and secretion of the encoded protein. The transgene may be designed to direct the expression of the encoded protein in a manner that facilitates its recovery from the organism or from a product produced by the organism, e.g. from the milk, blood, urine, eggs, hair or seeds of the organism. The transgene may consist of nucleic acid sequences derived from the genome of the same species or of a different species than the species of the target animal. The transgene may be integrated either at a locus of a genome where that particular nucleic acid sequence is not otherwise normally found or at the normal locus for the transgene.

The term "germ cell line transgenic organism" refers to a transgenic organism in which the genetic alteration or genetic information was introduced into a germ line cell, thereby conferring the ability of the transgenic organism to transfer the genetic information to offspring. If such offspring in fact possess some or all of that alteration or genetic information, then they too are transgenic organisms. The alteration or genetic information may be foreign to the species of organism to which the recipient belongs, foreign only to the particular individual recipient, or may be genetic information already possessed by the recipient. In the last case, the altered or introduced gene may be expressed differently than the native gene.

A transgenic organism may be a transgenic animal or a transgenic plant. Transgenic animals can be produced by a variety of different methods including transfection, electroporation, microinjection, gene targeting in embryonic stem cells and recombinant viral and retroviral infection (see, e.g., U.S. Pat. Nos. 4,736,866; 5,602,307; Mullins et al. (1993) Hypertension 22(4):630-633; Brenin et al. (1997) Surg. Oncol. 6(2):99-100; Tuan (ed.), Recombinant Gene Expression Protocols, Methods in Molecular Biology No. 62, Humana Press (1997)). The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. Nos. 5,489,743 and 5,602,307.

A number of recombinant or transgenic mice have been produced, including those which-express an activated oncogene sequence (U.S. Pat. No. 4,736,866); express simian SV40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720, 936); have a reduced capacity to mediate cellular adhesion (U.S. Pat. No. 5,602,307); possess a bovine growth hormone gene (Clutter et al. (1996) Genetics 143(4):1753-1760); or, are capable of generating a fully human antibody response (McCarthy (1997) The Lancet 349(9049):405).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al. (1997) *Mol. Reprod. Dev.* 46(4):515-526; Houdebine (1995) *Reprod. Nutr. Dev.* 35(6):609-617; Petters (1994) *Reprod. Fertil. Dev.* 6(5):643-645; Schnieke et al. (1997) *Science* 278(5346):2130-2133; and Amoah (1997) *J. Animal Science* 75(2):578-585).

To direct the secretion of the transgene-encoded protein of the invention into the milk of transgenic mammals, it may be put under the control of a promoter that is preferentially activated in mammary epithelial cells. Promoters that control the genes encoding milk proteins are preferred, for example the promoter for casein, beta lactoglobulin, whey acid protein, or lactalbumin (see, e.g., DiTullio (1992) *BioTechnology* 10:74-77; Clark et al. (1989) *BioTechnology* 7:487-492; Gorton et al. (1987) *BioTechnology* 5:1183-1187; and Soulier et al. (1992) *FEBS Letts.* 297:13). The transgenic mammals of choice would produce large volumes of milk and have long lactating periods, for example goats, cows, camels or sheep.

An albumin fusion protein of the invention can also be expressed in a transgenic plant, e.g. a plant in which the DNA transgene is inserted into the nuclear or plastidic genome. Plant transformation procedures used to introduce foreign nucleic acids into plant cells or protoplasts are known in the art. See, in general, *Methods in Enzymology* Vol. 153 ("Recombinant DNA Part D") 1987, Wu and Grossman Eds., Academic Press and European Patent Application EP 693554. Methods for generation of genetically engineered plants are further described in U.S. Pat. Nos. 5,283,184, 5,482,852, and European Patent Application EP 693 554, all of which are hereby incorporated by reference.

Pharmaceutical or Therapeutic Compositions

The albumin fusion proteins of the invention or formulations thereof may be administered by any conventional method including parenteral (e.g. subcutaneous or intramuscular) injection or intravenous infusion. The treatment may consist of a single dose or a plurality of doses over a period of time.

While it is possible for an albumin fusion protein of the invention to be administered alone, it is preferable to present it as a pharmaceutical formulation, together with one or more acceptable carriers. The carrier(s) must be "acceptable" in the sense of being compatible with the albumin fusion protein and not deleterious to the recipients thereof. Typically, the carriers will be water or saline which will be sterile and pyrogen free. Albumin fusion proteins of the invention are particularly well suited to formulation in aqueous carriers such as sterile pyrogen free water, saline or other isotonic solutions because of their extended shelf-life in solution. For instance, pharmaceutical compositions of the invention may be formulated well in advance in aqueous form, for instance, weeks or months or longer time periods before being dispensed.

For example, formulations containing the albumin fusion protein may be prepared taking into account the extended shelf-life of the albumin fusion protein in aqueous formulations. As discussed above, the shelf-life of many of these therapeutic proteins are markedly increased or prolonged after fusion to HA.

In instances where aerosol administration is appropriate, the albumin-insulin fusion proteins of the invention can be formulated as aerosols using standard procedures. The term "aerosol" includes any gas-borne suspended phase of an albumin-insulin fusion protein of the instant invention which is capable of being inhaled into the bronchioles or nasal passages. Specifically, aerosol includes a gas-borne suspension of droplets of an albumin-insulin fusion protein of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example. See Ganderton & Jones, Drug Delivery to the Respiratory Tract, Ellis Horwood (1987); Gonda (1990) *Critical Reviews in Therapeutic Drug Carrier Systems* 6:273-313; and Raeburn et al. (1992) *Pharmacol. Toxicol. Methods* 27:143-159.

Pharmaceutical compositions may include aerosols which contain albumin-insulin fusion proteins as described herein. Aerosols can be defined as very finely divided liquid droplets or dry particles dispersed in and surrounded by a gas. Both liquid and dry powder aerosol compositions are contemplated. The aerosols may be administered by a dry-powder inhalers ("PDI") or a metered-dose inhaler ("MDI") which optionally may be pressurized ("pMDI").

The albumin-insulin fusion protein may be present at any suitable concentration in an aerosol formulation. For liquid aerosol formulations (e.g., aqueous aerosol formulations), the albumin-insulin fusion protein may be present, for example, at a concentration of about 0.05 mg/mL up to about 600 mg/mL. For dry powder aerosol formulations, the albumin-insulin fusion protein may be present, for example, at a concentration of about 0.05 mg/g up to about 990 mg/g, depending on the desired dosage. Concentrated aerosols of albumin-insulin fusion protein, which may be defined as containing albumin-insulin fusion protein at a concentration of about 10 mg/mL up to about 600 mg/mL for aqueous aerosol formulations, and about 10 mg/g up to about 990 mg/g for dry powder aerosol formulations, are specifically contemplated. Such formulations may provide effective delivery to appropriate areas of the lung and/or nasal cavities in short administration times, i.e., less than about 15 seconds.

Aerosols intended for delivery to the nasal mucosa are inhaled through the nose. For optimal delivery to the nasal cavities, inhaled particle sizes of about 5 to about 100 microns are useful, with particle sizes of about 30 to about 60 microns being preferred. For nasal delivery, a larger inhaled particle size is desired to maximize impaction on the nasal mucosa and to minimize or prevent pulmonary deposition of the administered formulation. Inhaled particles may be defined as liquid droplets containing dissolved albumin-insulin fusion protein, liquid droplets containing suspended albumin-insulin fusion protein (in cases where the fusion protein is insoluble in the suspending medium), dry particles of albumin-insulin fusion protein, aggregates of albumin-insulin fusion protein, or dry particles of a diluent which contain embedded albumin-insulin fusion protein.

For delivery to the upper respiratory region, inhaled particle sizes of about 2 to about 10 microns are preferred, more preferred is about 2 to about 6 microns. For delivery to the deep lung (alveolar) region, inhaled particle sizes of less than about 2 microns are preferred. Aerosol formulations of the albumin-insulin fusion proteins described herein may be formed using air-jet or ultrasonic nebulizers. One example of such devices is the Circulaire® (Westmed Corp., Tucson, Ariz.).

In some embodiments, the albumin-insulin fusion protein may be formulated as a dry powder aerosol composition for pulmonary or nasal administration. Dry powders, which can be used in both DPIs and pMDIs, can be made by spray-drying solutions or dispersions of the albumin-insulin fusion protein (e.g., aqueous solutions or dispersions). Alternatively, dry powders containing the albumin-insulin fusion protein can be made by freeze-drying solutions or dispersions of the albumin-insulin fusion protein (e.g., aqueous solutions or dispersions). In some embodiments, combinations of spray-dried and freeze-dried albumin-insulin fusion protein drug powders can be used in DPIs and pMDIs. For dry powder aerosol compositions, the albumin-insulin fusion protein may be present, for example, at a concentration range of about 0.05 mg/g, 0.1 mg/g, 2 mg/g, 40 mg/g, or 100 mg/g to about 990 mg/g. concentrated aerosol formulations (e.g., dry powder aerosol formulations having an albumin-insulin fusion protein concentration of about 10 mg/g to about 990 mg/g) may deliver effective concentrations of the albumin-insulin fusion protein to the lung in a short period of time (e.g., less than 120 seconds, preferably less than 60 seconds, more preferably less than 30 seconds, and most preferably less than 15 seconds).

Dry powder aerosol compositions may include respirable aggregates of albumin-insulin fusion protein or respirable particles of a diluent which contains albumin-insulin fusion protein. Suitable diluents may include sugars or sugar alcohols (e.g., mannitol, lactose, and trehalose). Powders containing albumin-insulin fusion protein can be prepared from aqueous solutions or dispersions of albumin-insulin fusion protein by removing the liquid of the solution or dispersion via spray-drying or lyophilization (freeze drying). Dry powder aerosol compositions can be used in both DPIs and pMDIs. Typically, "dry" refers to a composition having less than about 5% liquid such as water.

Powders comprising albumin-insulin fusion protein can be made by spray-drying solutions or dispersions of albumin-insulin fusion protein. In some embodiments, a solution or dispersion of albumin-insulin fusion protein (and optionally surface modifier) optionally may contain a dissolved diluent such as lactose or mannitol which, when spray dried, forms respirable diluent particles, each of which contains embedded albumin-insulin fusion protein. In some embodiments, the diluent particles with embedded albumin-insulin fusion protein may have a particle size of about 1 to about 2 microns, suitable for deep lung delivery. In addition, the diluent particle size can be increased to target alternate delivery sites, such as the upper bronchial region or nasal mucosa by increasing the concentration of dissolved diluent in the aqueous dispersion prior to spray drying, or by increasing the droplet size generated by the spray dryer.

Spray-dried albumin-insulin fusion protein powders can be used in DPIs or pMDIs, either alone or combined with freeze-dried albumin-insulin fusion protein powder. In addition, spray-dried albumin-insulin fusion protein powders can be reconstituted and used in either jet or ultrasonic nebulizers to generate solutions or dispersions having respirable droplet sizes, where each droplet contains albumi-insulin fusion protein. Concentrated albumin-insulin fusion protein solutions or dispersions may also be prepared from spray-dried powders.

Solutions or dispersions of albumin-insulin fusion proteins can be freeze-dried to obtain powders suitable for nasal or pulmonary delivery. Such powders may contain aggregates of albumin-insulin fusion protein. Optionally, the aggregates may include a surface modifier and/or a diluent (e.g., a sugar or sugar alcohol). Such aggregates may have particle sizes within a respirable range, i.e., about 2 to about 5 microns. Larger aggregates can be obtained for targeting alternate delivery sites, such as the nasal mucosa.

Freeze-dried powders can be used in DPIs or pMDIs, either alone or combined with spray-dried powder. In addition, freeze-dried powders containing albumin-insulin fusion proteins can be reconstituted and used in either jet or ultrasonic nebulizers to generate solutions or dispersions having respirable droplet sizes, where each droplet contains albumin-insulin fusion proteins. Concentrated albumin-insulin fusion protein solutions or dispersions may also be prepared from freeze-dried powders.

Aggregates of freeze-dried albumin-insulin fusion protein can be blended with either dry powder intermediates or used alone in DPIs and pMDIs for either nasal or pulmonary delivery.

In some embodiments, the albumin-insulin fusion protein may be formulated as a composition for propellant-based systems. Such formulations may be prepared by wet milling the albumin-insulin fusion protein (and optionally a surface modifier) in liquid propellant, either at ambient pressure or under high pressure conditions. Alternatively, dry powders containing albumin-insulin fusion may be prepared by spray-drying or freeze-drying solutions or dispersions of albumin-insulin fusion protein (e.g., aqueous solutions or dispersions) and the resultant powders dispersed into suitable propellants for use in conventional pMDIs. Such pMDI formulations can be used for either nasal or pulmonary delivery. Concentrated aerosol formulations can also be employed in pMDIs. pMDIs of the present invention can utilize either chlorinated or non-chlorinated propellants.

The albumin-insulin fusion protein compositions for aerosol administration can be made by, for example, (1) nebulizing a solution or dispersion of albumin-insulin fusion protein (e.g. an aqueous solution or dispersion), obtained by either grinding or precipitation; (2) aerosolizing a dry powder of aggregates of albumin-insulin fusion protein (which optionally include a surface modifier and or a diluent); or (3)

aerosolizing a suspension of albumin-insulin fusion protein aggregates in a non-aqueous propellant. The aggregates of albumin-insulin fusion protein (which optionally may include a surface modifier and/or a diluent), can be made in a non-pressurized or a pressurized aqueous or non-aqueous system. Concentrated aerosol formulations may also be made via such methods.

In some embodiments, the aerosol composition may be used in methods to treat a patient in need thereof, comprising: (1) forming an aerosol of a solution or dispersion (either liquid or powder) of albumin-insulin fusion protein (and optionally a surface modifier and/or a diluent), and (2) administering the aerosol to the pulmonary or nasal cavities of the mammal. Concentrated aerosol formulations may also be used in such methods. The method may be used to treat a metabolic disease or disorder (e.g., diabetes).

The formulations of the invention are also typically non-immunogenic, in part, because of the use of the components of the albumin fusion protein being derived from the proper species. For instance, for human use, both the therapeutic protein and albumin portions of the albumin fusion protein will typically be human. In some cases, wherein either component is non human-derived, that component may be humanized by substitution of key amino acids so that specific epitopes appear to the human immune system to be human in nature rather than foreign.

The formulations may conveniently be presented in unit dosage form and may be prepared by any of the methods well known in the art of pharmacy. Such methods include the step of bringing into association the albumin fusion protein with the carrier that constitutes one or more accessory ingredients. In general the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation appropriate for the intended recipient; and aqueous and non-aqueous sterile suspensions which may include suspending agents and thickening agents. The formulations may be presented in unit-dose or multi-dose containers, for example sealed ampules, vials or syringes, and may be stored in a freeze-dried (lyophilised) condition requiring only the addition of the sterile liquid carrier, for example water for injections, immediately prior to use. Extemporaneous injection solutions and suspensions may be prepared from sterile powders. Dosage formulations may contain the therapeutic protein portion at a lower molar concentration or lower dosage compared to the non-fused standard formulation for the therapeutic protein given the extended serum half-life exhibited by many of the albumin fusion proteins of the invention.

Formulations or compositions of the invention may be packaged together with, or included in a kit with, instructions or a package insert referring to the extended shelf-life of the albumin fusion protein component. For instance, such instructions or package inserts may address recommended storage conditions, such as time, temperature and light, taking into account the extended or prolonged shelf-life of the albumin fusion proteins of the invention. Such instructions or package inserts may also address the particular advantages of the albumin fusion proteins of the inventions, such as the ease of storage for formulations that may require use in the field, outside of controlled hospital, clinic or office conditions. As described above, formulations of the invention may be in aqueous form and may be stored under less than ideal circumstances without significant loss of therapeutic activity.

Albumin fusion proteins of the invention can also be included in nutraceuticals. For instance, certain albumin fusion proteins of the invention may be administered in natural products, including milk or milk product obtained from a transgenic mammal which expresses albumin fusion protein. Such compositions can also include plant or plant products obtained from a transgenic plant which expresses the albumin fusion protein. The albumin fusion protein can also be provided in powder or tablet form, with or without other known additives, carriers, fillers and diluents. Nutraceuticals are described in Scott Hegenhart, Food Product Design, December 1993.

The invention also provides methods of treatment and/or prevention of diseases or disorders (such as, for example, any one or more of the diseases or disorders disclosed herein) by administration to a subject of an effective amount of an albumin fusion protein of the invention or a polynucleotide encoding an albumin fusion protein of the invention ("albumin fusion polynucleotide") in a pharmaceutically acceptable carrier.

The albumin fusion protein and/or polynucleotide will be formulated and dosed in a fashion consistent with good medical practice, taking into account the clinical condition of the individual patient (especially the side effects of treatment with the albumin fusion protein and/or polynucleotide alone), the site of delivery, the method of administration, the scheduling of administration, and other factors known to practitioners. The "effective amount" for purposes herein is thus determined by such considerations.

As a general proposition, the total pharmaceutically effective amount of the albumin fusion protein administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the albumin fusion protein is typically administered at a dose rate of about 1 ug/kg/hour to about 50 ug/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Albumin fusion proteins and/or polynucleotides can be are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Albumin fusion proteins and/or polynucleotides of the invention are also suitably administered by sustained-release systems. Examples of sustained-release albumin fusion proteins and/or polynucleotides are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion. Additional examples of sustained-release albumin fusion proteins and/or polynucleotides include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547-556 (1983)), poly(2-hydroxyethyl methacrylate) (Langer et al., J. Biomed. Mater. Res. 15:167-277 (1981), and Langer, Chem. Tech. 12:98-105 (1982)), ethylene vinyl acetate (Langer et al., Id.) or poly-D-(–)-3-hydroxybutyric acid (EP 133,988).

Sustained-release albumin fusion proteins and/or polynucleotides also may include liposomally entrapped albumin fusion proteins and/or polynucleotides of the invention (see generally, Langer, Science 249:1527-1533 (1990); Treat et al., in Liposomes in the Therapy of Infectious Disease and Cancer, Lopez-Berestein and Fidler (eds.), Liss, New York, pp. 317-327 and 353-365 (1989)). Liposomes containing the albumin fusion protein and/or polynucleotide are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapeutic.

In yet an additional embodiment, the albumin fusion proteins and/or polynucleotides of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). Other controlled release systems are discussed in the review by Langer (Science 249:1527-1533 (1990)).

For parenteral administration, in one embodiment, the albumin fusion protein and/or polynucleotide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the therapeutic.

Generally, the formulations are prepared by contacting the albumin fusion protein and/or polynucleotide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The albumin fusion protein is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Albumin fusion proteins and/or polynucleotides generally are placed into a container having a sterile access port, for example, an intravenous solution bag or vial having a stopper pierceable by a hypodermic injection needle.

Albumin fusion proteins and/or polynucleotides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous albumin fusion protein and/or polynucleotide solution, and the resulting mixture is lyophilized. The infusion solution is prepared by reconstituting the lyophilized albumin fusion protein and/or polynucleotide using bacteriostatic Water-for-Injection.

In a specific and preferred embodiment, the Albumin fusion protein formulations comprises 0.01 M sodium phosphate, 0.15 mM sodium chloride, 0.16 micromole sodium octanoate/milligram of fusion protein, 15 micrograms/milliliter polysorbate 80, pH 7.2. In another specific and preferred embodiment, the Albumin fusion protein formulations consists 0.01 M sodium phosphate, 0.15 mM sodium chloride, 0.16 micromole sodium octanoate/milligram of fusion protein, 15 micrograms/milliliter polysorbate 80, pH 7.2. The pH and buffer are chosen to match physiological conditions and the salt is added as a tonicifier. Sodium octanoate has-been chosen due to its reported ability to increase the thermal stability of the protein in solution. Finally, polysorbate has been added as a generic surfactant, which lowers the surface tension of the solution and lowers non-specific adsorption of the albumin fusion protein to the container closure system.

The invention also provides a pharmaceutical pack or kit comprising one or more containers filled with one or more of the ingredients of the albumin fusion proteins and/or polynucleotides of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the albumin fusion proteins and/or polynucleotides may be employed in conjunction with other therapeutic compounds.

The albumin fusion proteins and/or polynucleotides of the invention may be administered alone or in combination with adjuvants. Adjuvants that may be administered with the albumin fusion proteins and/or polynucleotides of the invention include, but are not limited to, alum, alum plus deoxycholate (ImmunoAg), MTP-PE (Biocine Corp.), QS21 (Genentech, Inc.), BCG (e.g., THERACYS®), MPL and nonviable preparations of *Corynebacterium parvum*. In a specific embodiment, albumin fusion proteins and/or polynucleotides of the invention are administered in combination with alum. In another specific embodiment, albumin fusion proteins and/or polynucleotides of the invention are administered in combination with QS-21. Further adjuvants that may be administered with the albumin fusion proteins and/or polynucleotides of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the albumin fusion proteins and/or polynucleotides of the invention include, but are not limited to, vaccines directed toward protection against MMR (measles, mumps, rubella), polio, varicella, tetanus/diptheria, hepatitis A, hepatitis B, *Haemophilus influenzae* B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The albumin fusion proteins and/or polynucleotides of the invention may be administered alone or in combination with other therapeutic agents.

In an additional embodiment, albumin fusion proteins and/or polynucleotides of the invention are administered alone or in combination with one or more intravenous immune globulin preparations. Intravenous immune globulin preparations that may be administered with the albumin fusion proteins and/or polynucleotides of the invention include, but not limited to, GAMMAR™, IVEEGAM™, SANDOGLOBULIN™, GAMMAGARD S/D™, ATGAM™ (antithymocyte glubulin), and GAMIMUNE™. In a specific embodiment, albumin fusion proteins and/or polynucleotides of the invention are administered in combination with intravenous immune globulin preparations in transplantation therapy (e.g., bone marrow transplant).

Albumin fusion proteins of the present invention can be administered to any animal, preferably to mammals and birds. Preferred mammals include humans, dogs, cats, mice, rats, rabbits sheep, cattle, horses and pigs, with humans being particularly preferred.

Biological Activities

Albumin fusion proteins and/or polynucleotides encoding albumin fusion proteins of the present invention, can be used in assays to test for one or more biological activities. If an albumin fusion protein and/or polynucleotide exhibits an activity in a particular assay, it is likely that the therapeutic protein corresponding to the fusion protein may be involved in the diseases associated with the biological activity. Thus, the fusion protein could be used to treat the associated disease.

In preferred embodiments, the present invention encompasses a method of treating a disease or disorder associated with insulin deficiency or elevated blood glucose levels comprising administering to a patient in which such treatment, prevention or amelioration is desired an albumin fusion protein of the invention that comprises a therapeutic protein portion corresponding to an albumin-insulin fusion protein in an amount effective to treat, prevent or ameliorate the disease or disorder.

In a further preferred embodiment, the present invention encompasses a method of treating a disease or disorder associated with insulin deficiency or elevated glucose levels comprising administering to a patient in which such treatment, prevention or amelioration is desired an albumin fusion protein of the invention that comprises a therapeutic protein portion corresponding to the therapeutic protein for which the indications in the Examples are related in an amount effective to treat, prevent or ameliorate the disease or disorder.

In preferred embodiments, fusion proteins of the present invention may be used in the diagnosis, prognosis, prevention and/or treatment of diseases and/or disorders relating to insulin deficiency or elevated blood glucose levels.

In certain embodiments, an albumin fusion protein of the present invention may be used to diagnose and/or prognose diseases and/or disorders associated with the tissue(s) in which the gene corresponding to the therapeutic protein portion of the fusion protein of the invention is expressed.

Thus, fusion proteins of the invention and polynucleotides encoding albumin fusion proteins of the invention are useful in the diagnosis, detection and/or treatment of diseases and/or disorders associated with activities that include, but are not limited to, insulin deficiency or elevated blood glucose levels (e.g., insulin-dependent diabetes mellitus).

In addition, fusion proteins of the invention and/or polynucleotides encoding albumin fusion proteins of the invention, could be used treat or prevent the onset of diabetes mellitus. In patients with newly diagnosed Types I and II diabetes, where some islet cell function remains, fusion proteins of the invention and/or polynucleotides encoding albumin fusion proteins of the invention, could be used to maintain the islet function so as to alleviate, delay or prevent permanent manifestation of the disease. Also, fusion proteins of the invention and/or polynucleotides encoding albumin fusion proteins of the invention, could be used as an auxiliary in islet cell transplantation to improve or promote islet cell function.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

Without further description, it is believed that one of ordinary skill in the art can, using the preceding description and the following illustrative examples, make and utilize the alterations detected in the present invention and practice the claimed methods. All publications referred to herein, including but not limited to U.S. patents, are specifically incorporated by reference. The following working examples therefore, specifically point out preferred embodiments of the present invention, and are not to be construed as limiting in any way the remainder of the disclosure.

EXAMPLES

Example 1

Generation of pScNHSA and pScCHSA

The vectors pScNHSA (ATCC Deposit No. PTA-3279) and pScCHSA (ATCC Deposit No. PTA-3276) are derivatives of pPPC0005 (ATCC Deposit No. PTA-3278) and are used as cloning vectors into which polynucleotides encoding a therapeutic protein or fragment or variant thereof is inserted adjacent to and in translation flame with polynucleotides encoding human serum albumin "HSA." pScCHSA may be used for generating therapeutic protein-HSA fusions, while pScNHSA may be used to generate HSA-therapeutic protein fusions.

Generation of pScCHSA: Albumin Fusion with the Albumin Moiety C-Terminal to the Therapeutic Portion.

A vector to facilitate cloning DNA encoding a therapeutic protein N-terminal to DNA encoding the mature albumin protein was made by altering the nucleic acid sequence that encodes the chimeric HSA signal peptide in pPPC0005 to include the Xho I and Cla I restriction sites.

First, the Xho I and Cla I sites inherent to pPPC0005 (located 3' of the ADH1 terminator sequence) were eliminated by digesting pPPC0005 with Xho I and Cla I, filling in the sticky ends with T4 DNA polymerase, and religating the blunt ends to create pPPC0006.

Second, the Xho I and Cla I restriction sites were engineered into the nucleic acid sequence that encodes the signal peptide of HSA (a chimera of the HSA leader and a kex2 site from mating factor alpha, "MAF") in pPPC0006 using two rounds of PCR. In the first round of PCR, amplification was performed. The primer comprised a nucleic acid sequence that encodes part of the signal peptide sequence of HSA, a kex2 site from the mating factor alpha leader sequence, and part of the amino-terminus of the mature form of HSA. Four point mutations were introduced in the sequence, creating the Xho I and Cla I sites found at the junction of the chimeric signal peptide and the mature form of HSA as provided in the sequence shown below. In pPPC0005 the nucleotides at these four positions from 5' to 3' are T, G, T, and G. 5'-GCCTCGAGAAAAGAGATGCACACAAGAGTGAG-GTTGCTCATCGATTTAAA-GAT TTGGG-3' (SEQ ID NO:51) and 5'-AATCGATGAGCAACCTCACTCTTGT-GTGCATCTCTTT-TCTCGAGGCTCCTGGAA TAAGC-3' (SEQ ID NO:52). A second round of PCR was then performed with an upstream flanking primer, 5'-TA-CAAACTTAAGAGTCCAATT-AGC-3' (SEQ ID NO:53) a downstream flanking primer 5'-CACTTCTCTAGAGTG-GTTTCATATGTCTT-3' (SEQ ID NO:54). The resulting PCR product was then purified and digested with Afl II and Xba I and ligated into the same sites in pPPC0006 creating pScCHSA. The resulting plasmid has Xho I and Cla I sites engineered into the signal sequence. The presence of the Xho I site creates a single amino acid change in the end of the signal sequence from LDKR (SEQ ID NO:55) to LEKR (SEQ ID NO:56). The D to E change will not be present in the final albumin fusion protein expression plasmid when a nucleic acid sequence comprising a polynucleotide encoding the therapeutic portion of the albumin fusion protein with a 5' Sal I site (which is compatible with the Xho I site) and a 3' Cla I site is ligated into the Xho I and Cla I sites of pScCHSA. Ligation of Sal I to Xho I restores the original amino acid sequence of the signal peptide sequence. DNA encoding the therapeutic portion of the albumin fusion protein may be inserted after the Kex2 site (Kex2 cleaves after the dibasic amino acid sequence KR at the end of the signal peptide) and prior to the Cla I site.

Generation of pScNHSA: Albumin Fusion with the Albumin Moiety N-Terminal to the Therapeutic Portion.

A vector to facilitate cloning DNA encoding a therapeutic protein portion C-terminal to DNA encoding the mature albumin protein, was made by adding three, eight-base-pair restriction sites to pScCHSA. The Asc I, Fse I, and Pme I restriction sites were added in between the Bsu36 I and Hind III sites at the end of the nucleic acid sequence encoding the mature HSA protein. This was accomplished through the use of two complementary synthetic primers containing the Asc I, Fse I, and Pme I restriction sites. 5'-AAGCTGCCTTAG-GCTTATAATAAGGCGCGCCGGCCGGCCGTT-TAAACTAAGCT TAATTCT-3' (SEQ ID NO:57) and 5'-AGAATTAAGCTTAGTTTAAACGGCCGGCCG-GCGCGCCTTATTATAAGCCTAAG GCAGCTT-3' (SEQ ID NO:58). These primers were annealed and digested with Bsu36 I and Hind III and ligated into the same sites in pScCHSA creating pScNHSA.

Example 2

General Construct Generation for Yeast Transformation

The vectors pScNHSA and pScCHSA may be used as cloning vectors into which polynucleotides encoding a therapeutic protein or fragment or variant thereof is inserted adjacent to polynucleotides encoding mature human serum albumin "HSA." pScCHSA is used for generating therapeutic protein-HSA fusions, while pScNHSA may be used to generate HSA-therapeutic protein fusions.

Generation of Albumin Fusion Constructs Comprising HSA-Therapeutic Protein Fusion Products.

DNA encoding an insulin protein or analog may be PCR amplified using the primers which facilitate the generation of a fusion construct (e.g., by adding restriction sites, encoding seamless fusions, encoding linker sequences, etc.). For example, one skilled in the art could design a 5' primer that adds polynucleotides encoding the last four amino acids of the mature form of HSA (and containing the Bsu36I site) onto the 5' end of DNA encoding a therapeutic protein; and a 3' primer that adds a STOP codon and appropriate cloning sites onto the 3' end of the therapeutic protein coding sequence. For instance, the forward primer used to amplify DNA encoding a therapeutic protein might have the sequence, 5'-aagctGCCTTAGGCTTA(N)15-3' (SEQ ID NO:59), including a Bsu36I site, where the upper case nucleotides encode the last four amino acids of the mature HSA protein (ALGL; SEQ ID NO:60) and (N)15 is identical to the first 15 nucleotides encoding the therapetic protein of interest. Similarly, the reverse primer used to amplify DNA encoding a therapeutic protein might have the sequence, 5'-GCGCGCGTTTAAACGGCCGGCCGGC-GCGCC(N) 15-3' (SEQ ID NO:61), including a Pme I site, an Fse I site, an Asc I site, the reverse complement of two tandem stop codons, and (N)15 is identical to the reverse complement of the last 15 nucleotides encoding the therapeutic protein of interest. Once the PCR product is amplified it may be cut with Bsu36I and one of (Asc I, Fse I, or Pme I) and ligated into pScNHSA.

The presence of the Xho I site in the HSA chimeric leader sequence creates a single amino acid change in the end of the chimeric signal sequence, i.e. the HSA-kex2 signal sequence, from LDKR to LEKR.

Generation of Albumin Fusion Constructs Comprising Gene-HSA Fusion Products.

Similar to the method described above, DNA encoding a therapeutic protein may be PCR amplified using the following primers: A 5' primer that adds polynucleotides containing a SalI site and encoding the last three amino acids of the HSA leader sequence, DKR, onto the 5' end of DNA encoding a therapeutic protein; and a 3' primer that adds polynucleotides encoding the first few amino acids of the mature HSA containing a Cla I site onto the 3' end of DNA encoding a therapeutic protein. For instance, the forward primer used to amplify the DNA encoding a therapeutic protein might have the sequence, 5'-AGGAGCGTCGA-CAAAAGA(N)15-3' (SEQ ID NO:62), including a Sal I site, where the upper case nucleotides encode the last three amino acids of the HSA leader sequence (DKR), and (N)15 is identical to the first 15 nucleotides encoding the therapetic protein of interest. Similarly, the reverse primer used to amplify the DNA encoding a therapeutic protein might have the sequence, 5'-CTTTAAATCGATGAGCAACCT-CACTCTTGTGTGCATC(N)15-3' (SEQ ID NO:63), including a Cla I site, the reverse complement of the DNA encoding the first 9 amino acids of the mature form of HSA (DAHKSEVAH) (SEQ ID NO:64), and (N)15 is identical to the reverse complement of the last 15 nucleotides encoding the therapeutic protein of interest. Once the PCR product is amplified it may be cut with Sal I and Cla I and ligated into pScCHSA digested with Xho I and Cla I. A different signal or leader sequence may be desired, for example, invertase "INV" (Swiss-Prot Accession P00724), mating factor alpha "MAF"(Genbank Accession AAA18405), MPIF (Geneseq AAF82936), Fibulin B (Swiss-Prot Accession P23142), Clusterin (Swiss-Prot Accession P10909), Insulin-Like Growth Factor-Binding Protein 4 (Swiss-Prot Accession P22692), and permutations of the HSA leader sequence can be subcloned into the appropriate vector by means of standard methods known in the art.

Generation of Albumin Fusion Construct Compatible for Expression in Yeast S. cerevisiae.

The Not I fragment containing the DNA encoding either an N-terminal or C-terminal albumin fusion protein generated from pScNHSA or pScCHSA may then be cloned into the Not I site of pSAC35 which has a LEU2 selectable marker. The resulting vector is then used in transformation of a yeast S. cerevisiae expression system.

Example 3

General Expression in Yeast S. cerevisiae.

Figure 3:
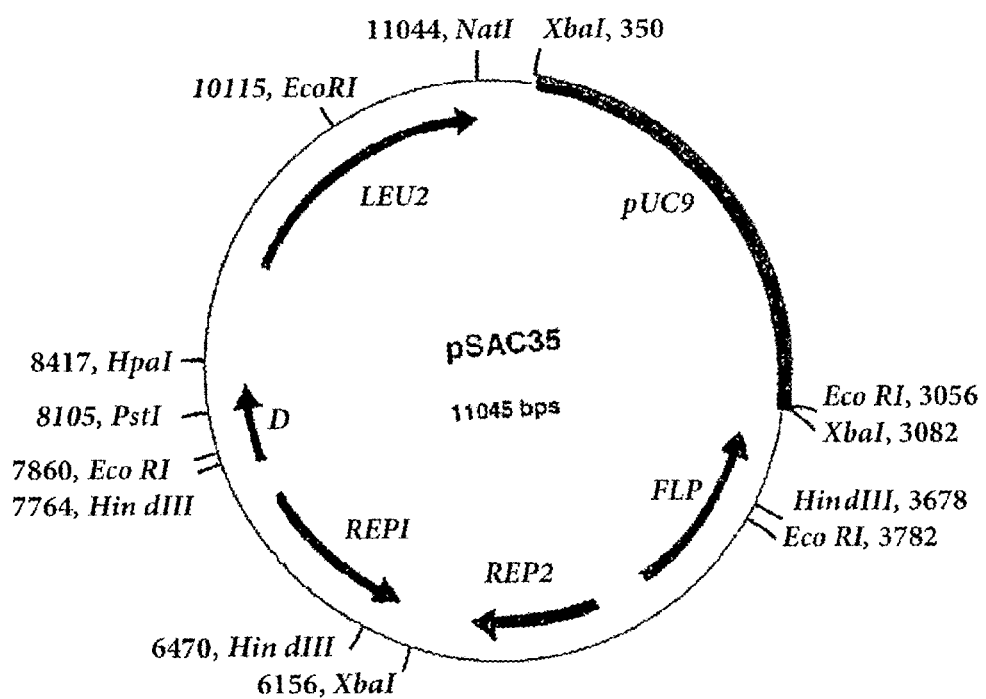
FIG. 3 shows the restriction map of the pSAC35 yeast *S. cerevisiae* expression vector (Sleep et al., *BioTechnology*, 8:42 (1990)).

An expression vector compatible with yeast expression can be transformed into yeast S. cerevisiae by lithium acetate transformation, electroporation, or other methods known in the art and or as described in part in Sambrook, Fritsch, and Maniatis. 1989. "Molecular Cloning: A Laboratory Manual, 2nd edition," volumes 1-3, and in Ausubel et al. 2000. Massachusetts General Hospital and Harvard Medical School "Current Protocols in Molecular Biology," volumes 1-4. The expression vectors are introduced into S. cerevisiae strains DXY1, D88, or BXP10 by transformation, individual transformants can be grown, for example, for 3 days at 30° C. in 10 mL YEPD (1% w/v yeast extract, 2% w/v, peptone, 2% w/v, dextrose), and cells can be collected at stationary phase after 60 hours of growth. Supernatants are collected by clarifying cells at 3000 g for 10 minutes.

pSAC35 (Sleep et al., 1990, Biotechnology 8:42 and see FIG. 3) comprises, in addition to the LEU2 selectable marker, the entire yeast 2 µm plasmid to provide replication functions, the PRB1 promoter, and the ADH1 termination signal.

Example 4

General Purification of an Albumin Fusion Protein Expressed from an Albumin Fusion in Yeast S. cerevisiae.

In preferred embodiments, albumin fusion proteins of the invention comprise the mature form of HSA fused to either the N- or C-terminus of the mature form of a therapeutic protein or portions thereof (e.g., the mature form of insulin or an insulin analog.). In one embodiment of the invention, albumin fusion proteins of the invention further comprise a signal sequence which directs the nascent fusion polypeptide in the secretory pathways of the host used for expression. In a preferred embodiment, the signal peptide encoded by the signal sequence is removed, and the mature albumin fusion protein is secreted directly into the culture medium. Albumin fusion proteins of the invention preferably comprise heterologous signal sequences (e.g., the non-native signal sequence of a particular therapeutic protein) including, but not limited to, MAF, INV, Ig, Fibulin B, Clusterin, Insulin-Like Growth Factor Binding Protein 4, variant HSA leader sequences including, but not limited to, a chimeric HSA/MAF leader sequence, or other heterologous signal sequences known in the art. In preferred embodiments, the fusion proteins of the invention further comprise an N-terminal methionine residue. Polynucleotides encoding these polypeptides, including fragments and/or variants, are also encompassed by the invention.

Albumin fusion proteins expressed in yeast as described above can be purified on a small-scale over a Dyax peptide affinity column as follows. Supernatants from yeast expressing an albumin fusion protein is diafiltrated against 3 mM phosphate buffer pH 6.2, 20 mM NaCl and 0.01% Tween 20 to reduce the volume and to remove the pigments. The solution is then filtered through a 0.22 µm device. The filtrate is loaded onto a Dyax peptide affinity column. The column is eluted with 100 mM Tris/HCl, pH 8.2 buffer. The peak fractions containing protein are collected and analyzed on SDS-PAGE after concentrating 5-fold.

For large scale purification, the following method can be utilized. The supernatant in excess of 2 L is diafiltered and concentrated to 500 mL in 20 mM Tris/HCl pH 8.0. The concentrated protein solution is loaded onto a pre-equilibrated 50 mL DEAE-Sepharose Fast Flow column, the column is washed, and the protein is eluted with a linear gradient of NaCl from 0 to 0.4 M NaCl in 20 mM Tris/HCl, pH 8.0. Those fractions containing the protein are pooled, adjusted to pH 6.8 with 0.5 M sodium phosphate ($NaH_2PO_4$). A final concentration of 0.9 M $(NH_4)_2SO_4$ is added to the protein solution and the whole solution is loaded onto a pre-equilibrated 50 mL Butyl650S column. The protein is eluted with a linear gradient of ammonium sulfate (0.9 to 0 M $(NH_4)_2SO_4$). Those fractions with the albumin fusion are again pooled, diafiltered against 10 mM $Na_2HPO_4$/citric acid buffer pH 5.75, and loaded onto a 50 mL pre-equilibrated SP-Sepharose Fast Flow column. The protein is eluted with a NaCl linear gradient from 0 to 0.5 M. The fractions containing the protein of interest are combined, the buffer is changed to 10 mM $Na_2HPO_4$/citric acid pH 6.25 with an Amicon concentrator, the conductivity is <2.5 mS/cm. This protein solution is loaded onto a 15 mL pre-equilibrated Q-Sepharose high performance column, the column is washed, and the protein is eluted with a NaCl linear gradient from 0 to 0.15 M NaCl. The purified protein can then be formulated into a specific buffer composition by buffer exchange.

Example 5

General Construct Generation for Mammalian Cell Transfection

Generation of Albumin Fusion Construct Compatible for Expression in Mammalian Cell-Lines Albumin fusion constructs can be generated in expression vectors for use in mammalian cell culture systems. DNA encoding a therapeutic protein can be cloned N-terminus or C-terminus to HSA in a mammalian expression vector by standard methods known in the art (e.g., PCR amplification, restriction digestion, and ligation). Once the expression vector has been constructed, transfection into a mammalian expression system can proceed. Suitable vectors are known in the art including, but not limited to, for example, the pC4 vector, and/or vectors available from Lonza Biologics, Inc. (Portsmouth, N.H.).

The DNA encoding human serum albumin has been cloned into the pC4 vector which is suitable for mammalian culture systems, creating plasmid pC4:HSA (ATCC Deposit #PTA-3277). This vector has a DiHydroFolate Reductase, "DHFR," gene that will allow for selection in the presence of methotrexate.

The pC4:HSA vector is suitable for expression of albumin fusion proteins in CHO cells. For expression, in other mammalian cell culture systems, it may be desirable to subclone a fragment comprising, or alternatively consisting of, DNA which encodes for an albumin fusion protein into an alternative expression vector. For example, a fragment comprising, or alternatively consisting, of DNA which encodes for a mature albumin fusion protein may be subcloned into another expression vector including, but not limited to, any of the mammalian expression vectors described herein.

In a preferred embodiment, DNA encoding an albumin fusion construct is subcloned into vectors provided by Lonza Biologics, Inc. (Portsmouth, N.H.) by procedures known in the art for expression in NSO cells.

Generation of Albumin Fusion Constructs Comprising HSA-Therapeutic Protein Fusion Products.

Using pC4:HSA (ATCC Deposit #PTA-3277), albumin fusion constructs can be generated in which the therapeutic protein portion is C terminal to the mature albumin sequence. For example, one can clone DNA encoding a therapeutic protein of fragment or variant thereof between the Bsu 36I and Asc I restriction sites of the vector. When cloning into the Bsu 36I and Asc I, the same primer design used to clone into the yeast vector system may be employed (see Example 2).

Generation of Albumin Fusion Constructs Comprising Gene-HSA Fusion Products.

Using pC4:HSA (ATCC Deposit #PTA-3277), albumin fusion constructs can be generated in which a therapeutic protein portion is cloned N terminal to the mature albumin sequence. For example, one can clone DNA encoding a therapeutic protein that has its own signal sequence between the Bam HI (or Hind III) and Cla I sites of pC4:HSA. When cloning into either the Bam HI or Hind III site, it is preferrable to include a Kozak sequence (CCGCCACCATG) (SEQ ID NO:65) prior to the translational start codon of the DNA encoding the therapeutic protein. If a therapeutic protein does not have a signal sequence, DNA encoding that therapeutic protein may be cloned in between the Xho I and Cla I sites of pC4:HSA. When using the Xho I site, the following 5' and 3' exemplary PCR primers may be used: 14 5'-CCGCCGCTCGAGGGGTGT-GTTTCGTCGA (N)18-3' (SEQ ID NO:66) 5'-AGTC-CCATCGATGAGCAACCTCACTCTT GTGTGCATC(N) 18-3' (SEQ ID NO:67).

The 5' primer includes a Xho I site; and the Xho I site and the DNA following the Xho I site code for the last seven amino acids of the leader sequence of natural human serum albumin. "(N)18" designates DNA identical to the first 18 nucleotides encoding the therapeutic protein of interest. The 3' primer includes a Cla I site; and the Cla I site and the DNA following it are the reverse complement of the DNA encoding the first 10 amino acids of the mature HSA protein. "(N)18" designates the reverse complement of DNA encoding the last 18 nucleotides encoding the therapeutic protein of interest. Using these two primers, one may PCR amplify the therapeutic protein of interest, purify the PCR product, digest it with Xho I and Cla I restriction enzymes and clone it into the Xho I and Cla I sites in the pC4:HSA vector.

If an alternative leader sequence is desired, the native albumin leader sequence can be replaced with the chimeric albumin leader, i.e., the HSA-kex2 signal peptide, or an alternative leader by standard methods known in the art. (For example, one skilled in the art could routinely PCR amplify an alternate leader and subclone the PCR product into an albumin fusion construct in place of the albumin leader while maintaining the reading frame).

Example 6

General Expression in Mammalian Cell-Lines

An albumin fusion construct generated in an expression vector compatible with expression in mammalian cell-lines can be transfected into appropriate cell-lines by calcium phosphate precipitation, lipofectamine, electroporation, or other transfection methods known in the art and/or as described in Sambrook, Fritsch, and Maniatis. 1989. "Molecular Cloning: A Laboratory Manual, 2nd edition" and in Ausubel et al. 2000. Massachusetts General Hospital and Harvard Medical School "Current Protocols in Molecular Biology," volumes 1-4. The transfected cells are then selected for by the presence of a selecting agent determined by the selectable marker in the expression vector.

The pC4 expression vector (ATCC Accession No. 209646) is a derivative of the plasmid pSV2-DHFR (ATCC Accession No. 37146). pC4 contains the strong promoter Long Terminal Repeats "LTR" of the Rous Sarcoma Virus (Cullen et al., March 1985, Molecular and Cellular Biology, 438-447) and a fragment of the CytoMegaloVirus "CMV"-enhancer (Boshart et al., 1985, Cell 41: 521-530). The vector also contains the 3' intron, the polyadenylation and termination signal of the rat preproinsulin gene, and the mouse DHFR gene under control of the SV40 early promoter. Chinese hamster ovary "CHO" cells or other cell-lines lacking an active DHFR gene are used for transfection. Transfection of an albumin fusion construct in pC4 into CHO cells by methods known in the art will allow for the expression of the albumin fusion protein in CHO cells, followed by leader sequence cleavage, and secretion into the supernatant. The albumin fusion protein is then further purified from the supernatant.

The pEE12.1 expression vector is provided by Lonza Biologics, Inc. (Portsmouth, N.H.) and is a derivative of pEE6 (Stephens and Cockett, 1989, Nucl. Acids Res. 17: 7110). This vector comprises a promoter, enhancer and complete 5'-untranslated region of the Major Immediate Early gene of the human CytoMegaloVirus, "hCMV-MIE" (International Publication #WO 89/01036), upstream of a sequence of interest, and a Glutamine Synthetase gene (Murphy et al., 1991, Biochem J. 227: 277-279; Bebbington et al., 1992, Bio/Technology 10:169-175; U.S. Pat. No. 5,122,464) for purposes of selection of transfected cells in selective methionine sulphoximine containing medium. Transfection of albumin fusion constructs made in pEE12.1 into NS0 cells (International Publication #WO 86/05807) by methods known in the art will allow for the expression of the albumin fusion protein in NS0 cells, followed by leader sequence cleavage, and secretion into the supernatant. The albumin fusion protein is then further purified from the supernatant using techniques described herein or otherwise known in the art.

Expression of an albumin fusion protein may be analyzed, for example, by SDS-PAGE and Western blot, reversed phase HPLC analysis, or other methods known in the art.

Stable CHO and NS0 cell-lines transfected with albumin fusion constructs are generated by methods known in the art (e.g., lipofectamine transfection) and selected, for example, with 100 nM methotrexate for vectors having the DiHydro-Folate Reductase 'DHFR' gene as a selectable marker or through growth in the absence of glutamine. Expression levels can be examined for example, by immunoblotting, primarily, with an anti-HSA serum as the primary antibody, or, secondarily, with serum containing antibodies directed to the therapeutic protein portion of a given albumin fusion protein as the primary antibody.

Expression levels are examined by immunoblot detection with anti-HSA serum as the primary antibody. The specific productivity rates are determined via ELISA in which the capture antibody can be a monoclonal antibody towards the therapeutic protein portion of the albumin fusion and the detecting antibody can be the monoclonal anti-HSA-biotinylated antibody (or vice versa), followed by horseradish peroxidase/streptavidin binding and analysis according to the manufacturer's protocol.

Example 7

General Purification of an Albumin Fusion Protein Expressed from an Albumin Fusion Construct in Mammalian Cell-Lines In preferred embodiments, albumin fusion proteins of the invention comprise the mature form of HSA fused to either the N- or C-terminus of the mature form of a therapeutic protein or portions thereof (e.g., the mature form of insulin or an insulin analog). In one embodiment of the invention, albumin fusion proteins of the invention further comprise a signal sequence which directs the nascent fusion polypeptide in the secretory pathways of the host used for expression. In a preferred embodiment, the signal peptide encoded by the signal sequence is removed, and the mature albumin fusion protein is secreted directly into the culture medium. Albumin fusion proteins of the invention preferably comprise heterologous signal sequences (e.g., the non-native signal sequence of a particular therapeutic protein) including, but not limited to, MAF, INV, Ig, Fibulin B, Clusterin, Insulin-Like Growth Factor Binding Protein 4, variant HSA leader sequences including, but not limited to, a chimeric HSA/MAF leader sequence, or other heterologous signal sequences known in the art. In preferred embodiments, the fusion proteins of the invention further comprise an N-terminal methionine residue. Polynucleotides encoding these polypeptides, including fragments and/or variants, are also encompassed by the invention.

Albumin fusion proteins from mammalian cell-line supernatants are purified according to different protocols depending on the expression system used.

Purification from CHO and 293T Cell-lines.

Purification of an albumin fusion protein from CHO cell supernatant or from transiently transfected 293T cell supernatant may involve initial capture with an anionic HQ resin using a sodium phosphate buffer and a phosphate gradient elution, followed by affinity chromatography on a Blue Sepharose FF column using a salt gradient elution. Blue Sepharose FF removes the main BSA/fetuin contaminants. Further purification over the Poros PI 50 resin with a phosphate gradient may remove and lower endotoxin contamination as well as concentrate the albumin fusion protein.

Purification from NS0 Cell-line.

Purification of an albumin-fusion protein from NS0 cell supernatant may involve Q-Sepharose anion exchange chromatography, followed by SP-sepharose purification with a step elution, followed by Phenyl-650M purification with a step elution, and, ultimately, diafiltration.

The purified protein may then be formulated by buffer exchange.

Example 8

Construct ID 2250, HSA-Insulin (GYG), Generation

Construct ID 2250, pSAC35.HSA.INSULIN (GYG).F1-N62, encodes for an HSA-INSULIN (GYG) fusion protein which comprises full length HSA, including the native HSA leader sequence, fused to the amino-terminus of the synthetic single-chain long-acting insulin analog (INSULIN (GY32G)) with a Tyr at position 32, cloned into the yeast *S. cerevisiae* expression vector pSAC35.

Cloning of INSULIN (GYG) cDNA for Construct 2250.

The DNA encoding the synthetic single-chain form of INSULIN (GYG) was PCR generated using four overlapping primers. The sequence corresponding to the C-peptide in the middle region of the proinsulin cDNA was replaced by the C-domain of Insulin Growth Factor 1, "IGF-1" (GY32GSSSRRAPQT) (SEQ ID NO: 2), to avoid the need for proinsulin processing and to ensure proper folding of the single-chain protein. The sequence was codon optimized for expression in yeast *S. cerevisiae*. The PCR fragment was digested and subcloned into Bsu 36I/Asc I digested pSc-NHSA. A Not I fragment was then subcloned into the pSAC35 plasmid. Construct ID #2250 encodes for full length HSA, including the native HSA leader sequence, fused to the amino-terminus of the synthetic single-chain form of INSULIN (GYG).

The 5' and 3' primers of the four overlapping oligonucleotides suitable for PCR amplification of the polynucleotide encoding the synthetic single-chain form of INSULIN (GYG), INSULIN (GYG)-1 and INSULIN (GYG)-2, were synthesized: 32 INSULIN (GYG)-1: 5'-GTCAAGCTGC-CTTAGGCTTATTCGTTAACCAA CACTTGTGTGGT-TCTCACTTGGTTGAAGCTTTGTAC TTGGTTTGTG-GTGAA-3' (SEQ ID NO:68) INSULIN (GYG)-2: 5'-ATCGCATATGGCGCGCCCTATTAGTTACAGTA GTTTTCCAATTGGTACAAAGAACAAATAGAAGTAC AA-3' (SEQ ID NO:69).

INSULIN (GYG)-1 incorporates a Bsu 36I cloning site and encodes the first 21 amino acids of the ORF of the synthetic single-chain form of INSULIN (GYG). INSULIN (GYG)-2 incorporates an Asc I site. INSULIN (GYG)-2 also includes the reverse complement of the last 49 nucleotides encoding amino acid residues Cys-49 to Asn-63 of the synthetic single-chain form of INSULIN (GYG). With these two primers, the synthetic single-chain form of INSULIN (GYG) was PCR amplified. Annealing and extension temperatures and times must be empirically determined for each specific primer pair and template.

The PCR product was purified (for example, using Wizard PCR Preps DNA Purification System (Promega Corp)) and then digested with Bsu36I and AscI. After further purification of the Bsu36I-AscI fragment by gel electrophoresis, the product was cloned into Bsu36I/AscI digested pScNHSA. A Not I fragment was further subcloned into pSAC35 to give construct ID #2250.

Further analysis of the N-terminus of the expressed albumin fusion protein by amino acid sequencing should confirm the presence of the expected mature HSA sequence (see below).

INSULIN albumin fusion proteins of the invention preferably comprise the mature form of HSA, i.e., Asp-25 to Leu-609, fused to either the N- or C-terminus of the synthetic single-chain analog of INSULIN, i.e., Phe-1 to Asn-62; the sequence corresponding to the C-peptide in the middle region of the proinsulin cDNA was replaced by C-domain of Insulin Growth Factor 1, "IGF-1" (GY32GSSSRRAPQT) (SEQ ID NO:2). In one embodiment of the invention, INSULIN albumin fusion proteins of the invention further comprise a signal sequence which directs the nascent fusion polypeptide in the secretory pathways of the host used for expression. In a further preferred embodiment, the signal peptide encoded by the signal sequence is removed, and the mature INSULIN albumin fusion protein is secreted directly into the culture medium. INSULIN albumin fusion proteins of the invention may comprise heterologous signal sequences including, but not limited to, MAF, INV, Ig, Fibulin B, Clusterin, Insulin-Like Growth Factor Binding Protein 4, variant HSA leader sequences including, but not limited to, a chimeric HSA/MAF leader sequence, or other heterologous signal sequences known in the art. In a preferred embodiment, INSULIN albumin fusion proteins of the invention comprise the native INSULIN. In further preferred embodiments, the INSULIN albumin fusion proteins of the invention further comprise an N-terminal methionine residue. Polynucleotides encoding these polypeptides, including fragments and/or variants, are also encompassed by the invention.

Expression and Purification of Construct ID 2250.

Expression in Yeast S. cerevisiae.

Construct 2250 can be transformed into yeast S. cerevisiae by methods known in the art (see Example 3). Expression levels can be examined by immunoblot detection with anti-HSA serum as the primary antibody.

Purification from Yeast S. cerevisiae Cell Supernatant.

The cell supernatant containing the secreted INSULIN (GYG) albumin fusion protein expressed from construct ID #2250 in yeast S. cerevisiae can be purified as described in Example 4. N-terminal sequencing of the albumin fusion protein should result in the sequence DAHKS which corresponds to the amino terminus of the mature form of HSA.

In vitro [$^3$H]-2-Deoxyglucose Uptake Assay in the Presence of the Albumin Fusion Protein Encoded by Construct 2250.

Methods

The in vitro assay to measure the glucose uptake in 3T3-L1 adipocytes in the presence of the INSULIN (GYG) albumin fusion protein encoded by construct 2250 was carried out as described below. Other assays known in the art that may be used to test INSULIN (GYG) albumin fusion proteins' include, but are not limited to, L6 Rat Myoblast Proliferation Assay via glycogen synthase kinase-3 (GSK-3) and H4Ile reporter assays including the rat Malic Enzyme Promoter (rMEP)-SEAP, Sterol Regulatory Element Binding Protein (SREBP)-SEAP, Fatty Acid Synthetase (FAS)-SEAP, and PhosphoEnolPyruvate CarboxyKinase (PEPCK)-SEAP reporters.

Results

Figure 18:
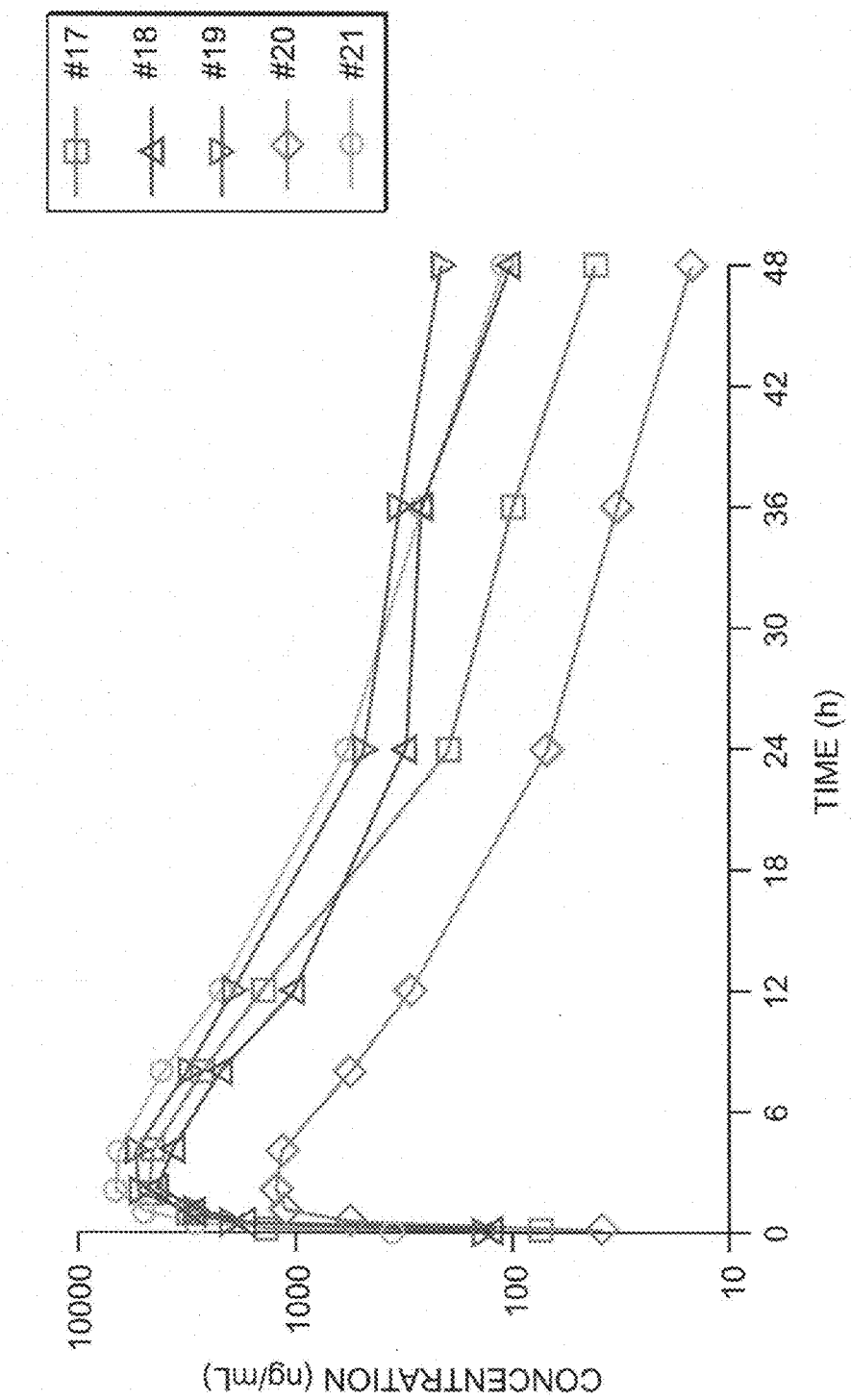
FIG. 18 shows serum albulin concentration time curves following a single IS dose of 3 mg (454/73.1).

The supernatant derived from transformed yeast S. cerevisiae expressing insulin albumin fusion encoded by construct 2250 demonstrated glucose uptake/transport activity in 3T3-L1 adipocytes (see FIG. 18).

In Vitro Pancreatic Cell-Lines Proliferation Assay in the Presence of the Albumin Fusion Protein Encoded by Construct 2250.

Methods

The in vitro assay to measure the differentiation and proliferation of ductal epithelium pancreatic ARIP cell-line into insulin-producing beta cells and/or to measure the proliferation of the insulin-producing RIN-M beta cell-line in the presence of the INSULIN (GYG) albumin fusion protein encoded by construct 2250 can be carried out as described below under heading: "In vitro Assay of [$^3$H]-Thymidine Incorporation into Pancreatic Cell-lines."

The Activity of the Albumin Fusion Protein Encoded by Construct 2250 can be Assayed In Vivo Using Diabetic NOD and/or NIDDM Mouse Models.

The activity of the INSULIN (GYG) albumin fusion protein encoded by construct 2250 can be measured using NOD and/or NIDDM mouse models described below under the headings, "Occurrence of Diabetes in NOD Mice," "Histological Examination of NOD Mice," and "In vivo Mouse Model of NIDDM."

Example 9

Construct ID 2255, Insulin (GYG)-HSA, Generation

Construct ID 2255, pSAC35.INSULIN (GYG).F1-N62.HSA, encodes for an INSULIN (GYG)-HSA fusion protein which comprises the HSA chimeric leader sequence of HSA fused to the amino-terminus of the synthetic single-chain long-acting insulin analog (INSULIN (GY32G)) with a Tyr in position 32, which is, in turn, fused to the mature form of HSA, cloned into the yeast S. cerevisiae expression vector pSAC35.

Cloning of INSULIN (GYG) cDNA for Construct 2255.

The DNA encoding the synthetic single-chain form of INSULIN (GYG) was PCR generated using four overlapping primers. The sequence corresponding to the C-peptide in the middle region of the proinsulin cDNA was replaced by the C-domain of Insulin Growth Factor 1, "IGF-1" (GY32GSSSRRAPQT) (SEQ ID NO:2), to avoid the need for proinsulin processing and to ensure proper folding of the single-chain protein. The sequence was codon optimized for expression in yeast S. cerevisiae. The PCR fragment was digested with Sal I/Cla I and subcloned into Xho I/Cla I digested pScCHSA. A Not I fragment was then subcloned into the pSAC35 plasmid. Construct ID #2255 encodes for the chimeric leader sequence of HSA fused to the amino-terminus of the synthetic single-chain form of INSULIN (GYG) followed by the mature form of HSA.

The 5' and 3' primers of the four overlapping oligonucleotides suitable for PCR amplification of the polynucleotide encoding the synthetic single-chain form of INSULIN (GYG), INSULIN (GYG)-3 and INSULIN (GYG)-4, were synthesized: 33 INSULIN (GYG)-3: 5'-TCCAG- GAGCGTCGACAAAAGATTCGTTAACCA ACACTTGTGTGGTTCTCACTTGGTTGAAGCTTTGT ACTTGGTTTGTGGTGAA-3' (SEQ ID NO:70) INSULIN (GYG)-4: 5'-AGACTTTAAATCGATGAGCAACCTCACTCTTG TGTGCATCGTTACAGTAGTTTTCCAATTGGTACAA AGAACAAATAGAAGTACAA-3' (SEQ ID NO:71).

INSULIN (GYG)-3 incorporates a Sal I cloning site and the DNA encoding the first 21 amino acids of the ORF of the synthetic single-chain form of INSULIN (GYG). INSULIN (GYG)-4 incorporates a Cla I site; and the Cla I site and the DNA following it are the reverse complement of DNA encoding the first 10 amino acids of the mature HSA protein. INSULIN (GYG)-4 also includes the reverse complement of the 46 nucleotides encoding the last 15 amino acid residues Cys-49 to Asn-63 of the synthetic single-chain form of INSULIN (GYG). With these two primers, the synthetic single-chain INSULIN (GYG) protein was generated by annealing, extension of the annealed primers, digestion with Sal I and Cla I, and subcloning into Xho I/Cla I digested pScCHSA. The Not I fragment from this clone was then ligated into the Not I site of pSAC35 to generate construct ID 2255. Construct ID #2255 encodes an albumin fusion protein containing the chimeric leader sequence, the synthetic single-chain form of INSULIN (GYG), and the mature form of HSA, otherwise referred to as "IN101NHY."

Further analysis of the N-terminus of the expressed albumin fusion protein by amino acid sequencing should confirm the presence of the expected INSULIN (GYG) sequence (see below).

INSULIN albumin fusion proteins of the invention preferably comprise the mature form of HSA, i.e., Asp-25 to Leu-609, fused to either the N- or C-terminus of the synthetic single-chain analog of INSULIN, i.e., Phe-1 to Asn-62; the sequence corresponding to the C-peptide in the middle region of the proinsulin cDNA was replaced by the C-domain of Insulin Growth Factor 1, "IGF-1" (GY32GSSSRRAPQT) (SEQ ID NO:2). In one embodiment of the invention, INSULIN albumin fusion proteins of the invention further comprise a signal sequence which directs the nascent fusion polypeptide in the secretory pathways of the host used for expression. In a further preferred embodiment, the signal peptide encoded by the signal sequence is removed, and the mature INSULIN albumin fusion protein is secreted directly into the culture medium. INSULIN albumin fusion proteins of the invention may comprise heterologous signal sequences including, but not limited to, MAF, INV, Ig, Fibulin B, Clusterin, Insulin-Like Growth Factor Binding Protein 4, variant HSA leader sequences including, but not limited to, a chimeric HSA/MAF leader sequence, or other heterologous signal sequences known in the art. In a preferred embodiment, INSULIN albumin fusion proteins of the invention comprise the native INSULIN. In further preferred embodiments, the INSULIN albumin fusion proteins of the invention further comprise an N-terminal methionine residue. Polynucleotides encoding these polypeptides, including fragments and/or variants, are also encompassed by the invention.

Expression and Purification of Construct ID 2255.

Expression in Yeast S. cerevisiae.

Construct 2255 can be transformed into yeast S. cerevisiae by methods known in the art (see Example 3). Expression levels can be examined by immunoblot detection with anti-HSA serum as the primary antibody.

Purification from Yeast S. cerevisiae Cell Supernatant.

The cell supernatant containing the secreted INSULIN (GYG) albumin fusion protein expressed from construct ID #2255 in yeast S. cerevisiae can be purified as described in Example 4. N-terminal sequencing of the expressed and purified albumin fusion protein should generate FVNQH (SEQ ID NO:76) which corresponds to the amino terminus of the synthetic single-chain long-acting insulin analog (INSULIN (GY32G) (SEQ ID NO:2)).

In vitro [$^3$H]-2-Deoxyglucose Uptake Assay in the Presence of the Albumin Fusion Protein Encoded by Construct 2255.

Methods

The in vitro assay to measure the glucose uptake in 3T3-L1 adipocytes in the presence of the INSULIN (GYG) albumin fusion protein encoded by construct 2255 can be carried out as described below. Other assays known in the art that may be used to test INSULIN (GYG) albumin fusion proteins' include, but are not limited to, L6 Rat Myoblast Proliferation Assay via glycogen synthase kinase-3 (GSK-3) and H4IIe reporter assays including the rat Malic Enzyme Promoter (rMEP)-SEAP, Sterol Regulatory Element Binding Protein (SREBP)-SEAP, Fatty Acid Synthetase (FAS)-SEAP, and PhosphoEnolPyruvate CarboxyKinase (PEPCK)-SEAP reporters.

In Vitro Pancreatic Cell-Lines Proliferation Assay in the Presence of the Albumin Fusion Protein Encoded by Construct 2255.

Methods

The in vitro assay to measure the differentiation and proliferation of ductal epithelium pancreatic ARIP cell-line into insulin-producing beta cells and/or to measure the proliferation of the insulin-producing RIN-M beta cell-line in the presence of the INSULIN (GYG) albumin fusion protein encoded by construct 2255 can be carried out as described below under heading: "In vitro Assay of [$^3$H]-Thymidine Incorporation into Pancreatic Cell-lines."

The Activity of the Albumin Fusion Protein Encoded by Construct 2255 can be Assayed In Vivo Using Diabetic NOD and/or NIDDM Mouse Models.

The activity of the INSULIN (GYG) albumin fusion protein encoded by construct 2255 can be measured using NOD and/or NIDDM mouse models described below under the headings, "Occurrence of Diabetes in NOD Mice," "Histological Examination of NOD Mice," and "In vivo Mouse Model of NIDDM."

Example 10

Construct ID 2276, HSA-Insulin (GGG), Generation

Construct ID 2276, pSAC35.HSA.INSULIN (GGG).F1-N58, encodes for an HSA-INSULIN (GGG) fusion protein which comprises full length HSA, including the native HSA leader sequence fused to the amino-terminus of the synthetic single-chain long-acting insulin analog (INSULIN (GG32G)) with a Gly at position 32, cloned into the yeast S. cerevisiae expression vector pSAC35.

Cloning of INSULIN (GGG) cDNA for Construct 2276.

The DNA encoding the synthetic single-chain form of INSULIN (GGG) was PCR generated using four overlapping primers. The sequence corresponding to the C-peptide in the middle region of the proinsulin cDNA was replaced by the synthetic linker "GG32GPGKR" (SEQ ID NO:29) to avoid the need for proinsulin processing and to ensure proper folding of the single-chain protein. The sequence was codon optimized for expression in yeast S. cerevisiae. The PCR fragment was digested and subcloned into Bsu 36I/Asc I digested pScNHSA. A Not I fragment was then subcloned into the pSAC35 plasmid. Construct ID #2276 encodes for full length HSA, including the native HSA leader sequence fused to the amino-terminus of the synthetic single-chain form of INSULIN (GGG).

The 5' and 3' primers of the four overlapping oligonucleotides suitable for PCR amplification of the polynucleotide encoding the synthetic single-chain form of INSULIN (GGG), INSULIN (GGG)-1 and INSULIN (GGG)-2, were synthesized: 34 INSULIN (GGG)-5: 5'-GTCAAGCTGC-CTTAGGCTTATTCGTTAACCAA CACTTGTGTGGT-TCTCACTTGGTTGAAGCTTTGTA CTTGGTTTGTG-GTGAA-3' (SEQ ID NO:68) INSULIN (GGG)-6: 5'-ATCGCATATGGCGCGCCCTATTAGTTACAGTA GTTTTCCAATTGGTACAAAGAACAAATAGAAGTAC AA-3' (SEQ ID NO:69).

INSULIN (GGG)-5 incorporates a Bsu 36I cloning site and encodes the first 21 amino acids of the ORF of the synthetic single-chain form of INSULIN (GGG). INSULIN (GGG)-6 incorporates an Asc I site. INSULIN (GGG)-6 also includes the reverse complement of the last 49 nucleotides encoding amino acid residues Cys-44 to Asn-58 of the synthetic single-chain form of INSULIN (GGG). With these two primers, the synthetic single-chain form of INSULIN (GGG) was PCR amplified. Annealing and extension temperatures and times must be empirically determined for each specific primer pair and template.

The PCR product was purified (for example, using Wizard PCR Preps DNA Purification System (Promega Corp)) and then digested with Bsu36I and AscI. After further purification of the Bsu36I-AscI fragment by gel electrophoresis, the product was cloned into Bsu36I/AscI digested pScNHSA. A Not I fragment was further subcloned into pSAC35 to give construct ID #2276.

Further, analysis of the N-terminus of the expressed albumin fusion protein by amino acid sequencing should confirm the presence of the expected mature HSA sequence (see below).

INSULIN albumin fusion proteins of the invention preferably comprise the mature form of HSA, i.e., Asp-25 to Leu-609, fused to either the N- or C-terminus of the synthetic single-chain analog of INSULIN, i.e., Phe-1 to Asn-58; the sequence corresponding to the C-peptide in the middle region of the proinsulin cDNA was replaced by the synthetic linker "GG32GPGKR" (SEQ ID NO:29). In one embodiment of the invention, INSULIN albumin fusion proteins of the invention further comprise a signal sequence which directs the nascent fusion polypeptide in the secretory pathways of the host used for expression. In a further preferred embodiment, the signal peptide encoded by the signal sequence is removed, and the mature INSULIN albumin fusion protein is secreted directly into the culture medium. INSULIN albumin fusion proteins of the invention may comprise heterologous signal sequences including, but not limited to, MAF, INV, Ig, Fibulin B, Clusterin, Insulin-Like Growth Factor Binding Protein 4, variant HSA leader sequences including, but not limited to, a chimeric HSA/MAF leader sequence, or other heterologous signal sequences known in the art. In a preferred embodiment, INSULIN albumin fusion proteins of the invention comprise the native INSULIN. In further preferred embodiments, the INSULIN albumin fusion proteins of the invention further comprise an N-terminal methionine residue. Polynucleotides encoding these polypeptides, including fragments and/or variants, are also encompassed by the invention.

Expression and Purification of Construct ID 2276.
Expression in Yeast S. cerevisiae.
Construct 2276 can be transformed into yeast S. cerevisiae by methods known in the art (see Example 3). Expression levels can be examined by immunoblot detection with anti-HSA serum as the primary antibody.

Purification from Yeast S. cerevisiae Cell Supernatant.

The cell supernatant containing the secreted INSULIN (GGG) albumin fusion protein expressed from construct ID #2276 in yeast S. cerevisiae can be purified as described in Example 4. N-terminal sequencing should yield DAHKS which corresponds to the amino terminus of the mature form of HSA.

In Vitro [$^3$H]-2-Deoxyglucose Uptake Assay in the Presence of the Albumin Fusion Protein Encoded by Construct 2276.

Methods

The in vitro assay to measure the glucose uptake in 3T3-L1 adipocytes in the presence of the INSULIN (GGG) albumin fusion protein encoded by construct 2276 was carried out as described below. Other assays known in the art that may be used to test INSULIN (GGG) albumin fusion proteins' include, but are not limited to, L6 Rat Myoblast Proliferation Assay via glycogen synthase kinase-3 (GSK-3) and H4IIe reporter assays including the rat Malic Enzyme Promoter (rMEP)-SEAP, Sterol Regulatory Element Binding Protein (SREBP)-SEAP, Fatty Acid Synthetase (FAS)-SEAP, and PhosphoEnolPyruvate CarboxyKinase (PEPCK)-SEAP reporters.

Results

The supernatant derived from transformed yeast S. cerevisiae expressing insulin albumin fusion encoded by construct 2276 demonstrated glucose uptake/transport activity in 3T3-L1 adipocytes (see FIG. 18).

In Vitro Pancreatic Cell-Lines Proliferation Assay in the Presence of the Albumin Fusion Protein Encoded by Construct 2276.

Methods

The in vitro assay to measure the differentiation and proliferation of ductal epithelium pancreatic ARIP cell-line into insulin-producing beta cells and/or to measure the proliferation of the insulin-producing RIN-M beta cell-line in the presence of the INSULIN (GGG) albumin fusion protein encoded by construct 2276 can be carried out as described below under heading: "In vitro Assay of [$^3$H]-Thymidine Incorporation into Pancreatic Cell-lines."

The Activity of the Albumin Fusion Protein Encoded by Construct 2276 can be Assayed In Vivo Using Diabetic NOD and/or NIDDM Mouse Models.

The activity of the INSULIN (GGG) albumin fusion protein encoded by construct 2276 can be measured using NOD and/or NIDDM mouse models described below under the headings, "Occurrence of Diabetes in NOD Mice," "Histological Examination of NOD Mice," and "In vivo Mouse Model of NIDDM."

Example 11

Construct ID 2278, Insulin (GGG)-HSA, Generation

Construct ID 2278, pSAC35.INSULIN (GGG).HSA, encodes for an INSULIN (GGG)-HSA fusion protein which comprises the HSA chimeric leader sequence of HSA fused to the amino-terminus of the synthetic single-chain long-acting insulin analog (INSULIN (GG32G)) with a Gly in position 32, which is, in turn, fused to the mature form of HSA, cloned into the yeast S. cerevisiae expression vector pSAC35.

Cloning of INSULIN (GGG) cDNA for Construct 2278.

The DNA encoding the synthetic single-chain form of INSULIN (GGG) was PCR generated using four overlapping primers. The sequence corresponding to the C-peptide in the middle region of the proinsulin cDNA was replaced by the synthetic linker "GG32GPGKR" (SEQ ID NO:29) to avoid the need for proinsulin processing and to ensure proper folding of the single-chain protein. The sequence was codon optimized for expression in yeast S. cerevisiae. The PCR fragment was digested with Sal I/Cla I and subcloned into Xho I/Cla I digested pScCHSA. A Not I fragment was then subcloned into the pSAC35 plasmid. Construct ID #2278 encodes for the chimeric leader sequence of HSA fused to the amino-terminus of the synthetic single-chain form of INSULIN (GGG) followed by the mature form of HSA.

The 5' and 3' primers of the four overlapping oligonucleotides suitable for PCR amplification of the polynucleotide encoding the synthetic single-chain form of INSULIN (GGG), INSULIN (GGG)-7 and INSULIN (GGG)-8, were synthesized: 35 INSULIN (GGG)-7: 5'-TCCAG-GAGCGTCGACAAAAGATTCGTTAACCA ACACTT-GTGTGGTTCTCACTTGGTTGAAGCTTTGT ACTTG-GTTTG TGGTGAA-3' (SEQ ID NO:70) INSULIN (GGG)-8: 5'-AGACTTTAAATCGATGAGCAACCTCACTCTTG TGTGCATCGTTACAGTAGTTTTCCAATTGGTACAA AGAACAAATAGAAG TACAA-3' (SEQ ID NO:71).

INSULIN (GGG)-7 incorporates a Sal I cloning site and the DNA encoding the first 21 amino acids of the ORF of the synthetic single-chain form of INSULIN (GGG). INSULIN (GGG)-8 incorporates a Cla I site; and the Cla I site and the DNA following it are the reverse complement of DNA encoding the first 10 amino acids of the mature HSA protein. INSULIN (GGG)-8 also includes the reverse complement of the 46 nucleotides encoding the last 15 amino acid residues Cys-44 to Asn-58 of the synthetic single-chain form of INSULIN (GGG). With these two primers, the synthetic single-chain INSULIN (GGG) protein was generated by annealing, extension of the annealed primers, digestion with Sal I and Cla I, and subcloning into Xho I/Cla I digested pScCHSA. The Not I fragment from this clone was then ligated into the Not I site of pSAC35 to generate construct ID 2278. Construct ID #2278 encodes an albumin fusion protein containing the chimeric leader sequence, the synthetic single-chain form of INSULIN (GGG), and the mature form of HSA otherwise referred to as "IN100NHY."

Further, analysis of the N-terminus of the expressed albumin fusion protein by amino acid sequencing should confirm the presence of the expected INSULIN (GGG) sequence (see below).

INSULIN albumin fusion proteins of the invention preferably comprise the mature form of HSA, i.e., Asp-25 to Leu-609, fused to either the N- or C-terminus of the synthetic single-chain analog of INSULIN, i.e., Phe-1 to Asn-58; the sequence corresponding to the C-peptide in the middle region of the proinsulin cDNA was replaced by the synthetic linker "GG32GPGKR." In one embodiment of the invention, INSULIN albumin fusion proteins of the invention further comprise a signal sequence which directs the nascent fusion polypeptide in the secretory pathways of the host used for expression. In a further preferred embodiment, the signal peptide encoded by the signal sequence is removed, and the mature INSULIN albumin fusion protein is secreted directly into the culture medium. INSULIN albumin fusion proteins of the invention may comprise heterologous signal sequences including, but not limited to, MAF, INV, Ig, Fibulin B, Clusterin, Insulin-Like Growth Factor Binding Protein 4, variant HSA leader sequences including, but not limited to, a chimeric HSA/MAF leader sequence, or other heterologous signal sequences known in the art. In a preferred embodiment, INSULIN albumin fusion proteins of the invention comprise the native INSULIN. In further preferred embodiments, the INSULIN albumin fusion proteins of the invention further comprise an N-terminal methionine residue. Polynucleotides encoding these polypeptides, including fragments and/or variants, are also encompassed by the invention.

Expression and Purification of Construct ID 2278.

Expression in Yeast S. cerevisiae.

Construct 2278 can be transformed into yeast S. cerevisiae by methods known in the art (see Example 3). Expression levels can be examined by immunoblot detection with anti-HSA serum as the primary antibody.

Purification from Yeast S. cerevisiae Cell Supernatant.

The cell supernatant containing the secreted INSULIN (GGG) albumin fusion protein expressed from construct ID #2278 in yeast S. cerevisiae can be purified as described in Example 4. N-terminal sequencing of the expressed and purified albumin fusion protein should generate FVNQH (SEQ ID NO:76) which corresponds to the amino terminus of the synthetic single-chain long-acting insulin analog (INSULIN (GG32G)).

In vitro [$^3$H]-2-Deoxyglucose Uptake Assay in the Presence of the Albumin Fusion Protein Encoded by Construct 2278.

Methods

The in vitro assay to measure the glucose uptake in 3T3-L1 adipocytes in the presence of the INSULIN (GGG) albumin fusion protein encoded by construct 2278 can be carried out as described below. Other assays known in the art that may be used to test INSULIN (GGG) albumin fusion proteins' include, but are not limited to, L6 Rat Myoblast Proliferation Assay via glycogen synthase kinase-3 (GSK-3) and H4IIe reporter assays including the rat Malic Enzyme Promoter (rMEP)-SEAP, Sterol Regulatory Element Binding Protein (SREBP)-SEAP, Fatty Acid Synthetase (FAS)-SEAP, and PhosphoEnolPyruvate CarboxyKinase (PEPCK)-SEAP reporters.

In Vitro Pancreatic Cell-Lines Proliferation Assay in the Presence of the Albumin Fusion Protein Encoded by Construct 2278.

Methods

The in vitro assay to measure the differentiation and proliferation of ductal epithelium pancreatic ARIP cell-line into insulin-producing beta cells and/or to measure the proliferation of the insulin-producing RIN-M beta cell-line in the presence of the INSULIN (GGG) albumin fusion protein encoded by construct 2278 can be carried out as described below under heading: "In vitro Assay of [$^3$H]-Thymidine Incorporation into Pancreatic Cell-lines."

The Activity of the Albumin Fusion Protein Encoded by Construct 2278 can be Assayed In Vivo Using Diabetic NOD and/or NIDDM Mouse Models.

The activity of the INSULIN (GGG) albumin fusion protein encoded by construct 2278 can be measured using NOD and/or NIDDM mouse models described below under the headings, "Occurrence of Diabetes in NOD Mice," "Histological Examination of NOD Mice," and "In vivo Mouse Model of NIDDM."

Example 12

Indications for Insulin Albumin Fusion Proteins

Results from in vitro assays described above indicate that insulin albumin fusion proteins are useful for the treatment, prevention, and/or diagnosis of hyperglycemia, insulin resistance, insulin deficiency, hyperlipidemia, hyperketonemia, and diabetes mellitus, Type 1 and Type 2 diabetes.

Example 13

Isolation of a Selected cDNA Clone from the Deposited Sample

Many of the albumin fusion constructs of the invention have been deposited with the ATCC as shown in Table 3. The albumin fusion constructs may comprise any one of the following expression vectors: the yeast *S. cerevisiae* expression vector pSAC35, the mammalian expression vector pC4, or the mammalian expression vector pEE12.1.

pSAC35 (Sleep et al., 1990, Biotechnology 8:42), pC4 (ATCC Accession No. 209646; Cullen et al., Molecular and Cellular Biology, 438-447 (1985); Boshart et al., Cell 41: 521-530 (1985)), and pEE12.1 (Lonza Biologics, Inc.; Stephens and Cockett, Nucl. Acids Res. 17: 7110 (1989); International Publication #WO 89/01036; Murphy et al., *Biochem J.* 227: 277-279 (1991); Bebbington et al., *Bio/Technology* 10:169-175 (1992); U.S. Pat. No. 5,122,464; International Publication #WO 86/05807) vectors comprise an ampicillin resistance gene for growth in bacterial cells. These vectors and/or an albumin fusion construct comprising them can be transformed into an *E. coli* strain such as Stratagene XL-1 Blue (Stratagene Cloning Systems, Inc., 11011 N. Torrey Pines Road, La Jolla, Calif., 92037) using techniques described in the art such as Hanahan, spread onto Luria-Broth agar plates containing 100 µg/mL ampicillin, and grown overnight at 37° C.

The deposited material in the sample assigned the ATCC Deposit Number cited in Table 3 for any given albumin fusion construct also may contain one or more additional albumin fusion constructs, each encoding different albumin fusion proteins. Thus, deposits sharing the same ATCC Deposit Number contain at least an albumin fusion construct identified in the corresponding row of Table 3.

Two approaches can be used to isolate a particular albumin fusion construct from the deposited sample of plasmid DNAs cited for that albumin fusion construct in Table 3.

Method 1: Screening

First, an albumin fusion construct may be directly isolated by screening the sample of deposited plasmid DNAs using a polynucleotide probe corresponding to the sequence of the construct using methods known in the art. For example, a specific polynucleotide with 30-40 nucleotides may be synthesized using an Applied Biosystems DNA synthesizer according to the sequence reported. The oligonucleotide can be labeled, for instance, with 32P-.gamma.-ATP using T4 polynucleotide kinase and purified according to routine methods. (E.g., Maniatis et al., Molecular Cloning: A Laboratory Manual, Cold Spring Harbor Press, Cold Spring, N.Y. (1982)). The albumin fusion construct from a given ATCC deposit is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Method 2: PCR

Alternatively, DNA encoding a given albumin fusion protein may be amplified from a sample of a deposited albumin fusion construct, for example, by using two primers of 17-20 nucleotides that hybridize to the deposited albumin fusion construct 5' and 3' to the DNA encoding a given albumin fusion protein. The polymerase chain reaction is carried out under routine conditions, for instance, in 25 µl of reaction mixture with 0.5 ug of the above cDNA template. A convenient reaction mixture is 1.5-5 mM MgCl2, 0.01% (w/v) gelatin, 20 µM each of dATP, dCTP, dGTP, dTTP, 25 µmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are known in the art. For instance, a method similar to 5' RACE is available for generating the missing 5' end of a desired full-length transcript. (Fromont-Racine et al., Nucleic Acids Res., 21(7): 1683-1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 14

[$3^H$]-2-Deoxyglucose Uptake Assay

Adipose, skeletal muscle, and liver are insulin-sensitive tissues. Insulin can stimulate glucose uptake/transport into these tissues. In the case of adipose and skeletal muscle, insulin initiates the signal transduction that eventually leads to the translocation of the glucose transporter 4 molecule, GLUT4, from a specialized intracellular compartment to the cell surface. Once on the cell surface, GLUT4 allows for glucose uptake/transport.

[$3^H$]-2-Deoxyglucose Uptake

A number of adipose and muscle related cell-lines can be used to test for glucose uptake/transport activity in the absence or presence of a combination of any one or more of the therapeutic drugs listed for the treatment of diabetes mellitus. In particular, the 3T3-L1 murine fibroblast cells and the L6 murine skeletal muscle cells can be differentiated into 3T3-L1 adipocytes and into myotubes, respectively, to serve as appropriate in vitro models for the [$3^H$]-2-deoxyglucose uptake assay (Urso et al., *J Biol Chem*, 274(43): 30864-73 (1999); Wang et al., *J Mol Endocrinol*, 19(3): 241-8 (1997); Haspel et al., *J Membr Biol*, 169 (1): 45-53 (1999); Tsakiridis et al., *Endocrinology*, 136(10): 4315-22 (1995)). Briefly, 2×105 cells/100 μL of adipocytes or differentiated L6 cells are transferred to 96-well Tissue-Culture, "TC," treated, i.e., coated with 50 μg/mL of poly-L-lysine, plates in post-differentiation medium and are incubated overnight at 37° C. in 5% CO2. The cells are first washed once with serum free low glucose DMEM medium and are then starved with 100 μL/well of the same medium and with 100 μL/well of either buffer or of a combination of any one or more of the therapeutic drugs listed for the treatment of diabetes mellitus, for example, increasing concentrations of 1 nM, 10 nM, and 100 nM of the therapeutics of the subject invention for 16 hours at 37° C. in the absence or presence of 1 nM insulin. The plates are washed three times with 100 μL/well of HEPES buffered saline. Insulin is added at 1 nM in HEPES buffered saline for 30 min at 37° C. in the presence of 10 μM labeled [$^3$H]-2-deoxyglucose (Amersham, #TRK672) and 10 □M unlabeled 2-deoxyglucose (SIGMA, D-3179). As control, the same conditions are carried out except in the absence of insulin. A final concentration of 10 μM cytochalasin B (SIGMA, C6762) is added at 100 μL/well in a separate well to measure the non-specific uptake. The cells are washed three times with HEPES buffered saline. Labeled, i.e., 10 μM of [$^3$H]-2-deoxyglucose, and unlabeled, i.e., 10 μM of 2-deoxyglucose, are added for 10 minutes at room temperature. The cells are washed three times with cold Phosphate Buffered Sal ine, "PBS." The cells are lysed upon the addition of 150 μL/well of 0.2 N NaOH and subsequent incubation with shaking for 20 minutes at room temperature. Samples are then transferred to a scintillation vial to which is added 5 mL of scintillation fluid. The vials are counted in a Beta-Scintillation counter. Uptake in duplicate conditions, the difference being the absence or presence of insulin, is determined with the following equation: [(Insulin counts per minute "cpm"–Non-Specific cpm)/(No Insulin cpm–Non-Specific cpm)]. Average responses fall within the limits of about 5-fold and 3-fold that of controls for adipocytes and myotubes, respectively.

Differentiation of Cells

The cells are allowed to become fully confluent in a T-75 cm2 flask. The medium is removed and replaced with 25 mL of pre-differentiation medium for 48 hours. The cells are incubated at 37° C., in 5% CO2, 85% humidity. After 48 hours, the pre-differentiation medium is removed and replaced with 25 mL differentiation medium for 48 hours. The cells are again incubated at 37° C., in 5% CO2, 85% humidity. After 48 hours, the medium is removed and replaced with 30 mL post-differentiation medium. Post-differentiation medium is maintained for 14-20 days or until complete differentiation is achieved. The medium is changed every 2-3 days. Human adipocytes can be purchased from Zen-Bio, INC (#SA-1096).

Example 15

In vitro Assay of [$^3$H]-Thymidine Incorporation into Pancreatic Cell-lines

It has recently been shown that GLP-1 induces differentiation of the rat pancreatic ductal epithelial cell-line ARIP in a time- and dose-dependent manner which is associated with an increase in Islet Duodenal Homeobox-1 (IDX-1) and insulin mRNA levels (Hui et al., 2001, Diabetes, 50(4): 785-96). The IDX-1 in turn increases mRNA levels of the GLP-1 receptor.

Cells Types Tested

RIN-M cells: These cells are available from the American Type Tissue Culture Collection (ATCC Cell Line Number CRL-2057). The RIN-M cell line was derived from a radiation induced transplantable rat islet cell tumor. The line was established from a nude mouse xenograft of the tumor. The cells produce and secrete islet polypeptide hormones, and produce L-dopa decarboxylase (a marker for cells having amine precursor uptake and decarboxylation, or APUD, activity).

ARIP cells: These are pancreatic exocrine cells of epithelial morphology available from the American Type Tissue Culture Collection (ATCC Cell Line Number CRL-1674). See also, references: Jessop, N. W. and Hay, R. J., "Characteristics of two rat pancreatic exocrine cell lines derived from transplantable tumors," *In Vitro* 16: 212, (1980); Cockell, M. et al., "Identification of a cell-specific DNA-binding activity that interacts with a transcriptional activator of genes expressed in the acinar pancreas," Mol. Cell. Biol. 9: 2464-2476, (1989); Roux, E., et al. "The cell-specific transcription factor PTF1 contains two different subunits that interact with the DNA" Genes Dev. 3: 1613-1624, (1989); and, Hui, H., et al., "Glucagon-like peptide 1 induces differentiation of islet duodenal homeobox-1-positive pancreatic ductal cells into insulin-secreting cells," Diabetes 50: 785-796 (2001).

Preparation of Cells

The RIN-M cell-line is grown in RPMI 1640 medium (Hyclone, #SH300027.01) with 10% fetal bovine serum (HyClone, #SH30088.03) and is subcultured every 6 to 8 days at a ratio of 1:3 to 1:6. The medium is changed every 3 to 4 days.

The ARIP (ATCC #CRL-1674) cell-line is grown in Ham's F12K medium (ATCC, #30-2004) with 2 mM L-glutamine adjusted to contain 1.5 g/L sodium bicarbonate and 10% fetal bovine serum. The ARIP cell-line is subcultured at a ratio of 1:3 to 1:6 twice per week. The medium is changed every 3 to 4 days.

Assay Protocol

The cells are seeded at 4000 cells/well in 96-well plates and cultured for 48 to 72 hours to 50% confluence. The cells are switched to serum-free media at 100 L/well. After incubation for 48-72 hours, serum and/or the therapeutics of the subject invention (e.g., albumin fusion proteins of the invention and fragments and variants thereof) are added to the well. Incubation persists for an additional 36 hours. [$^3$H]-Thymidine (5-20 Ci/mmol) (Amersham Pharmacia, #TRK120) is diluted to 1 microCuries/S microliters. After the 36 hour incubation, 5 microliters is added per well for a further 24 hours. The reaction is terminated by washing the cells gently with cold Phosphate-Buffered Sal ine, "PBS," once. The cells are then fixed with 100 microliters of 10% ice cold TCA for 15 min at 4° C. The PBS is removed and 200 microliters of 0.2 N NaOH is added. The plates are incubated for 1 hour at room temperature with shaking. The solution is transferred to a scintillation vial and 5 mL of scintillation fluid compatible with aqueous solutions is added and mixed vigorously. The vials are counted in a beta scintillation counter. As negative control, only buffer is used. As a positive control fetal calf serum is used.

Example 16

Assaying for Glycosuria

Glycosuria (i.e., excess sugar in the urine), can be readily assayed to provide an index of the disease state of diabetes mellitus. Excess urine in a patient sample as compared with a normal patient sample is symptomatic of IDDM and NIDDM. Efficacy of treatment of such a patient having IDDM and NIDDM is indicated by a resulting decrease in the amount of excess glucose in the urine. In a preferred embodiment for IDDM and NIDDM monitoring, urine samples from patients are assayed for the presence of glucose using techniques known in the art. Glycosuria in humans is defined by a urinary glucose concentration exceeding 100 mg per 100 ml. Excess sugar levels in those patients exhibiting glycosuria can be measured even more precisely by obtaining blood samples and assaying serum glucose.

Example 17

Occurrence of Diabetes in NOD Mice

Female NOD (non-obese diabetic) mice are characterized by displaying IDDM with a course which is similar to that found in humans, although the disease is more pronounced in female than male NOD mice. Hereinafter, unless otherwise stated, the term "NOD mouse" refers to a female NOD mouse. NOD mice have a progressive destruction of beta cells which is caused by a chronic autoimmune disease. Thus, NOD mice begin life with euglycemia, or normal blood glucose levels. By about 15 to 16 weeks of age, however, NOD mice start becoming hyperglycemic, indicating the destruction of the majority of their pancreatic beta cells and the corresponding inability of the pancreas to produce sufficient insulin. Thus, both the cause and the progression of the disease are similar to human IDDM patients.

In vivo assays of efficacy of the immunization regimens can be assessed in female NOD/LtJ mice (commercially available from The Jackson Laboratory, Bar Harbor, Me.). In the literature, it's reported that 80% of female mice develop diabetes by 24 weeks of age and onset of insulitis begins between 6-8 weeks age. NOD mice are inbred and highly responsive to a variety of immunoregulatory strategies. Adult NOD mice (6-8 weeks of age) have an average mass of 20-25 g.

These mice can be either untreated (control), treated with the therapeutics of the subject invention (e.g., albumin fusion proteins of the invention and fragments and variants thereof), alone or in combination with other therapeutic compounds stated above. The effect of these various treatments on the progression of diabetes can be measured as follows:

At 14 weeks of age, the female NOD mice can be phenotyped according to glucose tolerance. Glucose tolerance can be measured with the intraperitoneal glucose tolerance test (IPGTT). Briefly, blood is drawn from the paraorbital plexus at 0 minutes and 60 minutes after the intraperitoneal injection of glucose (1 g/kg body weight). Normal tolerance is defined as plasma glucose at 0 minutes of less than 144 mg %, or at 60 minutes of less than 160 mg %. Blood glucose levels are determined with a Glucometer Elite apparatus.

Based upon this phenotypic analysis, animals can be allocated to the different experimental groups. In particular, animals with more elevated blood glucose levels can be assigned to the impaired glucose tolerance group. The mice can be fed ad libitum and can be supplied with acidified water (pH 2.3).

The glucose tolerant and intolerant mice can be further subdivided into control, albumin fusion proteins of the subject invention, and albumin fusion proteins/therapeutic compounds combination groups. Mice in the control group can receive an interperitoneal injection of vehicle daily, six times per week. Mice in the albumin fusion group can receive an interperitoneal injection of the therapeutics of the subject invention (e.g., albumin fusion proteins of the invention and fragments and variants thereof) in vehicle daily, six times per week. Mice in the albumin fusion proteins/therapeutic compounds combination group can receive both albumin fusion proteins and combinations of therapeutic compounds as described above.

The level of urine glucose in the NOD mice can be determined on a bi-weekly basis using Labstix (Bayer Diagnostics, Hampshire, England). Weight and fluid intake can also be determined on a bi-weekly basis. The onset of diabetes is defined after the appearance of glucosuria on two consecutive determinations. After 10 weeks of treatment, an additional IPGTT can be performed and animals can be sacrificed the following day.

Over the 10 week course of treatment, control animals in both the glucose tolerant and glucose intolerant groups develop diabetes at a rate of 60% and 86%, respectively (see U.S. Pat. No. 5,866,546, Gross et al.). Thus, high rates of diabetes occur even in NOD mice which are initially glucose tolerant if no intervention is made.

Results can be confirmed by the measurement of blood glucose levels in NOD mice, before and after treatment. Blood glucose levels are measured as described above in both glucose tolerant and intolerant mice in all groups described.

In an alternative embodiment, the therapeutics of the subject invention can be quantified using spectrometric analysis and appropriate protein quantities can be resuspended prior to injection in 50 μl phosphate buffered saline (PBS) per dose. Two injections, one week apart, can be administered subcutaneously under the dorsal skin of each mouse. Monitoring can be performed on two separate occasions prior to immunization and can be performed weekly throughout the treatment and continued thereafter. Urine can be tested for glucose every week (Keto-Diastix®; Miles Inc., Kankakee, Ill.) and glycosuric mice can be checked for serum glucose (ExacTech®, MediSense, Inc., Waltham, Mass.). Diabetes is diagnosed when fasting glycemia is greater than 2.5 g/L.

Example 18

Histological Examination of NOD Mice

Histological examination of tissue samples from NOD mice can demonstrate the ability of the compositions of the present invention, and/or a combination of the compositions of the present invention with other therapeutic agents for diabetes, to increase the relative concentration of beta cells in the pancreas. The experimental method is as follows:

The mice described above can be sacrificed at the end of the treatment period and tissue samples can be taken from the pancreas. The samples can be fixed in 10% formalin in 0.9% saline and embedded in wax. Two sets of 5 serial 5 µm sections can be cut for immunolabeling at a cutting interval of 150 µm. Sections can be immunolabelled for insulin (guinea pig anti-insulin antisera dilution 1:1000, ICN Thames U.K.) and glucagon (rabbit anti-pancreatic glucagon antisera dilution 1:2000) and detected with peroxidase conjugated anti-guinea pig (Dako, High Wycombe, U.K.) or peroxidase conjugated anti-rabbit antisera (dilution 1:50, Dako).

The composition of the present invention may or may not have as strong an effect on the visible mass of beta cells as it does on the clinical manifestations of diabetes in glucose tolerant and glucose intolerant animals.

Example 19

In Vitro H4IIe-SEAP Reporter Assays Establishing Involvement in Insulin Action.

The Various H4IIe Reporters.

H4IIe/rMEP-SEAP: The malic enzyme promoter isolated from rat (rMEP) contains a PPAR-gamma element which is in the insulin pathway. This reporter construct is stably transfected into the liver H4IIe cell-line.

H4IIe/SREBP-SEAP: The sterol regulatory element binding protein (SREBP-1c) is a transcription factor which acts on the promoters of a number of insulin-responsive genes, for example, fatty acid synthetase (FAS), and which regulates expression of key genes in fatty acid metabolism in fibroblasts, adipocytes, and hepatocytes. SREBP-1c, also known as the adipocyte determination and differentiation factor 1 (ADD-1), is considered as the primary mediator of insulin effects on gene expression in adipose cells. Its activity is modulated by the levels of insulin, sterols, and glucose. This reporter construct is stably transfected into the liver H4IIe cell-line.

H4IIe/FAS-SEAP: The fatty acid synthetase reporter constructs contain a minimal SREBP-responsive FAS promoter. This reporter construct is stably transfected into the liver H4IIe cell-line.

H4IIe/PEPCK-SEAP: The phosphoenolpyruvate carboxykinase (PEPCK) promoter is the primary site of hormonal regulation of PEPCK gene transcription modulating PEPCK activity. PEPCK catalyzes a committed and rate-limiting step in hepatic gluconeogenesis and must therefore be carefully controlled to maintain blood glucose levels within normal limits. This reporter construct is stably transfected into the liver H4IIe cell-line.

These reporter constructs can also be stably transfected into 3T3-L1 fibroblasts and L6 myoblasts. These stable cell-lines are then differentiated into 3T3-L1 adipocytes and L6 myotubes as previously described. The differentiated cell-lines can then be used in the SEAP assay described below.

Growth and Assay Medium

The growth medium comprises 10% Fetal Bovine Serum (FBS), 10% Calf Serum, 1% NEAA, 1× penicillin/streptomycin, and 0.75 mg/mL G418 (for H4IIe/rFAS-SEAP and H4IIe/SREBP-SEAP) or 0.50 mg/mL G418 (for H4IIe/rMEP-SEAP). For H4IIe/PEPCK-SEAP, the growth medium consists of 10% FBS, 1% penicillin/streptomycin, 15 mM HEPES buffered saline, and 0.50 mg/mL G418.

The assay medium consists of low glucose DMEM medium (Life Technologies), 1% NEAA, 1× penicillin/streptomycin for the H4IIe/rFAS-SEAP, H4IIe/SREBP-SEAP, H4IIe/rMEP-SEAP reporters. The assay medium for H4IIe/PEPCK-SEAP reporter consists of 0.1% FBS, 1% penicillin/streptomycin, and 15 mM HEPES buffered saline.

Methods

The 96-well plates are seeded at 75,000 cells/well in 100 µL/well of growth medium until cells in log growth phase become adherent. Cells are starved for 48 hours by replacing growth medium with assay medium, 200 µL/well. (For H4IIe/PEPCK-SEAP cells, assay medium containing 0.5 µM dexamethasone is added at 100 µL/well and incubated for approximately 20 hours). The assay medium is replaced thereafter with 100 µL/well of fresh assay medium, and a 50 µL aliquot of cell supernatant obtained from transfected cell-lines expressing the therapeutics of the subject invention (e.g., albumin fusion proteins of the invention and fragments and variants thereof) is added to the well. Supernatants from empty vector transfected cell-lines are used as negative control. Addition of 10 nM and/or 100 nM insulin to the wells is used as positive control. After 48 hours of incubation, the conditioned media are harvested and SEAP activity measured (Phospha-Light System protocol, Tropix #BP2500). Briefly, samples are diluted 1:4 in dilution buffer and incubated at 65° C. for 30 minutes to inactivate the endogenous non-placental form of SEAP. An aliquot of 50 µL of the diluted samples is mixed with 50 µL of SEAP Assay Buffer which contains a mixture of inhibitors active against the non-placental SEAP isoenzymes and is incubated for another 5 minutes. An aliquot of 50 µL of CSPD chemiluminescent substrate which is diluted 1:20 in Emerald luminescence enhancer is added to the mixture and incubated for 15-20 minutes. Plates are read in a Dynex plate luminometer.

Example 20

Preparation of HA-Hormone Fusion Protein (Such as Insulin, LH, FSH)

The cDNA for the hormone of interest such as insulin can be isolated by a variety of means including but not exclusively, from cDNA libraries, by RT-PCR and by PCR using a series of overlapping synthetic oligonucleotide primers, all using standard methods. The nucleotide sequences for all of these proteins are known and available, for instance, in public databases such as GenBank. The cDNA can be tailored at the 5' and 3' ends to generate restriction sites, such that oligonucleotide linkers can be used, for cloning of the cDNA into a vector containing the cDNA for HA. This can be at the N or C-terminus with or without the use of a spacer sequence. The hormone cDNA is cloned into a vector such as pPPC0005 (FIG. 2), pScCHSA, pScNHSA, or pC4:HSA from which the complete expression cassette is then excised and inserted into the plasmid pSAC35 to allow the expression of the albumin fusion protein in yeast. The albumin fusion protein secreted from the yeast can then be collected and purified from the media and tested for its biological activity. For expression in mammalian cell lines a similar procedure is adopted except that the expression cassette used employs a mammalian promoter, leader sequence and terminator (See Example 1). This expression cassette is then excised and inserted into a plasmid suitable for the transfection of mammalian cell lines.

Example 21

Bacterial Expression of an Albumin Fusion Protein

A polynucleotide encoding an albumin fusion protein of the present invention comprising a bacterial signal sequence is amplified using PCR oligonucleotide primers corresponding to the 5' and 3' ends of the DNA sequence, to synthesize insertion fragments. The primers used to amplify the polynucleotide encoding insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, which expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D. 600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl or preferably in 8 M urea and concentrations greater than 0.14 M 2-mercaptoethanol by stirring for 3-4 hours at 4° C. (see, e.g., Burton et al., Eur. J. Biochem. 179:379-387 (1989)). The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8. The column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. Exemplary conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector, called pHE4a (ATCC Accession Number 209645, deposited on Feb. 25, 1998) which contains phage operator and promoter elements operatively linked to a polynucleotide encoding an albumin fusion protein of the present invention, called pHE4a. (ATCC Accession Number 209645, deposited on Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pU19 (LTI, Gaithersburg, Md.). The promoter and operator sequences are made synthetically.

DNA can be inserted into the pHE4a by restricting the vector with NdeI and XbaI, BamHI, XhoI, or Asp718, running the restricted product on a gel, and isolating the larger fragment (the stuffer fragment should be about 310 base pairs). The DNA insert is generated according to PCR protocols described herein or otherwise known in the art, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector may be substituted in the above protocol to express protein in a bacterial system.

Example 22

Expression of an Albumin Fusion Protein in Mammalian Cells

The albumin fusion proteins of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as, pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, but are not limited to, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the albumin fusion protein can be expressed in stable cell lines containing the polynucleotide encoding the albumin fusion protein integrated into a chromosome. The co-transfection with a selectable marker such as DHFR, gpt, neomycin, or hygromycin allows the identification and isolation of the transfected cells.

The transfected polynucleotide encoding the fusion protein can also be amplified to express large amounts of the encoded fusion protein. The DHFR (dihydrofolate reductase) marker is useful in developing cell lines that carry several hundred or even several thousand copies of the gene of interest. (See, e.g., Alt et al., J. Biol. Chem. 253:1357-1370 (1978); Hamlin et al., Biochem. et Biophys. Acta, 1097:107-143 (1990); Page et al., *Biotechnology* 9:64-68 (1991)). Another useful selection marker is the enzyme glutamine synthase (GS) (Murphy et al., *Biochem J.* 227: 277-279 (1991); Bebbington et al., *Bio/Technology* 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NS0 cells are often used for the production of proteins.

Derivatives of the plasmid pSV2-dhfr (ATCC Accession No. 37146), the expression vectors pC4 (ATCC Accession No. 209646) and pC6 (ATCC Accession No. 209647) contain the strong promoter (LTR) of the Rous Sarcoma Virus (Cullen et al., *Molecular and Cellular Biology*, 438-447 (March, 1985)) plus a fragment of the CMV-enhancer (Boshart et al., Cell 41:521-530 (1985)). Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide encoding an albumin fusion protein of the present invention is generated using techniques known in the art and this polynucleotide is amplified using PCR technology known in the art. If a naturally occurring signal sequence is used to produce the fusion protein of the present invention, the vector does not need a second signal peptide. Alternatively, if a naturally occurring signal sequence is not used, the vector can be-modified to include a heterologous signal sequence. (See, e.g., International Publication No. WO 96/34891.)

The amplified fragment encoding the fusion protein of the invention is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment encoding the albumin fusion protein of the invention is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five μg of the expression plasmid pC6 or pC4 is cotransfected with 0.5 vg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 mM). The same procedure is repeated until clones are obtained which grow at a concentration of 100-200 μM. Expression of the desired fusion protein is analyzed, for instance, by SDS-PAGE and Western blot or by reversed phase HPLC analysis.

Example 23

Transgenic Animals

The albumin fusion proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express fusion proteins of the invention in humans, as part of a gene therapy protocol.

Any technique known in the art may be used to introduce the polynucleotides encoding the albumin fusion proteins of the invention into animals to produce the founder lines of transgenic animals. Such techniques include, but are not limited to, pronuclear microinjection (Paterson et al., *Appl. Microbiol. Biotechnol.*, 40:691-698 (1994); Carver et al., *Biotechnology* (NY) 11:1263-1270 (1993); Wright et al., *Biotechnology* (NY) 9:830-834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148-6152 (1985)), blastocysts or embryos; gene targeting in embryonic stem cells (Thompson et al., *Cell* 56:313-321 (1989)); electroporation of cells or embryos (Lo, 1983, *Mol. Cell. Biol.* 3:1803-1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717-723 (1989); etc. For a review of such techniques, see Gordon, "Transgenic Animals," *Intl. Rev. Cytol.* 115:171-229 (1989), which is incorporated by reference herein in its entirety.

Any technique known in the art may be used to produce transgenic clones containing polynucleotides encoding albumin fusion proteins of the invention, for example, nuclear transfer into enucleated oocytes of nuclei from cultured embryonic, fetal, or adult cells induced to quiescence (Campell et al., *Nature* 380:64-66 (1996); Wilmut et al., Nature 385:810-813 (1997)).

The present invention provides for transgenic animals that carry the polynucleotides encoding the albumin fusion proteins of the invention in all their cells, as well as animals which carry these polynucleotides in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., *Proc. Natl. Acad. Sci. USA* 89:6232-6236 (1992)). The regulatory sequences required for such a cell-type specific activation will depend upon the particular cell type of interest, and will be apparent to those of skill in the art. When it is desired that the polynucleotide encoding the fusion protein of the invention be integrated into the chromosomal site of the endogenous gene corresponding to the therapeutic protein portion or albumin portion of the fusion protein of the invention, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the polynucleotide encoding the fusion protein of the invention has taken place. The level of mRNA expression of the polynucleotide encoding the fusion protein of the invention in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of fusion protein-expressing tissue may also be evaluated immunocytochemically or immunohistochemically using antibodies specific for the fusion protein.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene (i.e., polynucleotide encoding an albumin fusion protein of the invention) on a distinct background that is appropriate for an experimental model of interest.

Transgenic animals of the invention have uses which include, but are not limited to, animal model systems useful in elaborating the biological function of fusion proteins of the invention and the therapeutic protein and/or albumin component of the fusion protein of the invention, studying conditions and/or disorders associated with aberrant expression, and in screening for compounds effective in ameliorating such conditions and/or disorders.

Example 24

Figure 4:
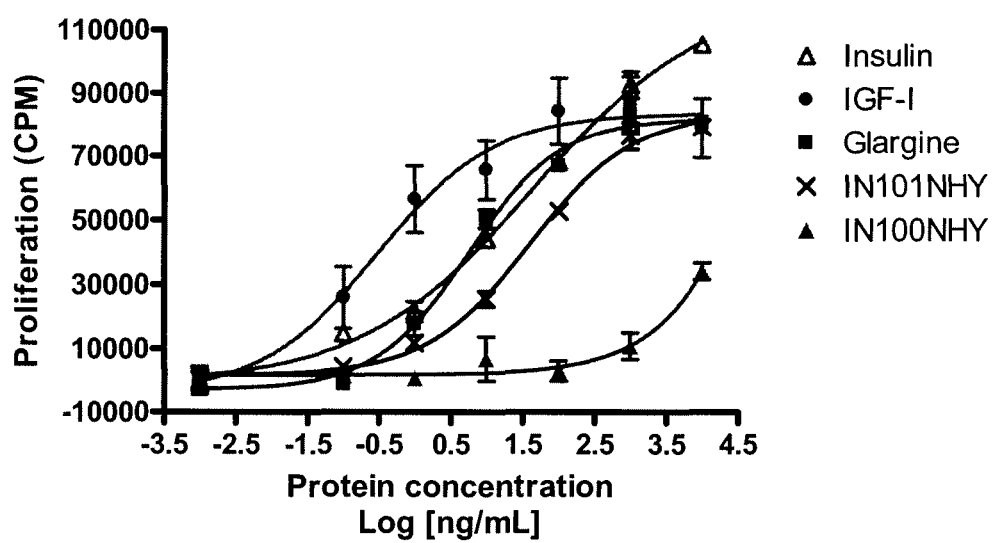
FIG. 4 shows L6 cell proliferation in response to insulin, IGF-I, Glargine (Lantus®, Aventis), or albumin-insulin fusion proteins (IN101NHY and IN100NHY).

Mitogenic activity of insulin, IGF-I, Glargine and albumin-insulin fusion proteins (IN101NHY, and IN100NHY) was assessed in L6 cells. L6 cells (ATCC, CRL-1458) were plated in a 96-well plate at 0.1×105 cells/100 μL well in 0.5% FBS DMEM medium. Indicated concentrations of insulin, IGF-1, Glargine (Lantus®, Aventis) and albumin fusion proteins were added and incubated at 37° C. for 2 days. Cell number was measured using CellTiter-Glo™ (Promega, Madison, Wis., USA) according to the manufacturer's instructions. All treatments were performed in triplicate and the data was analyzed using Prizm® (GraphPad, San Diego, Calif.). Results are presented in FIG. 4. The effective concentration at which 50% of maximum proliferation was observed (EC50) was calculated. Results are presented in Table 1. The results of these experiments indicate that the B-chain/A-chain linking sequence influences the mitogenic activity of the albumin-insulin fusion proteins.

TABLE 1

Dependence of Insulin-HSA Fusion Protein IGF-Like Activity on B-chain/A-chain Linking Sequence

| Treatment | Linking Sequence | EC50 |
|---|---|---|
| Insulin | — | 7 nM |
| Glargine | — | 0.9 nM |
| IGF-I | — | 0.04 nM |
| IN101NHY | GYGSSSRRAPQT (SEQ ID NO: 2) | 0.6 nM |
| IN100NHY | GGGPGKR (SEQ ID NO: 23) | >1 micron |

Example 25

Insulin receptor binding activity as measured by reporter activity dependent on insulin receptor stimulation of the fatty acid synthase promoter (FAS) and the sterol-responsive (and insulin responsive) enhancer binding protein (SREBP) was assessed for insulin, Glargine, and albumin-insulin fusion proteins (IN101NHY, and IN100NHY).

Figure 5:
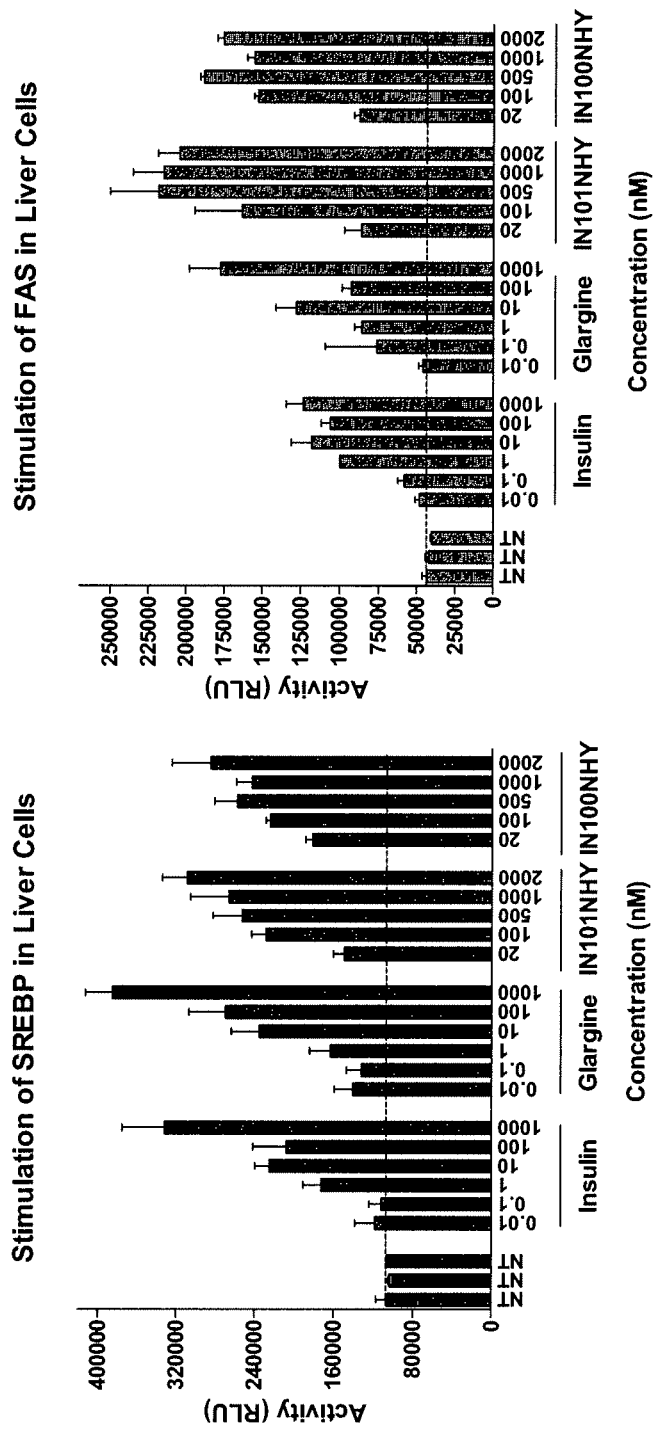
FIG. 5 shows stimulation of SREBP in liver cells (left graph) and stimulation of FAS in liver cells (right graph) in response to increasing concentrations of insulin, Glargine (Lantus®, Aventis), or albumin-insulin fusion proteins (IN101NHY and IN100NHY).

The FAS reporter construct was generated by incorporating a fragment containing −444 to +8 of the human fatty acid synthase promoter into pSEAP2-Basic (Clontech) in which a G418 selection cassette had been previously added. The SREBP reporter construct was generated by incorporating a repeating SREBP element (GGGGTACCTCATTGGC-CTGGGCGGCGCAGCCAAGCTGTCAGCCCATGTG-GCGTG GCCGCCCCTCGAGCGG) (SEQ ID NO:72) into pSEAP2-Promoter (Clontech) in which a G418 selection cassette had been previously added. H4IIE cells (ATCC, CRL-1548) were tranfected with these reporters and selected for G418 resistance as well as insulin-responsive SEAP activity. For assays, cells were serum deprived for 18-24 h and then fresh media was added with treatment compounds at varying concentrations. After a 48-h incubation conditioned medium was harvested and SEAP activity was measured using the Phospha-LIGHT™ System (Applied Biosystems) according the manufacturer's instructions. All treatments were performed in triplicate and the data was analyzed using Prizm® (GraphPad, San Diego, Calif.). Results are presented in FIG. 5 and indicate that the albumin fusion proteins exhibit similar binding activity as insulin and Glargine.

Example 26

Figure 6:
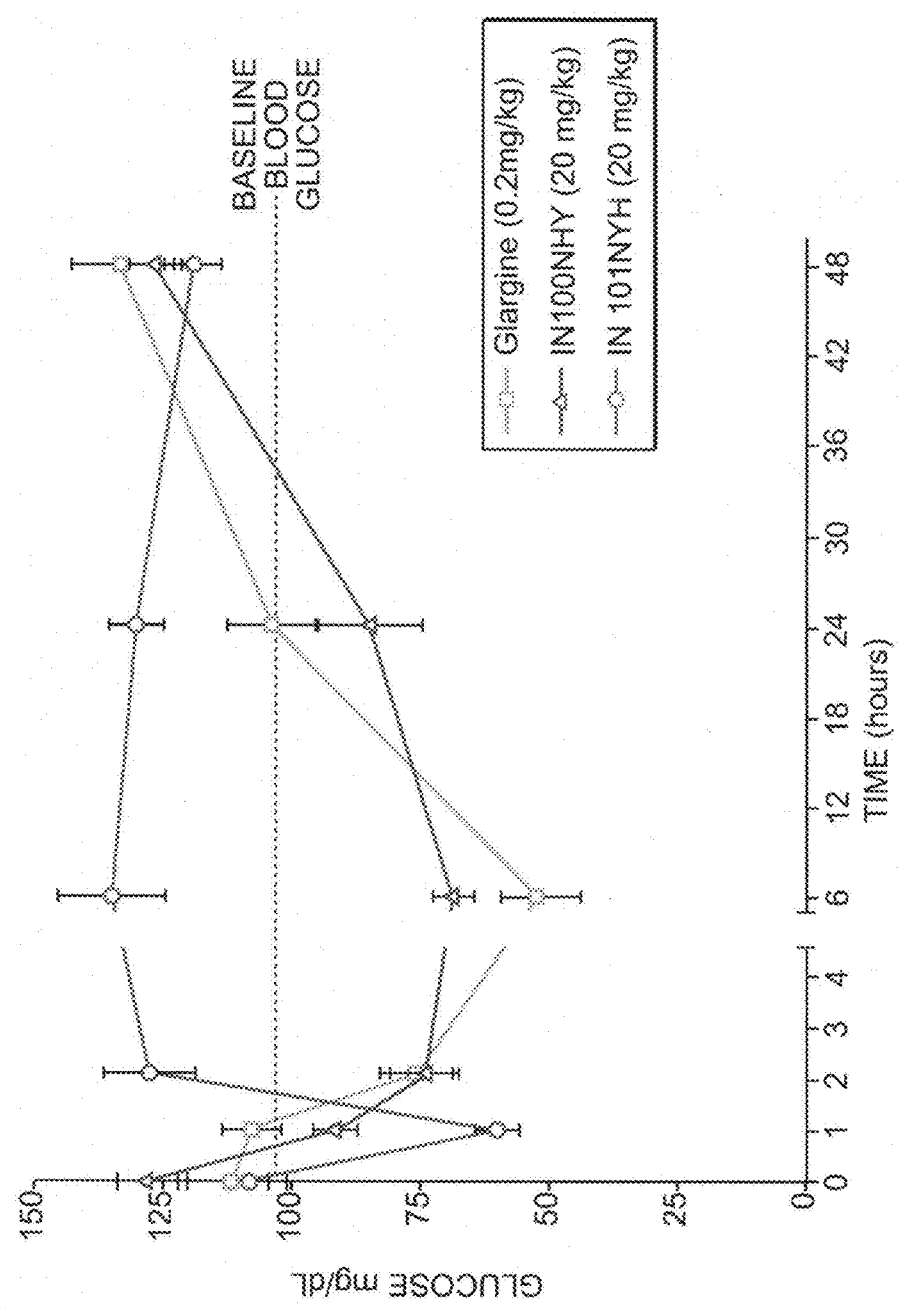
FIG. 6 shows plasma glucose levels in BalbC mice in response to Glargine (Lantus®, Aventis) or albumin-insulin fusion proteins (IN101NHY and IN100NHY).

Glargine and albumin fusion proteins IN100NHY and IN101NHY were administered by subcutaneous injection into 6 week old BalbC mice (n=8/group). Blood glucose levels were measured using a hand-held Freestyle™ blood glucose monitor at the given times and the results are presented in FIG. 6. Food was freely available to the mice throughout the experiment. In comparison to Glargine, the albumin-insulin fusion proteins exhibited longer-lived insulin activity, as indicated by lower glucose levels for a time period of about 2-6 hours after injection.

Example 27

Using the methods described in the Examples 1-11, vectors for expression albumin-insulin fusion proteins were prepared which included the following B-chain/A-chain linking sequences in Table 2:

TABLE 2

B-chain/A-chain Linking Sequences for Single-Chain Insulin/Albumin Fusion Proteins

| CoGenesys ID No. | Sequence | Description |
|---|---|---|
| 1 | NPNLPRLVR (SEQ ID NO: 18) | HSA fragment preferred fold |
| 2 | KDDNPNLPRLVR (SEQ ID NO: 19) | HSA fragment preferred fold |
| 3 | NDEMPAD (SEQ ID NO: 20) | HSA fragment preferred fold |
| 4 | GGGPGKR (SEQ ID NO: 29) | Synthetic |
| 5 | GGGPQT (SEQ ID NO: 21) | IGF-I Variant, Non-IGFR binding |
| 6 | GAGSSSRRAPQT (SEQ ID NO: 22) | IGF-I Variant, Non-IGFR binding |
| 7 | GGGPGAG (SEQ ID NO: 23) | Fragment of insulin C-peptide |
| 8 | GYGSSSRRAPQT (SEQ ID NO: 2) | IGF-1 C-peptide |

Example 28

The mitogenic activity of Albulin (IN100NHY, C-peptide=GGGPGKR (SEQ ID NO:29)) was compared to the mitogenic activity of native insulin and other insulin analogs (Table 3).

Example 29

Figure 7:
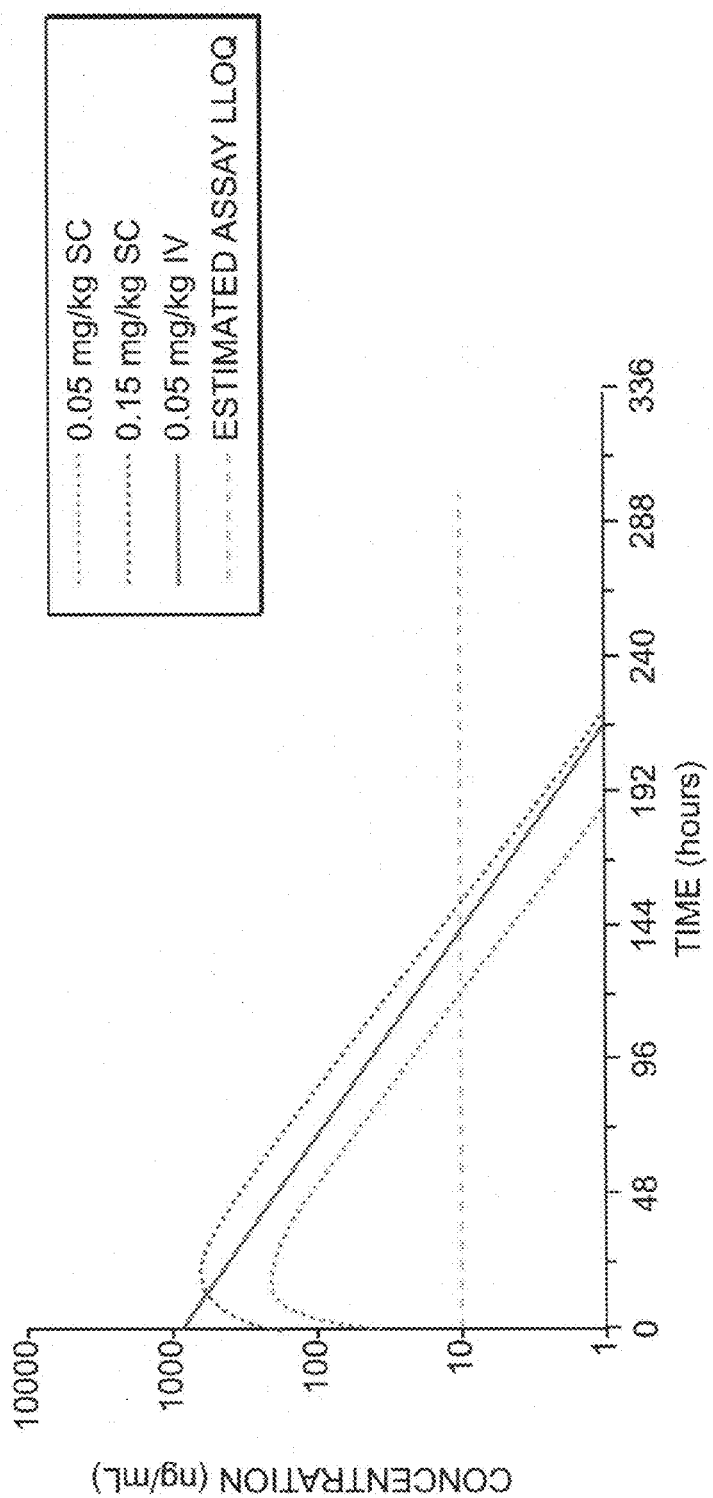
FIG. 7 shows the pharmacokinetics of Albulin (IN101NHY) in mice after subcutaneous dosing.
Figure 8:
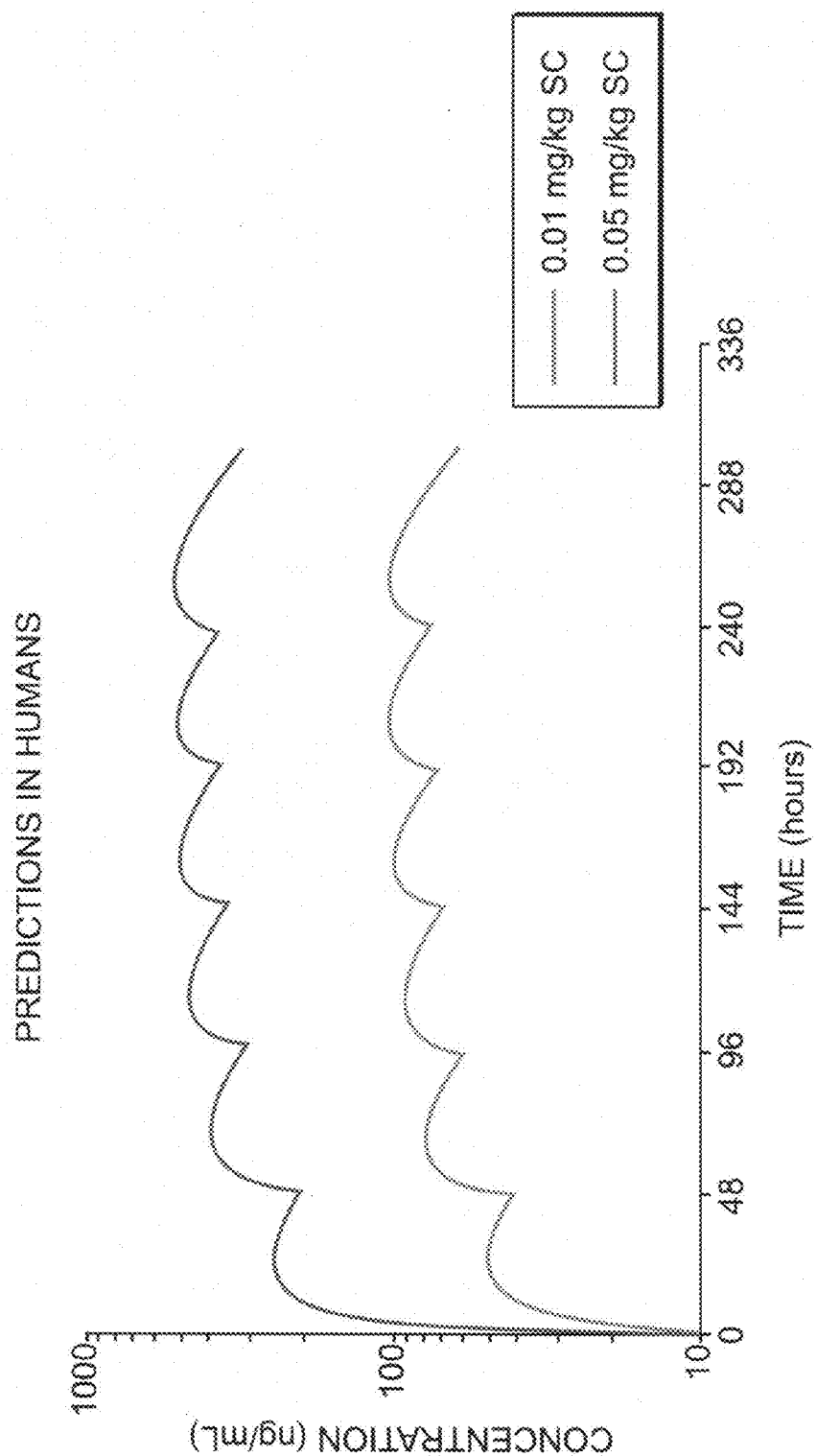
FIG. 8 shows the predicted pharmacokinetics of Albulin (IN101NHY) in a human after a 48 hour subcutaneous dosing.

The pharmacokinetics of Albulin (IN100NHY) was assessed in mice (FIG. 7). The half-life of Albulin in mice was observed to be ~6 hours. The predicted pharmacokinetic profile for Albulin (IN100NHY) in a human was modeled based on a 48 hour dosing (FIG. 8). A low peak/trough ratio of plasma level of Albulin (IN100NHY) may be achieved with this dosing interval. By about 10 days after the start of dosing, a steady-state level is achieved. No additional accumulation of drug should be observed.

Example 30

Figure 9A:
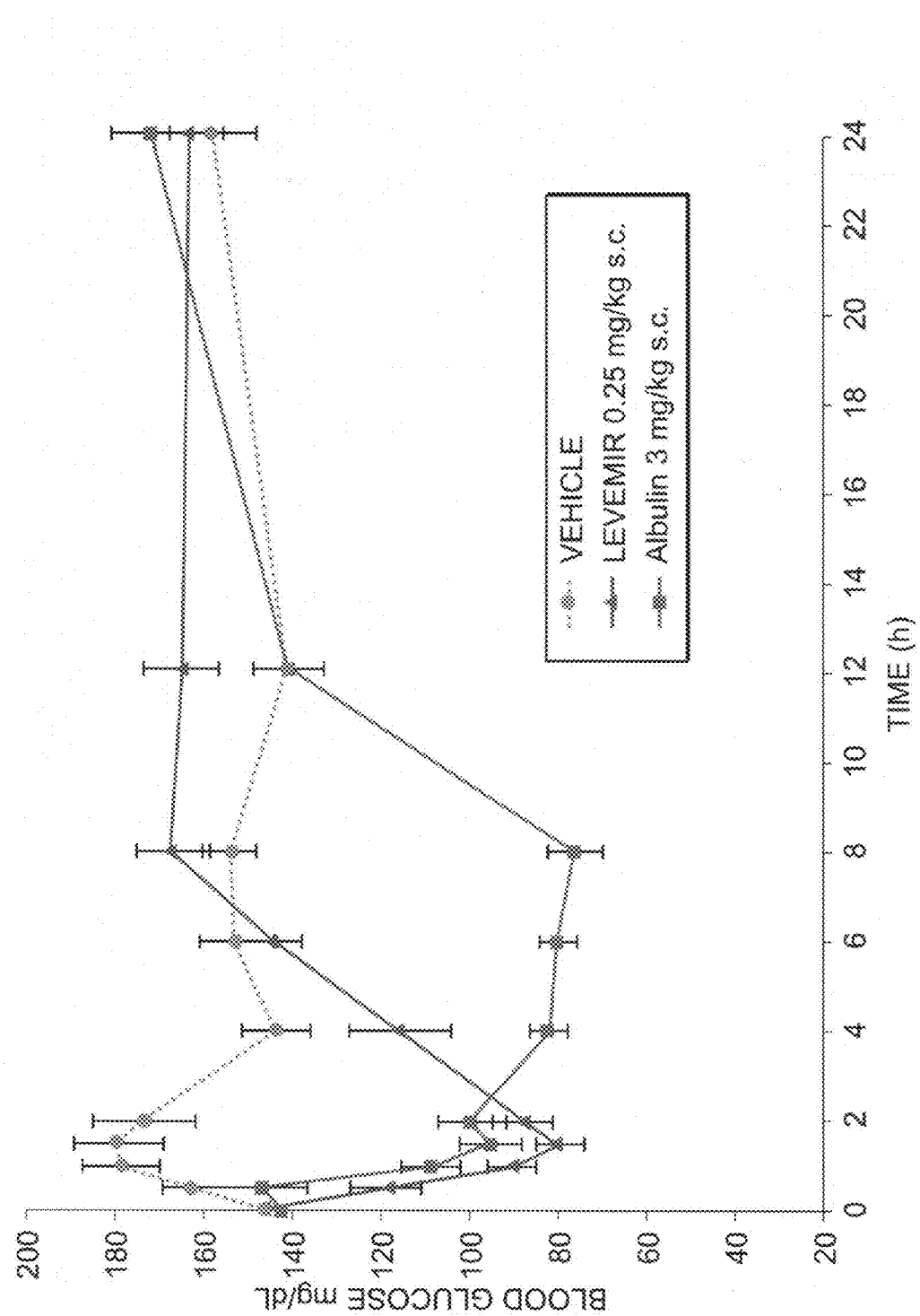
FIG. 9 shows a comparison of equimolar doses of Albulin (IN101NHY) and Levemir on blood glucose in mice.
Figure 9B:
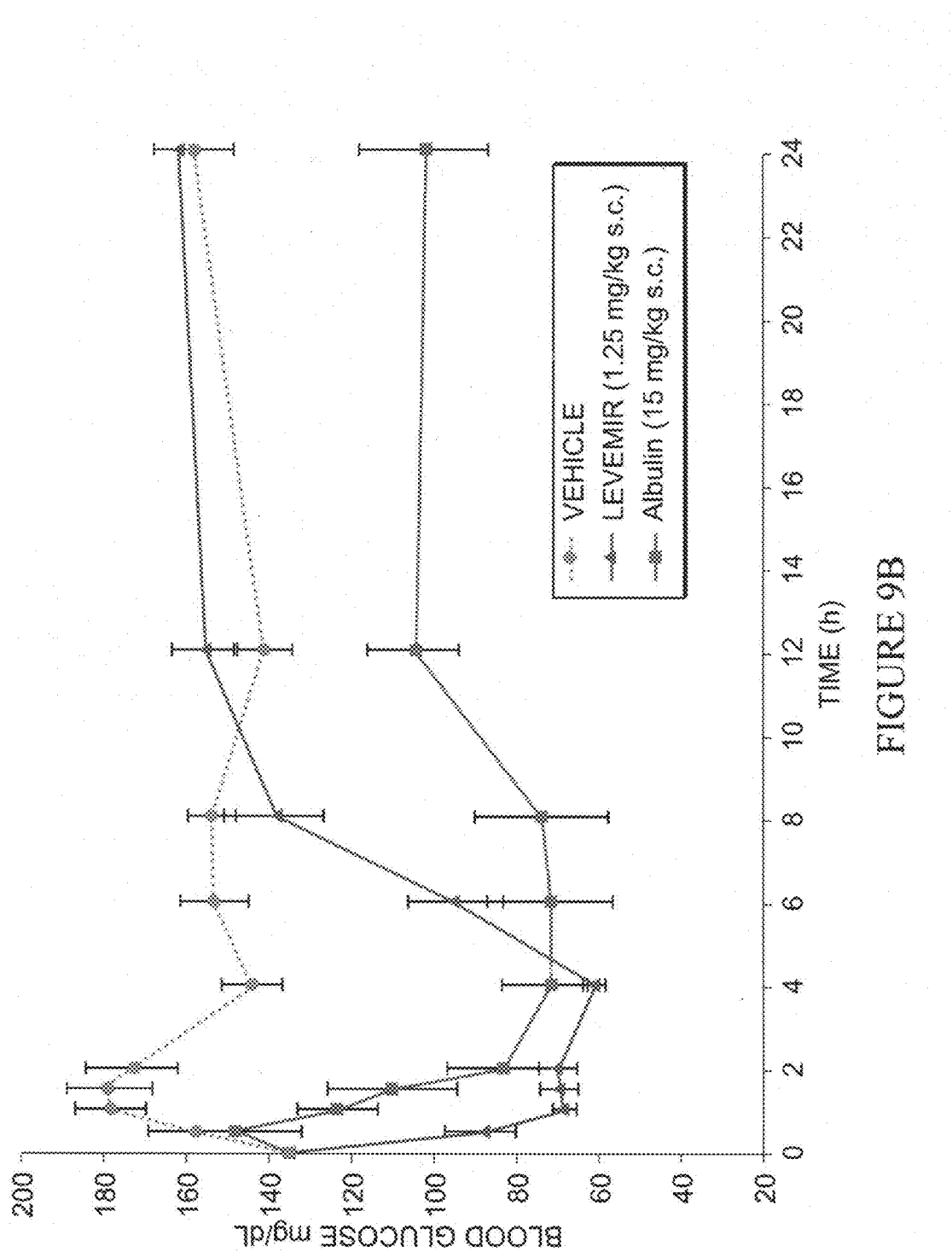

The pharmacodynamics of Albulin (IN100NHY) were compared with Levemir in normal mice. Equimolar amounts of Levemir or Albulin (IN100NHY) were administered subcutaneously (0.25 mg/kg Levemir versus 3 mg/kg Albulin (IN100NHY) or 1.25 mg/kg Levemir versus 15 mg/kg Albulin (IN100NHY)). A long-lasting effect of Albulin (IN100NHY) was observed (FIG. 9). A single subcutaneous dose of Albulin (IN100NHY) reduced blood sugar by ~1 hour and this effect lasted 8-12 hours, whereas an equimolar subcutaneous dose of Levemir caused a sharper drop and quicker rebound in blood sugar. The maximum reduction in blood sugar observed with equimolar doses of Albulin (IN100NHY) and Levemir was approximately the same, but the observed effect of Albulin (IN100NHY) lasted ~3× longer.

Example 31

The pharmacokinetics and pharmacodynamics of Albulin-G following pulmonary insufflation and intravenous dosing in rats were determined.

The purpose of this study was to characterize the pharmacokinetics and pharmacodynamic activity of Albulin-G following intravenous dosing and pulmonary insufflation in Sprague Dawley rats.

TABLE 3

Comparison of mitogenic activity for insulin, IGF-1, and insulin analogs

| Protein | L6 cells | | Saos cells | | HepG2 | |
|---|---|---|---|---|---|---|
| | EC50 (nM) | Percent mitogenic activity | EC50 (nM) | Percent mitogenic activity | EC50 (nM) | Percent mitogenic activity |
| Insulin | 3.66 | 100 | 2.7 | 100 | 7.78 | 100 |
| Albulin (GGGPGKR C-peptide) (SEQ ID NO: 29) | 26.59 | 13.76 | 19.86 | 13.59 | 88.73 | 9 |
| IGF-1 | 0.07 | 5228 | 0.17 | 1588 | 1.17 | 664 |
| Glargine | 4.73 | 77 | 2.36 | 114 | 1.86 | 418 |
| Levemir | 14.8 | 24.72 | 19.82 | 13.62 | 14.21 | 55 |
| Albulin (IGF-1 C-peptide) | 1.21 | 302 | 1.26 | 223 | 13.27 | 59 |

Albulin (IN100NHY) was observed to be ~5-10-fold less mitogenic than native insulin and less mitogenic than other FDA-approved insulin analogs including Glargine and Levemir. The C-peptide region of Albulin (IN100NHY) was observed to influence its reduced mitogenic activity. Albulin (IN101NHY), having the C-peptide from IGF-I between the A and B chains of insulin, exhibited increased mitogenic activity relative to insulin (i.e., ~3-fold higher on some cell types) and Albulin (IN100NHY) (i.e., as much as 20-fold higher on some cell types).

Albulin-G is a modified form of human insulin genetically fused at its C-terminus to the N-terminus of recombinant human serum albumin (HSA). See Table C, Insulin-HSA variants evaluated, supra, CID No. 2278, Name=IN100NHY1, C-peptide sequence=GGGPGKR (SEQ ID NO:29), and leader peptide=HAS-RKex2. This experiment was conducted as a preliminary evaluation of the pharmacokinetic and pharmacodynamic activity of Albulin-G following intravenous dosing and pulmonary insufflation in Sprague Dawley rats. The rat was chosen for this study because it is a species routinely selected for standard pharmacologic evaluation and is pharmacologically responsive to Albulin-G.

The study design is summarized here. Groups of 3-5 rats received a single dose of Albulin-G by either the intravenous route or by pulmonary insufflation (Technosphere formulation). Serum concentration time profiles were followed to evaluate pharmacokinetics. Serum blood glucose profiles were followed to evaluate pharmacodynamic activity. The experimental design is summarized in Table 4, below.

TABLE 4

Experiment Design

| Group | Dose level | Route | Albulin dose (mg/kg) (actual) | Sampling times (h) |
|---|---|---|---|---|
| 1 | 0.0 | IS | 0 | 0, 0.0833, 0.5, 1, 2, 4, 8, 12, 24, 36, 48 |
| 2 | 1 mg/kg | IV | 1 | |
| 3 and 7 | 3 mg/kg | IV | 3 | |
| 4 | 3 mg 15% load* | IS | 2.1-2.5 | |
| 5$^a$ | 3 mg 30% load* | IS | 1.08-5.76 | |
| 6 | 3 mg 15% load* | IS | 2.03-2.34 | |

Albulin-G was formulated with Technosphere for pulmonary insufflation (IS); dose level indicates the weight of the powder prior to insufflation and the % of the weight estimated as Albulin-G Blood samples were collected to determine the serum Albulin-G concentrations for PK (pharmacokinetics) analysis. Blood samples were collected at the following times: 0.083, 0.5, 1, 2, 4, 8, 12, 18, 24, 36 and 48 hours after dosing.

ELISA protocol: Serum Albulin-G concentrations were determined using a sandwich ELISA with an insulin capture antibody and a human serum albumin antibody as the detector. The assay is specific for Albulin-G and does not cross react with insulin.

Pharmacokinetic parameters were calculated using non-compartmental methods and the nonlinear regression program WinNonlin (Version 5.0.1). An extravascular dosing model was used for the evaluation of the IS dosing, and a IV (intravenous) data were fit with a 1-compartment model assuming bolus input, and a weighting of $1/p^2$ (where p is the predicted value for the observation).

Results

Pharmacokinetics: Mean serum concentration time profiles are presented in FIG. 10. For all animals, the actual administered dose on a mg/kg basis was used in the pharmacokinetic analyses. Mean pharmacokinetic parameters are presented in Table 5 for the IV (intravenous) groups and Table 6 for the IS (pulmonary insufflation) groups.

TABLE 5

Mean (±SD) pharmacokinetic parameters following IV dosing with Albulin-G

| Group No. | | $T_{1/2}$ (h) | $C_{max}$ (ng/mL) | Cl (mL/h/kg) | Vss (mL/kg) | Vz (mL/kg) | $AUC_{0-\infty}$/D (h*kg)/mL | $C_{max}$/D (kg/mL) | $AUC_{0-\infty}$ (ng*h/mL) |
|---|---|---|---|---|---|---|---|---|---|
| 2 | Mean | 5.6 | 35119.2 | 5.9 | 32.2 | 48.5 | 0.171 | 0.035 | 170994.2 |
| N = 3 | SD | 0.5 | 7430.9 | 0.1 | 1.6 | 4.2 | 0.004 | 0.007 | 3722.8 |
| 3 and 7 | Mean | 5.6 | 86942.1 | 7.6 | 67.6 | 61.1 | 0.132 | 0.029 | 394829.4 |
| N = 6$^A$ | SD | NC | 36169.3 | NC | NC | NC | NC | 0.012 | NC |

$^A$Only 1 animal survived to provide samples for determination of terminal phase parameters.

$C_{max}$ = Maximum serum concentration; Cl = clearance; Vss = An estimate of the volume of distribution at steady-state; Vz = volume of distribution; $AUC_{0-\infty}$ = Area under the serum concentration curve from zero time to infinite time.

All rats in groups 4-6 received a nominal 3 mg dose of technospheres loaded with Albulin-G by pulmonary insufflation. The amount of Albulin-G loaded on the spheres varied between 15 and 30% depending on the dose group. Actual dose administered on a mg/kg basis was calculated as:

$$[(Wt_{filled\ chamber\ prior\ to\ dosing} - Wt_{chamber\ after\ dosing}) \times \%\ load] \div BWT\ (kg)$$

TABLE 6

Mean (±SD) pharmacokinetic parameters following insufflation with Albulin-G

| Group No. | | $T_{1/2}$ (h) | $C_{max}$ (ng/mL) | $T_{max}$ (h) | Cl/F (mL/h/kg) | Vz/F (mL/kg) | $AUC_{0-\infty}$ (ng*h/mL) | $C_{max}$/Dose (kg/mL) | $AUC_{0-\infty}$/dose (h*kg)/mL | MRT (h) |
|---|---|---|---|---|---|---|---|---|---|---|
| 4 | Mean | 11.0 | 2157.2 | 2.8 | 100.3 | 1626.2 | 25475.2 | 0.0009 | 0.0111 | 13.0 |
| N = 5 | SD | 1.7 | 585.1 | 1.1 | 41.0 | 747.6 | 7010.9 | 0.0003 | 0.0037 | 1.6 |
| 5$^a$ | Mean | 13.8 | 5571.2 | 2.5 | 76.4 | 1481.9 | 62213.7 | 0.0012 | 0.0133 | 12.6 |
| N = 4 | SD | 4.6 | 928.1 | 1.0 | 11.6 | 378.9 | 15260.5 | 0.0000 | 0.0020 | 3.4 |
| 6 | Mean | 8.8 | 3036.9 | 2.4 | 71.1 | 921.5 | 33951.0 | 0.0014 | 0.0154 | 9.8 |
| N = 5 | SD | 1.0 | 627.7 | 0.9 | 24.3 | 373.5 | 10294.1 | 0.0003 | 0.0051 | 1.1 |

$^a$Animal 20, received an estimated dose of 1.08 mg/kg. PK from the animal was analyzed, but was not included in the calculation of means and SD for the dose group.

Cl/F = Apparent clearance following extravascular administration; Vz/F = apparent volume of distribution, where F = bioavailability; MRT = Mean residence time.

Following pulmonary insufflation, Albulin-G was absorbed rapidly with peak serum concentrations occurring an average of 2.4 to 2.8 hours after dosing. Clearance (CL/F) ranged between 71 and 100 mL/h/kg. The mean elimination half-life ranged between 9 and 14 hours. The volume of distribution was large (averaging 922 to 1626 mL/kg).

Figure 10:
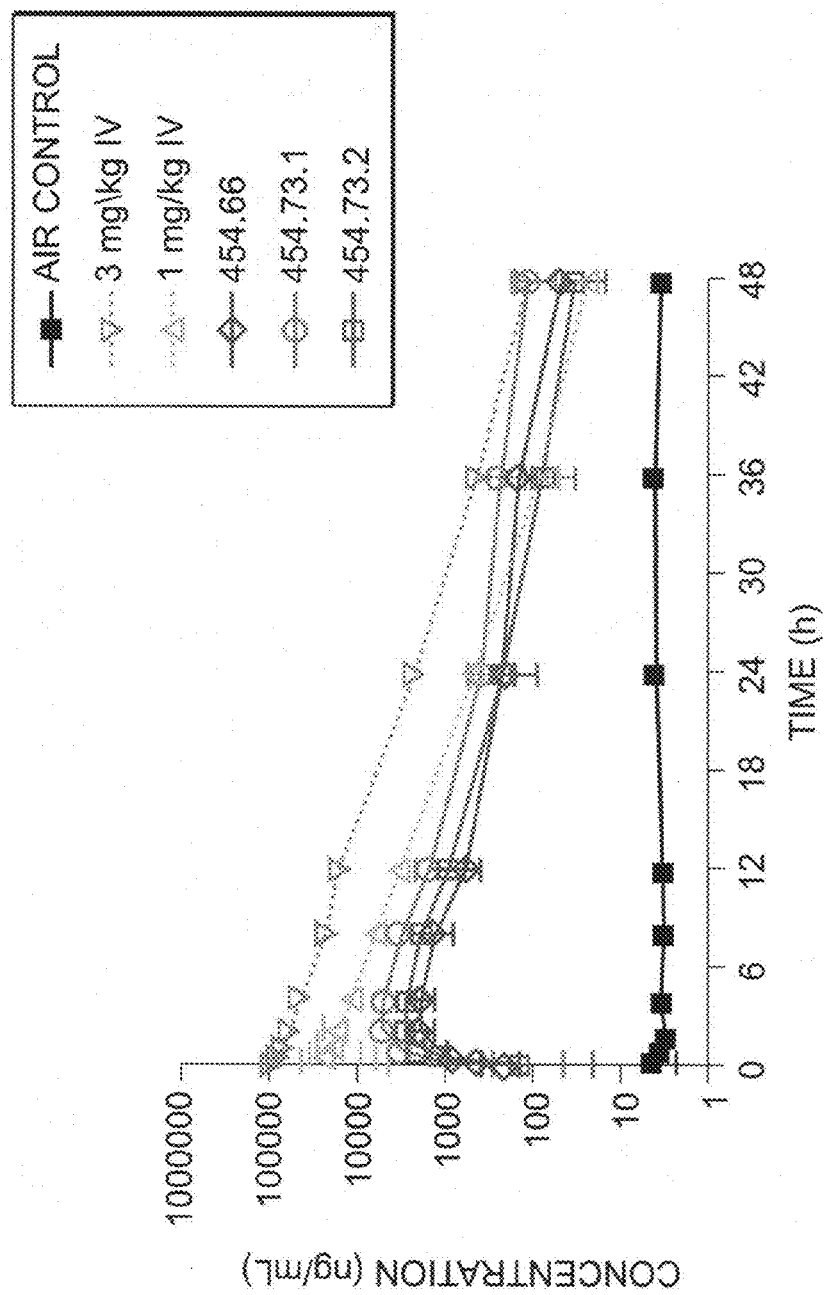
FIG. 10 shows mean±SD serum concentrations following dosing with Albulin-G by the intravenous (IV) or insufflation route.

A dose of 3 mg/kg IV was not tolerated in fasted rats. Five of 6 animals died within 8 hours of dosing. One animal survived with glucose intervention. The profile presented in FIG. 10 is that of the single surviving animal at all points after 8 hours. All 3 rats survived a single IV dose of 1 mg/kg. Examination of the individual animal profiles following IV injection show that the dose was at least partially extravascular in animal number 8 (1 mg/kg). Pharmacokinetic parameters were calculated in this animal, but the data were excluded from the calculation of mean pharmacokinetic parameters. The mean elimination half-life was 5.6 hours following IV injection based on data obtained from 1 animal in the 3 mg/kg dose group and 2 rats in the 1 mg/kg dose group. The clearance of Albulin-G was 5.9 to 7.6 ml/h/kg. The volume of distribution was 48.5 to 61.1 ml/kg. This exceeds the estimated plasma volume but is less than the extracellular volume.

Bioavailability: There were 3 animals in the IV dose groups with sufficient terminal phase serum concentration data to calculate $AUC_{0-\infty}$. These animals were at 2 different dose levels. Therefore, the bioavailability after insufflation was estimated as:

$$\frac{\text{Mean } AUC_{0-\infty}/\text{dose following insufflation at each dose level}}{\text{Mean } AUC_{0-\infty}/\text{dose following intravenous injection all dose levels}}$$

Figure 17:
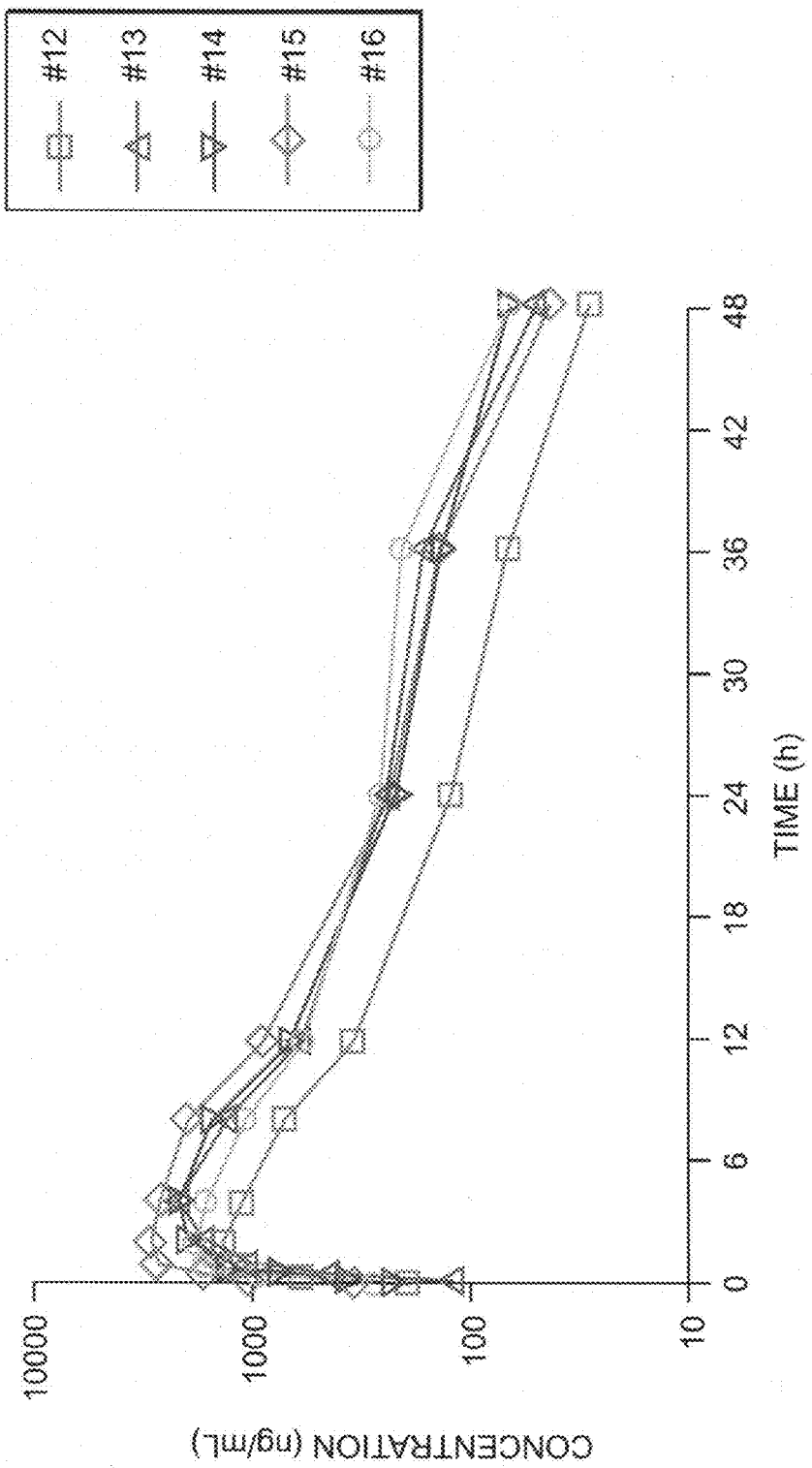
FIG. 17 shows serum albulin concentration time curves following a single IS dose of 3 mg (454/66).
Figure 19:
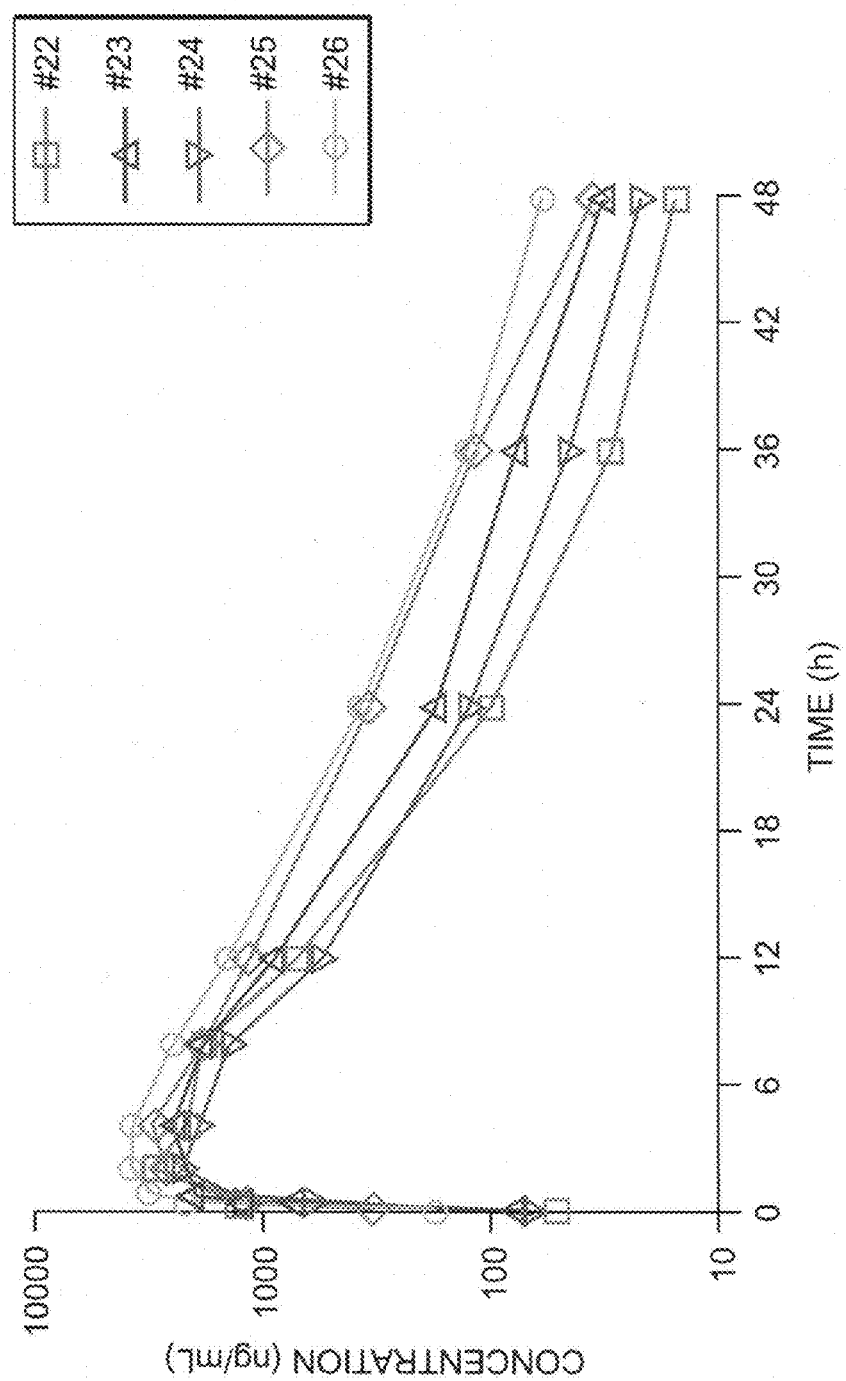
FIG. 19 shows serum albulin concentration time curves following a single IS dose of 3 mg (454/73.2).

The bioavailability after insufflation was calculated separately for each dose group because of the different formulations and loads used. Results are presented in Table 7 below. The $AUC_{0-\infty}$/dose was calculated for each animal and normalized to the dose administered to that individual animal prior to the bioavailability calculation. FIG. 15 shows serum albulin concentration time curves following a single IV dose of 1 mg/kg; FIG. 16 shows serum albulin concentration time curves following a single IV dose of 3 mg/kg; FIG. 17 shows serum albulin concentration time curves following a single IS dose of 3 mg (454/66); FIG. 18 shows serum albulin concentration time curves following a single IS dose of 3 mg (454/73.1); and FIG. 19 shows serum albulin concentration time curves following a single IS dose of 3 mg (454/73.2).

TABLE 7

| Bioavailability estimate following pulmonary insufflation | | | |
|---|---|---|---|
| Mean $AUC_{0-\infty}$/dose | Mean $AUC_{0-\infty}$/dose | Mean $AUC_{0-\infty}$/dose | Mean $AUC_{0-\infty}$/dose |
| IV | 454.66 | 454.73.1 | 454.73.2 |
| 0.1579 | 0.0111 | 0.0130 | 0.0154 |
| F % | 7.0 | 8.2 | 9.8 |

Bioavailability was 7% in Group 4, 8.2% in Group 5 and 9.8% in Group 6.

Pharmacodynamic analyses: Pharmacokinetic/pharmacodynamic analyses were conducted to explore the relationship between Albulin-G exposure and blood glucose concentrations. The following specific questions were addressed:

1) Does a higher $C_{max}$ of Albulin-G predict a greater percent decrease in blood glucose (a greater $E_{max}$)?
2) Does a larger $AUC_{0-\infty}$ for Albulin-G predict a greater $E_{max}$?
3) Does a higher $C_{max}$ of Albulin-G predict a larger AUC for effect (the decrease in serum glucose time concentration curve attributable to Albulin-G (AUEC)?
4) Does a larger $AUC_{0-8h}$ of Albulin-G predict a larger AUEC?

The percent decrease in blood glucose was calculated by the following formula:

$$[(\text{Glucose}_{(time)}-\text{Glucose}_{(predose)})/\text{Glucose}_{(predose)}]*100$$

Figure 11:
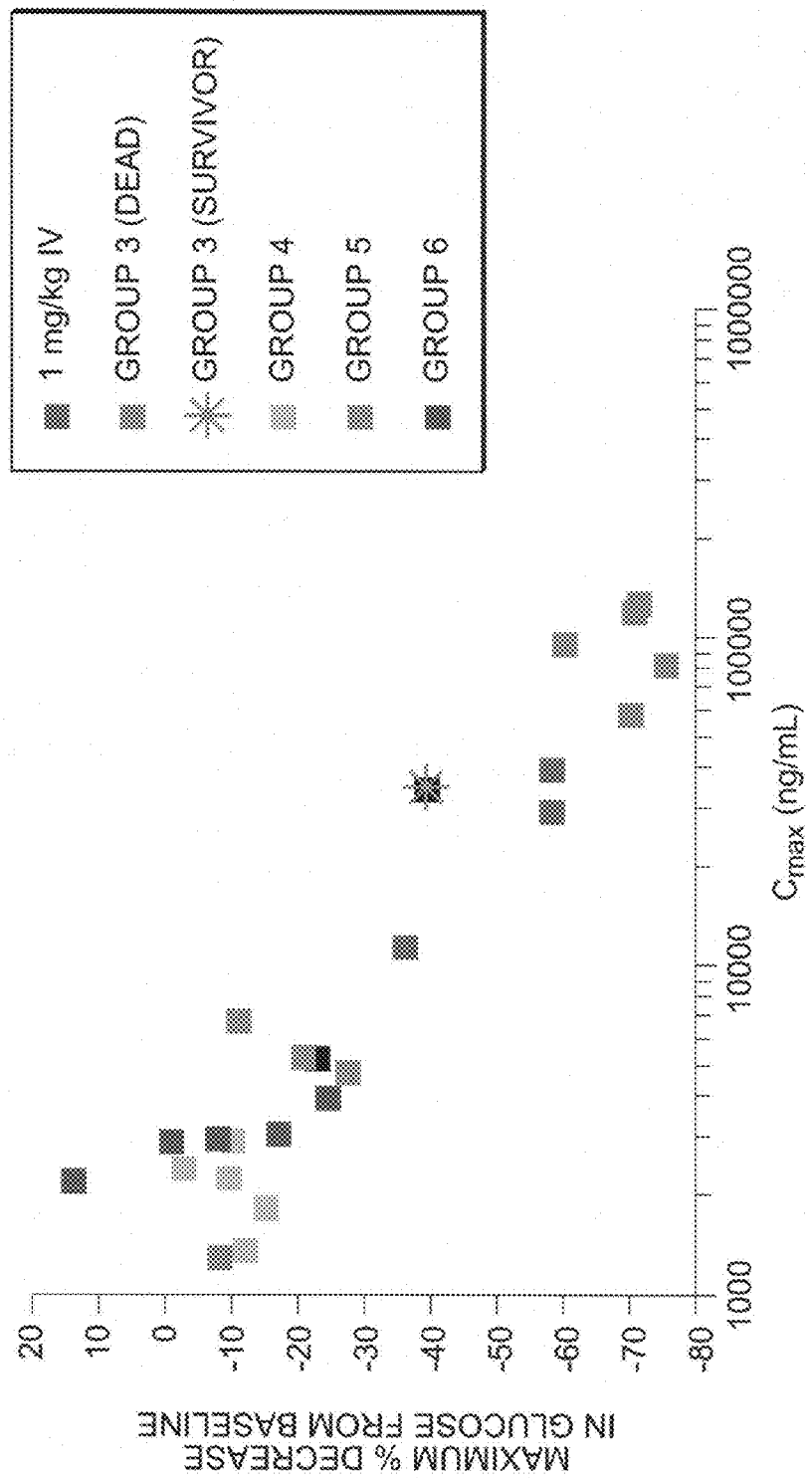
FIG. 11 shows maximum percent decrease in blood glucose versus maximum serum drug concentration of Albulin-G.

$C_{max}$ versus $E_{max}$ (percent change in blood glucose): The maximum percent drop in blood glucose for each animal was plotted versus the Albulin-G $C_{max}$ achieved in each animal. The IV and insufflation dose groups were combined for this analysis. Results are presented in FIG. 11. Since the sample size is small a nonparametric analysis (Spearman) was conducted to evaluate the degree of correlation between $C_{max}$ and $E_{max}$. A higher $C_{max}$ correlated with a larger decline in serum glucose concentration. The correlation coefficient is −0.8748 or an $r^2$ of 0.7650.

Figure 12:
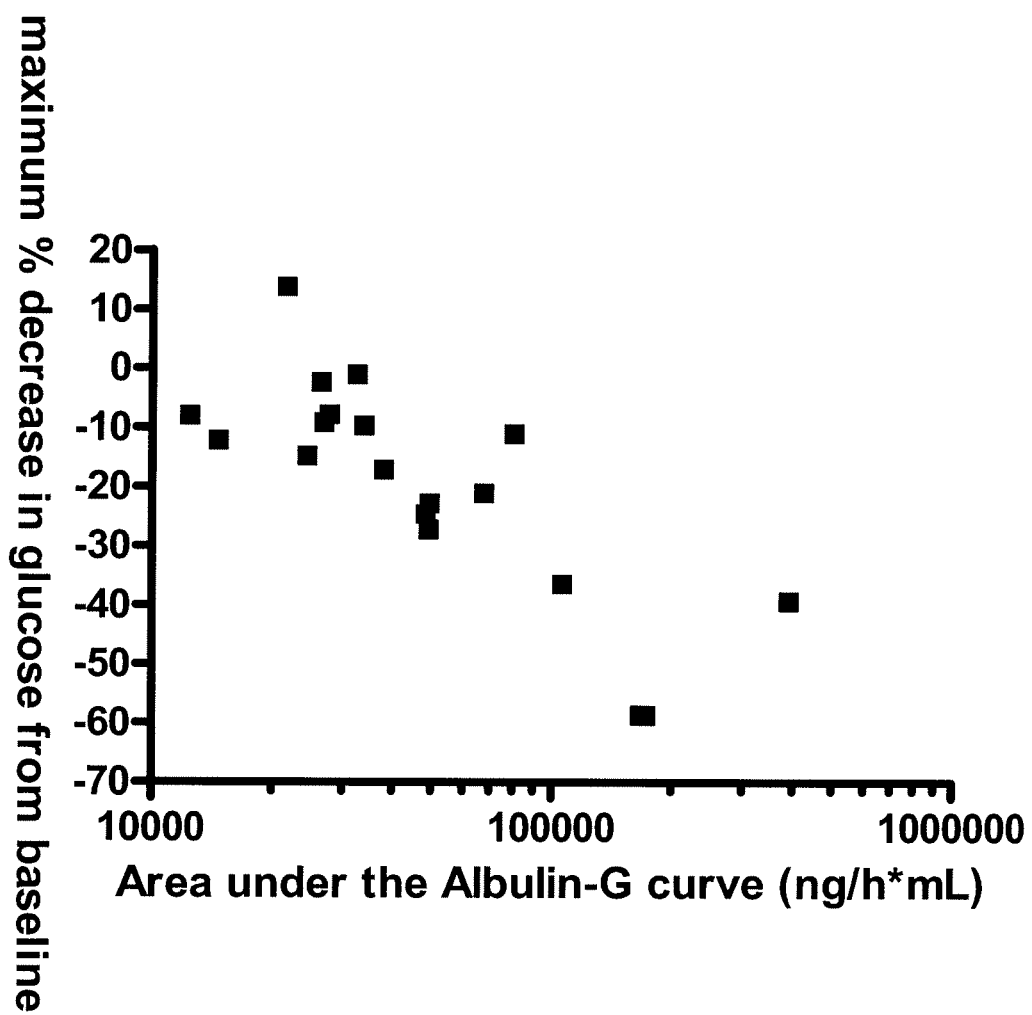
FIG. 12 shows maximum percent decrease in blood glucose versus Albulin-G AUC0-∞.

AUC versus $E_{max}$: $AUC_{0-\infty}$ for Albulin-G was compared with maximal change in blood glucose. See e.g., FIG. 12, which shows the maximum percent decrease in blood glucose versus Albulin-G AUC0-∞. There are fewer data points for this analysis because it was not possible to calculate AUC 0-∞ for animals that did not survive the study. The loss of these animals biases the analysis because it would be expected that they would be largest AUCs in the study. This eliminates the lower portion of the curve. A higher AUC does correlate with a greater $E_{max}$. The correlation coefficient is −0.7930 for an $r^2$ of 0.6288.

Figure 13:
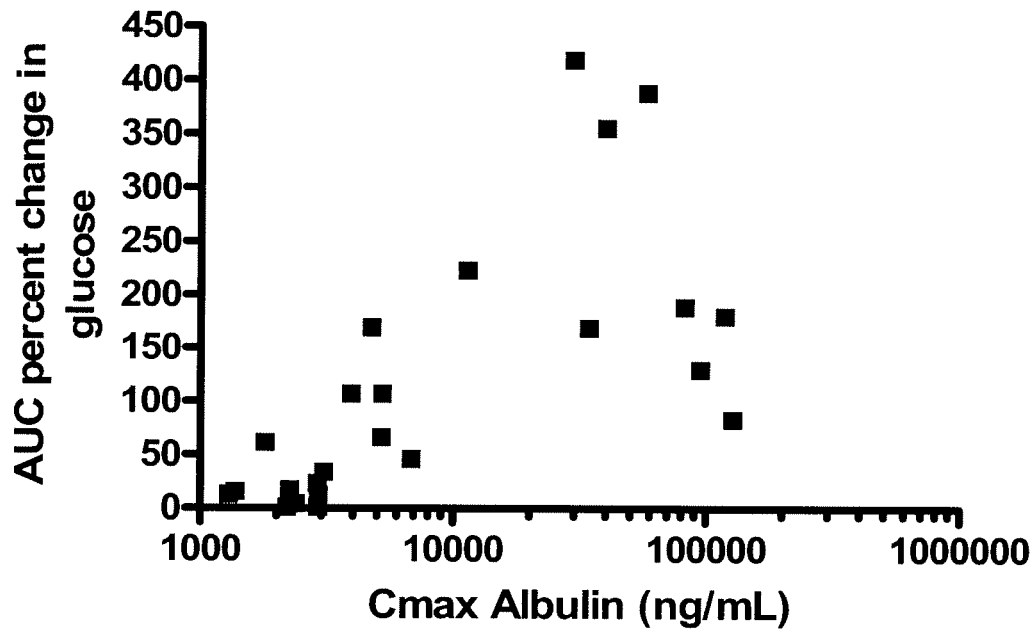
FIG. 13 shows Albulin-G $C_{max}$ versus the AUEC for serum glucose.

$C_{max}$ versus AUEC: These analyses explore whether the total decrease in blood glucose over time (AUEC) correlates with the $C_{max}$ or AUC for Albulin-G. To calculate AUEC, blood glucose data were first converted to percent change from baseline and then the AUC from 0 to 8 hours was calculated. The serum glucose data obtained after 8 hours were not used in the analysis because food had been returned to the animals. The results of this analysis are plotted in FIG. 13, which shows Albulin-G $C_{max}$ versus AUEC for serum glucose. A higher $C_{max}$ for Albulin-G correlated with a larger AUEC (Spearman's coefficient 0.7713 or an $r^2$ of 0.5942).

Figure 14:
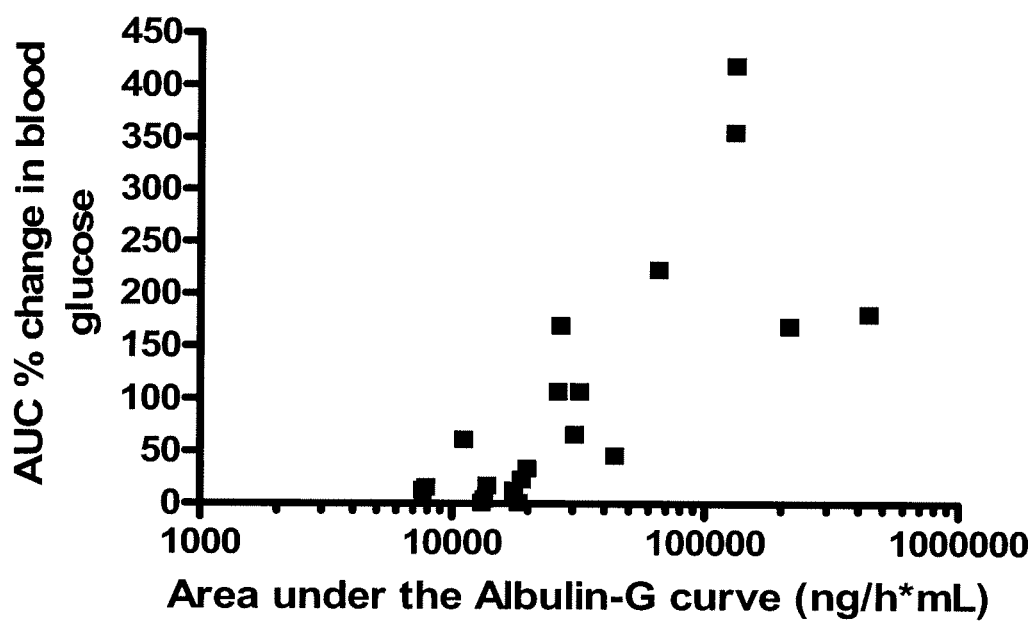
FIG. 14 shows AUC Albulin-G versus AUEC for serum glucose.

AUC Albulin versus AUEC: The final analysis was to evaluate whether greater exposure (as measured by AUC) of Albulin correlated with increased AUECglucose. Results are presented in FIG. 14, which shows AUC Albulin-G versus AUEC for serum glucose. A higher AUC for Albulin-G correlated with a greater AUECglucose greater AUEC (Spearman's coefficient 0.8150 or an $r^2$ of 0.6642).

Table 8 shows the serum concentrations following Albulin G dosing, Tables 9 and 10 shows the PK parameters by individual animal, and Table 11 shows the doses administered.

TABLE 8

Serum Albulin concentrations following dosing with Albulin by the intravenous or insufflation route.

| Group | Animal ID | 0 | 0.08 h | 0.5 h | 1 h | 2 h | 4 h | 8 h | 12 h | 24 h | 36 h | 48 h |
|---|---|---|---|---|---|---|---|---|---|---|---|---|
| Group 1 | # 1 | <LLOQ | 7 | <LLOQ | <LLOQ | <LLOQ | <LLOQ | <LLOQ | <LLOQ | <LLOQ | <LLOQ | <LLOQ |
| Control | # 2 | <LLOQ | <LLOQ | <LLOQ | <LLOQ | <LLOQ | <LLOQ | <LLOQ | <LLOQ | <LLOQ | <LLOQ | <LLOQ |
| | # 3 | <LLOQ | <LLOQ | <LLOQ | <LLOQ | <LLOQ | <LLOQ | <LLOQ | <LLOQ | <LLOQ | <LLOQ | <LLOQ |
| | # 4 | <LLOQ | <LLOQ | <LLOQ | <LLOQ | <LLOQ | <LLOQ | <LLOQ | <LLOQ | <LLOQ | <LLOQ | <LLOQ |
| | # 5 | <LLOQ | <LLOQ | <LLOQ | <LLOQ | <LLOQ | <LLOQ | <LLOQ | <LLOQ | <LLOQ | <LLOQ | <LLOQ |
| Group 2 | # 6 | <LLOQ | 29865 | 26689 | 23704 | 24003 | 15008 | 7587 | 3234 | 456 | 90 | 31 |
| 1 mg/kg IV | # 7 | <LLOQ | 40374 | 32708 | 28024 | 22700 | 13140 | 6694 | 2986 | 380 | 59 | 17 |
| | # 8 | <LLOQ | 2638 | 4673 | 8229 | 11523 | 9612 | 5711 | 3213 | 641 | 121 | 29 |
| Group 3 | # 9 | <LLOQ | 33364 | 45743 | 51908 | 58505 | 45738 | NS | NS | NS | NS | NS |
| and 7 | # 10 | <LLOQ | 129282 | 107380 | 93983 | 73398 | 56175 | NS | NS | NS | NS | NS |
| 3 mg/kg IV | # 11 | <LLOQ | 120035 | 95153 | 89748 | 71464 | 50652 | 25195 | NS | NS | NS | NS |
| | # 27 | <LLOQ | 96149 | 89425 | 76697 | 62610 | 49606 | NS | NS | NS | NS | NS |
| | # 28 | <LLOQ | 34546 | 31401 | 31339 | 29324 | 27739 | 20989 | 16084 | 2421 | 447 | 122 |
| | # 29 | <LLOQ | 83136 | 76666 | 73958 | 69677 | 46400 | NS | NS | NS | NS | NS |
| Group 4 | # 12 | <LLOQ | 194 | 573 | 1221 | 1384 | 1109 | 701 | 341 | 127 | 69 | 30 |
| 3 mg | # 13 | <LLOQ | 125 | 497 | 1159 | 1869 | 2391 | 1329 | 638 | 245 | 169 | 51 |
| 15% load | # 14 | <LLOQ | 217 | 729 | 1452 | 1886 | 2272 | 1440 | 651 | 222 | 135 | 64 |
| 466 | # 15 | <LLOQ | 355 | 1682 | 2761 | 2924 | 2612 | 1977 | 904 | 231 | 143 | 45 |
| | # 16 | 6 | 272 | 926 | 1627 | 1815 | 1586 | 1061 | 587 | 263 | 207 | 66 |
| Group 5 | # 17 | 15 | 74 | 1438 | 3259 | 5263 | 4837 | 2802 | 1469 | 205 | 102 | 41 |
| 3 mg | # 18 | <LLOQ | 136 | 1915 | 3118 | 4802 | 4043 | 2409 | 1094 | 325 | 287 | 110 |
| 30% load | # 19 | <LLOQ | 132 | 1913 | 2827 | 5058 | 5299 | 3059 | 1912 | 484 | 329 | 206 |
| 454.73.1 | # 20 | <LLOQ | 39 | 586 | 1165 | 1307 | 1193 | 585 | 307 | 71 | 33 | 15 |
| | # 21 | <LLOQ | 367 | 3013 | 5219 | 6921 | 6783 | 4306 | 2305 | 600 | 267 | 111 |
| Group 6 | # 22 | <LLOQ | 52 | 1314 | 2603 | 2958 | 2285 | 1981 | 761 | 102 | 30 | 15 |
| 3 mg | # 23 | <LLOQ | 83 | 817 | 2081 | 2936 | 2659 | 2112 | 972 | 188 | 81 | 35 |
| 15% load | # 24 | <LLOQ | 64 | 588 | 1637 | 2218 | 1931 | 1362 | 546 | 123 | 44 | 21 |
| 454.73.2 | # 25 | <LLOQ | 346 | 1248 | 2768 | 2807 | 3095 | 1959 | 1197 | 360 | 118 | 37 |
| | # 26 | <LLOQ | 182 | 2333 | 3318 | 3978 | 3953 | 2607 | 1472 | 388 | 128 | 59 |

NS—no sample available
<LLOQ - below the 4.11 ng/mL lower limit of quantitation

TABLE 9

PK parameters by individual animal; Calculated pharmacokinetic parameters following dosing with Albulin by insufflation

| Group No. | Animal ID | $T_{1/2}$ (h) | $C_{max}$ (ng/mL) | $T_{max}$ (h) | Cl/F (mL/h/kg) | Vz/F (mL/kg) | $AUC_{0-\infty}$ (ng*h/mL) | $C_{max}$/Dose (kg/mL) | $AUC_{0-\infty}$/dose (h*kg)/mL | MRT (h) |
|---|---|---|---|---|---|---|---|---|---|---|
| Group 4 | # 12 | 11.46 | 1384.29 | 2.00 | 169.55 | 2804.07 | 14745.18 | 0.0006 | 0.0059 | 12.38 |
| | # 13 | 10.44 | 2391.18 | 4.00 | 85.17 | 1282.92 | 26651.38 | 0.0011 | 0.0117 | 13.06 |
| | # 14 | 13.42 | 2271.53 | 4.00 | 87.37 | 1692.07 | 27126.97 | 0.0010 | 0.0114 | 13.70 |
| | # 15 | 8.76 | 2923.59 | 2.00 | 61.35 | 775.66 | 34229.73 | 0.0014 | 0.0163 | 10.77 |
| | # 16 | 11.12 | 1815.27 | 2.00 | 98.28 | 1576.13 | 24622.74 | 0.0008 | 0.0102 | 15.03 |
| | N | 5 | 5 | 5 | 5 | 5 | 5 | 5 | 5 | 5 |
| | Mean | 11.042 | 2157.170 | 2.800 | 100.344 | 1626.170 | 25475.202 | 0.0009 | 0.0111 | 12.988 |
| | SD | 1.689 | 585.122 | 1.095 | 40.964 | 747.577 | 7010.948 | 0.0003 | 0.0037 | 1.579 |
| Group 5[a] | # 17 | 10.34 | 5262.77 | 2.00 | 89.75 | 1339.50 | 49914.52 | 0.0012 | 0.0111 | 9.09 |
| | # 18 | 15.32 | 4801.50 | 2.00 | 81.33 | 1797.49 | 49673.77 | 0.0012 | 0.0123 | 13.50 |
| | # 19 | 19.49 | 5299.30 | 4.00 | 63.30 | 1780.06 | 68243.97 | 0.0012 | 0.0158 | 16.90 |
| | # 21 | 9.85 | 6921.31 | 2.00 | 71.09 | 1010.73 | 81022.43 | 0.0012 | 0.0141 | 10.98 |
| | N | 4 | 4 | 4 | 4 | 4 | 4 | 4 | 4 | 4 |
| | Mean | 13.752 | 5571.221 | 2.500 | 76.369 | 1481.943 | 62213.671 | 0.0012 | 0.0133 | 12.619 |
| | SD | 4.553 | 928.135 | 1.000 | 11.581 | 378.934 | 15260.539 | 0.0000 | 0.0020 | 3.377 |
| Group 6 | # 22 | 8.80 | 2957.61 | 2.00 | 79.72 | 1011.78 | 27972.68 | 0.0013 | 0.0125 | 8.12 |
| | # 23 | 9.81 | 2936.06 | 2.00 | 70.47 | 997.65 | 32781.80 | 0.0013 | 0.0142 | 10.09 |
| | # 24 | 9.46 | 2217.84 | 2.00 | 107.15 | 1463.00 | 21838.79 | 0.0009 | 0.0093 | 9.40 |
| | # 25 | 7.29 | 3094.98 | 4.00 | 52.93 | 556.45 | 38356.03 | 0.0015 | 0.0189 | 10.82 |
| | # 26 | 8.85 | 3977.91 | 2.00 | 45.28 | 578.47 | 48805.63 | 0.0018 | 0.0221 | 10.64 |
| | N | 5 | 5 | 5 | 5 | 5 | 5 | 5 | 5 | 5 |
| | Mean | 8.843 | 3036.881 | 2.400 | 71.108 | 921.470 | 33950.987 | 0.0014 | 0.0154 | 9.812 |
| | SD | 0.968 | 627.731 | 0.894 | 24.347 | 373.533 | 10294.141 | 0.0003 | 0.0051 | 1.098 |

[a]Animal 20 from this group was misdosed and the results from this animal are excluded from the mean calculations.

TABLE 10

Calculated pharmacokinetic parameters following dosing with Albulin by intravenous injection

| Group No. | Animal ID | $T_{1/2}$ (h) | $C_{max}$ (ng/mL) | Cl (mL/h/kg) | Vss (mL/kg) | Vz (mL/kg) | $AUC_{0-\infty}$/dose (h*kg)/mL | $C_{max}$/Dose (kg/mL) | $AUC_{0-\infty}$ (ng*h/mL) |
|---|---|---|---|---|---|---|---|---|---|
| Group 2 | # 6 | 6.19 | 29864.73 | 5.76 | 33.34 | 51.44 | 0.17 | 0.03 | 173626.63 |
|  | # 7 | 5.31 | 40373.64 | 5.94 | 31.05 | 45.53 | 0.17 | 0.04 | 168361.84 |
|  | # 8[b] | 5.39 | NC | NC | NC | NC | NC | NC | NC |
|  | N | 3 | 2 | 2 | 2 | 2 | 2 | 2 | 2 |
|  | Mean | 5.631 | 35119.186 | 5.850 | 32.196 | 48.488 | 0.171 | 0.035 | 170994.235 |
|  | SD | 0.487 | 7430.927 | 0.127 | 1.625 | 4.178 | 0.004 | 0.007 | 3722.768 |
| Groups 3 | # 9 | NC | 58505.15 | NC | NC | NC | NC | 0.02 | NC |
| and 7 | # 10 | NC | 129282.33 | NC | NC | NC | NC | 0.04 | NC |
|  | # 11 | NC | 120034.80 | NC | NC | NC | NC | 0.04 | NC |
|  | # 27 | NC | 96148.59 | NC | NC | NC | NC | 0.03 | NC |
|  | # 28 | 5.57 | 34545.89 | 7.60 | 67.62 | 61.10 | 0.13 | 0.01 | 394829.41 |
|  | # 29 | NC | 83136.09 | NC | NC | NC | NC | 0.03 | NC |
|  | N | 1 | 6 | 1 | 1 | 1 | 1 | 6 | 1 |
|  | Mean | 5.574 | 86942.142 | 7.598 | 67.620 | 61.105 | 0.132 | 0.029 | 394829.414 |
|  | SD | NC | 36169.296 | NC | NC | NC | NC | 0.012 | NC |

[b]Data from this animal was not included in most PK calculations since the serum concentration curve indicted that at least part of this dose was extravascular. There were sufficient points to estimate an elimination half-life, which appears to parallel that seen in other animals at this dose.
NC—not calculated

TABLE 11

Doses administered

| Animal ID | BWT | Administered amount (mg) | Dose (mg/kg) total administration | Dose (mg/kg) Albulin-G | group |
|---|---|---|---|---|---|
| 1 | 193.1 | 0 | 0.00 | 0.00 | 1 |
| 2 | 204.9 | 0 | 0.00 | 0.00 | 1 |
| 3 | 208.3 | 0 | 0.00 | 0.00 | 1 |
| 4 | 209.3 | 0 | 0.00 | 0.00 | 1 |
| 5 | 216.4 | 0 | 0.00 | 0.00 | 1 |
| 6 | 193.2 | 1 mg/kg | 1.00 | 1.00 | 2 |
| 7 | 198.9 | 1 mg/kg | 1.00 | 1.00 | 2 |
| 8 | 208.5 | 1 mg/kg | 1.00 | 1.00 | 2 |
| 9 | 194.4 | 3 mg/kg | 3.00 | 3.00 | 3 |
| 10 | 200.1 | 3 mg/kg | 3.00 | 3.00 | 3 |
| 11 | 206.2 | 3 mg/kg | 3.00 | 3.00 | 3 |
| 12 | 195.1 | 3.25 | 16.66 | 2.50 | 4 |
| 13 | 202 | 3.06 | 15.15 | 2.27 | 4 |
| 14 | 207 | 3.27 | 15.80 | 2.37 | 4 |
| 15 | 209.5 | 2.93 | 13.99 | 2.10 | 4 |
| 16 | 213.5 | 3.44 | 16.11 | 2.42 | 4 |
| 17 | 196.8 | 2.94 | 14.94 | 4.48 | 5 |
| 18 | 203.4 | 2.74 | 13.47 | 4.04 | 5 |
| 19 | 207.1 | 2.98 | 14.39 | 4.32 | 5 |
| 20 | 211.4 | 0.76 | 3.60 | 1.08 | 5 |
| 21 | 214.1 | 4.11 | 19.20 | 5.76 | 5 |
| 22 | 197.1 | 2.93 | 14.87 | 2.23 | 6 |
| 23 | 203.5 | 3.14 | 15.43 | 2.31 | 6 |
| 24 | 207.6 | 3.24 | 15.61 | 2.34 | 6 |
| 25 | 212.9 | 2.88 | 13.53 | 2.03 | 6 |
| 26 | 214.9 | 3.17 | 14.75 | 2.21 | 6 |

Conclusions: Albulin-G entered the circulation following pulmonary insufflation. Bioavailability following pulmonary insufflation was 7, 8 and 10% (relative to IV dosing) for different formulations. $C_{max}$ occurred 2.4 to 2.8 hours after pulmonary insufflation. The elimination half-life was 6 hours after IV injection and 9 to 14 hours after pulmonary insufflation. The $C_{max}$ and the AUC for Albulin-G were both correlated with the maximum decline in blood glucose and with the area under the effect curve for serum glucose. A dose of 3 mg/kg IV of Albulin-G resulted in severe hypoglycemia and deaths in fasted rats. An IV dose of 1 mg/kg was tolerated without clinical signs.

* * *

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, patent publications, journal articles, abstracts, laboratory manuals, books, or other disclosures) as well as information available through Identifiers specific to databases such as GenBank, GeneSeq, or the CAS Registry, referred to in this application are herein incorporated by reference in their entirety.

Furthermore, the specification and sequence listing of each of the following U.S. patent applications are herein incorporated by reference in their entirety: U.S. Patent Application No. 60/341,811, filed on Dec. 21, 2001; U.S. Patent Application No. 60/360,000, filed Feb. 28, 2002; U.S. Patent Application No. 60/378,950, filed May 10, 2002; U.S. Patent Application No. 60/398,008, filed Jul. 24, 2002; U.S. Patent Application No. 60/411,355, filed Sep. 18, 2002; U.S. Patent Application No. 60/414,984, filed Oct. 2, 2002; U.S. Patent Application No. 60/417,611, filed Oct. 11, 2002; U.S. Patent Application No. 60/420,246, filed Oct. 23, 2002; U.S. Patent Application No. 60/423,623, filed Nov. 5, 2002; U.S. Patent Application No. 60/350,358, filed Jan. 24, 2002; U.S. Patent Application No. 60/359,370, filed Feb. 26, 2002; U.S. Patent Application No. 60/367,500, filed Mar. 27, 2002; U.S. Patent Application No. 60/402,131, filed Aug. 9, 2002; U.S. Patent Application No. 60/402,708, filed Aug. 13, 2002; U.S. Patent Application No. 60/351,360, filed Jan. 28, 2002; U.S. Patent Application No. 60/382,617, filed May 24, 2002; U.S. Patent Application No. 60/383,123, filed May 28, 2002; U.S. Patent Application No. 60/385,708, filed Jun. 5, 2002; U.S. Patent Application No. 60/394,625, filed Jul. 10, 2002; U.S. Patent Application No. 60/411,426, filed Sep. 18, 2002; U.S. Patent Application No. 60/370,227, filed Apr. 8, 2002; International Application No. PCT/US02/40891, filed Dec. 23, 2002; and International Application No. PCT/US02/40892, filed Dec. 23, 2002. Furthermore, the specification and sequence listing of U.S. patent application Ser. No. 10/775,180, filed Feb. 11, 2004, now U.S. Pat. No. 7,189,690, is hereby incorporated by reference in its entirety.

What is claimed is:

1. A fusion protein having insulin activity and comprising albumin fused to the N-terminus, C-terminus, or both termini of an insulin analog, wherein the insulin analog has a formula of: $B_{(1-30)}$—X-$A_{(1-21)}$;

wherein:

X is a polypeptide linking sequence selected from the group consisting of: NPNLPRLVR (SEQ ID NO:18), KDDNPNLPRLVR (SEQ ID NO:19), NDEMPAD (SEQ ID NO:20), GGGPQT (SEQ ID NO:21), and GAGSSSRRAPQT (SEQ ID NO:22);

$B_{(1-30)}$ is a B-chain of insulin; and $A_{(1-21)}$ is an A-chain of insulin.

2. The fusion protein of claim 1, wherein albumin is fused to the N-terminus of the insulin analog.

3. The fusion protein of claim 1, wherein albumin is fused to the C-terminus of the insulin analog.

4. The fusion protein of claim 1, wherein albumin is fused to the N-terminus and C-terminus of the insulin analog.

5. The fusion protein of claim 1, wherein X is NPNLPRLVR (SEQ ID NO:18).

6. The fusion protein of claim 1, wherein X is KDDNPNLPRLVR (SEQ ID NO:19).

7. The fusion protein of claim 1, wherein X is NDEMPAD (SEQ ID NO:20).

8. The fusion protein of claim 1, wherein X is GGGPQT (SEQ ID NO:21).

9. The fusion protein of claim 1, wherein X is GAGSSSRRAPQT (SEQ ID NO:22).

10. The fusion protein of claim 1, further comprising an N-terminal leader or signal sequence.

11. The fusion protein of claim 10, wherein the N-terminal leader or signal sequence is selected from the group consisting of albumin leader sequence, insulin leader sequence, MPIF-1 signal sequence, stanniocalcin signal sequence, invertase signal sequence, yeast mating factor alpha signal sequence, K. lactis killer toxin leader sequence, immunoglobulin Ig signal sequence, Fibulin B precursor signal sequence, clusterin precursor signal sequence, insulin-like growth factor-binding protein 4 signal sequence, acid phosphatase (PHO5) leader, pre-sequence of MFoz-1, pre-sequence of 0 glucanase (BGL2), S. diastaticus glucoamylase II secretion leader sequence, S. carlsbergensis alpha-galactosidase (MEL1) secretion leader sequence, Candida glucoamylase leader sequence, gp67 signal sequence for use in a baculovirus expression system, and S. cerevisiae invertase (SUC2) leader.

12. The fusion protein of claim 10, wherein the N-terminal leader or signal sequence is selected from the group consisting of a hybrid signal sequence (MKWVSFISLLFLFSSAYSRSLEKR; SEQ ID NO:3); an HSA/MF alpha-1 hybrid signal sequence (MKWVSFISLLFLFSSAYSRSLDKR; SEQ ID NO:4); a K. lactis killer/MFalpha-1 fusion leader sequence (MNIFYIFLFLLSFVQGSLDKR; SEQ ID NO:5); SEQ ID NO:6; SEQ ID NO:7; SEQ ID NO:8; SEQ ID NO:9; a modified HSA leader (MKWVTFISLLFLFAGVSG; SEQ ID NO:10); a modified HSA leader (MKWVTFISLLFLFGGVSG; SEQ ID NO:11); a modified HSA (S14) leader (MKWVTFISLLFLFSGVSG; SEQ ID NO:12); a modified HSA (G14) leader (MKWVTFLSLLFLFGGVSG; SEQ ID NO:13); a modified HSA (G14) leader (MKWVTFISLLFLFGGVLGDLHKS; SEQ ID NO:14); a consensus signal sequence (MPTWAWWLFLVLLLALWAPARG; SEQ ID NO:15); K. lactis killer toxin prepro sequence (MNIFYIFLFLLSFVQGLEHTHRRGSLDKR; SEQ ID NO:16); and inulinase sequence (MKLAYSLLLPLAGVSASVINYKR; SEQ ID NO:17).

13. The fusion protein of claim 1, wherein the fusion protein:
(a) does not bind to IGF-I receptor or binds with no more than 80% affinity, relative to the affinity of IGF-I for the IGF-I receptor; or
(b) does not exhibit mitogenic activity or exhibits mitogenic activity of no more than 50% relative to IGF-I.

14. The fusion protein of claim 13, wherein the fusion protein exhibits mitogenic activity of no more than 30% relative to IGF-I.

15. The fusion protein of claim 13, wherein the fusion protein exhibits mitogenic activity of no more than 10% relative to IGF-I.

16. The fusion protein of claim 13, wherein the fusion protein binds with no more than 60% affinity, relative to the affinity of IGF-I for the IGF-I receptor.

17. The fusion protein of claim 13, wherein the fusion protein binds with no more than 40% affinity, relative to the affinity of IGF-I for the IGF-I receptor.

18. The fusion protein of claim 13, wherein the fusion protein binds with no more than 20% affinity, relative to the affinity of IGF-I for the IGF-I receptor.

19. The fusion protein of claim 13, wherein the fusion protein binds with no more than 10% affinity, relative to the affinity of IGF-I for the IGF-I receptor.

20. The fusion protein of claim 13, wherein the fusion protein binds with no more than 5% affinity, relative to the affinity of IGF-I for the IGF-I receptor.

21. A polynucleotide encoding a fusion protein of claim 1.

22. An expression vector comprising the polynucleotide of claim 21.

23. An isolated host cell comprising the expression vector of claim 22.

24. A method of preparing an albumin-insulin fusion protein comprising fermenting the host cell of claim 23.

25. A pharmaceutical composition comprising a fusion protein of claim 1 and a pharmaceutical excipient.

26. A pharmaceutical aerosol composition comprising a fusion protein of claim 1 and a pharmaceutical excipient.

27. The pharmaceutical aerosol composition of claim 26, formulated for nasal delivery, pulmonary delivery, or both.

28. The pharmaceutical aerosol composition of claim 27, wherein the composition is a liquid aerosol or a dry powder aerosol.

29. The pharmaceutical aerosol composition of claim 28, wherein the liquid aerosol comprises droplets having an average diameter selected from the group consisting of:
(a) about 2 to about 10 microns;
(b) about 2 to about 6 microns;
(c) less than about 2 microns;
(d) about 5 to about 100 microns; and
(e) 30 to about 60 microns.

30. The pharmaceutical aerosol composition of claim 28, wherein the dry powder aerosol is a spray-dried powder aerosol or a freeze-dried powder aerosol.

31. A pharmaceutical aerosol composition for use in a propellant-based pMDI comprising a fusion protein of claim 1.

32. The pharmaceutical aerosol composition of claim 31, wherein the propellant is a non-CFC propellant.

33. A method of treating diabetes comprising administering the pharmaceutical composition of claim 25 to a patient in need thereof.

* * * * *

UNITED STATES PATENT AND TRADEMARK OFFICE
CERTIFICATE OF CORRECTION

PATENT NO. : 9,505,823 B2
APPLICATION NO. : 11/835114
DATED : November 29, 2016
INVENTOR(S) : Adam C. Bell et al.

Page 1 of 1

It is certified that error appears in the above-identified patent and that said Letters Patent is hereby corrected as shown below:

On the Title Page

Item (73) Assignee:
Remove "TEV A Biopharmaceuticals USA, Inc., Rockville, MD (US)" and insert
-- TEVA Biopharmaceuticals USA, Inc., Rockville, MD (US) --

Signed and Sealed this
Eighteenth Day of April, 2017

Michelle K. Lee
*Director of the United States Patent and Trademark Office*